(12) United States Patent
Swager et al.

(10) Patent No.: US 11,965,849 B2
(45) Date of Patent: Apr. 23, 2024

(54) SENSOR ENABLED BY CATALYTIC SYSTEM

(71) Applicant: Massachusetts Institute of Technology, Cambridge, MA (US)

(72) Inventors: Timothy Swager, Newton, MA (US); Mate Bezdek, Boston, MA (US); Richard Liu, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/244,188

(22) Filed: Apr. 29, 2021

(65) Prior Publication Data
US 2021/0341405 A1    Nov. 4, 2021

Related U.S. Application Data

(60) Provisional application No. 63/018,412, filed on Apr. 30, 2020.

(51) Int. Cl.
*G01N 27/12* (2006.01)
*B01J 31/18* (2006.01)
*G01N 33/00* (2006.01)

(52) U.S. Cl.
CPC ........ *G01N 27/125* (2013.01); *B01J 31/1815* (2013.01); *G01N 33/0031* (2013.01)

(58) Field of Classification Search
CPC .............. G01N 27/125; G01N 33/0031; B01J 31/1815
See application file for complete search history.

(56) References Cited

U.S. PATENT DOCUMENTS

| | | | | |
|---|---|---|---|---|
| 3,954,800 A | * | 5/1976 | Lowe | C07C 319/24 549/21 |
| 2007/0099067 A1 | * | 5/2007 | Malhotra | H01M 8/1004 429/492 |
| 2014/0107326 A1 | * | 4/2014 | Swager | C01B 32/19 205/555 |
| 2016/0340272 A1 | * | 11/2016 | Cizeron | C07C 11/04 |
| 2017/0322167 A1 | * | 11/2017 | Swager | G01N 27/126 |
| 2018/0053957 A1 | * | 2/2018 | Pez | H01M 4/9083 |
| 2019/0031832 A1 | * | 1/2019 | Swager | B01J 20/267 |
| 2019/0086360 A1 | | 3/2019 | Swager et al. | |
| 2019/0257747 A1 | * | 8/2019 | Massie | G01N 21/3518 |

OTHER PUBLICATIONS

International Search Report dated Aug. 6, 2021 in International Application No. PCT/US2021/029878.
Written Opinion of the International Searching Authority dated Aug. 6, 2021 in International Application No. PCT/US2021/029878.

* cited by examiner

*Primary Examiner* — Jermele M Hollington
*Assistant Examiner* — Taqi R Nasir
(74) *Attorney, Agent, or Firm* — Honigman LLP

(57) ABSTRACT

A sensor can include one or more of a semiconducting material, an oxidation catalyst, and an oxidation enhancer, the sensor being configured to detect an analyte, such as methane, a thiol, or both.

37 Claims, 35 Drawing Sheets

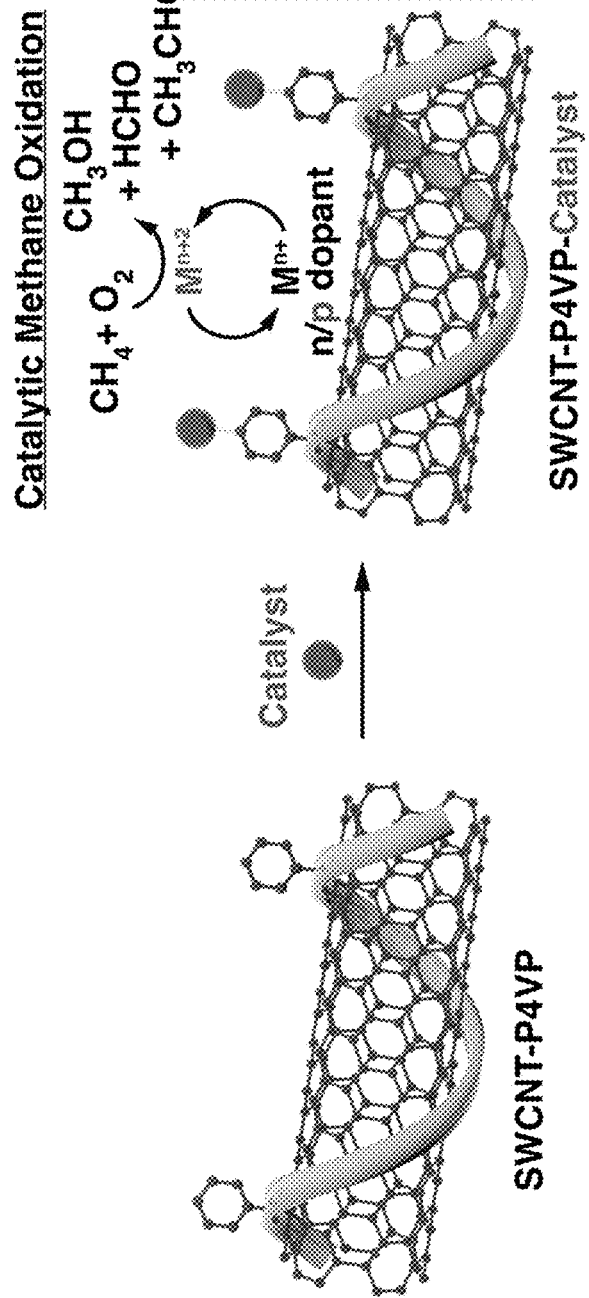
FIG. 1
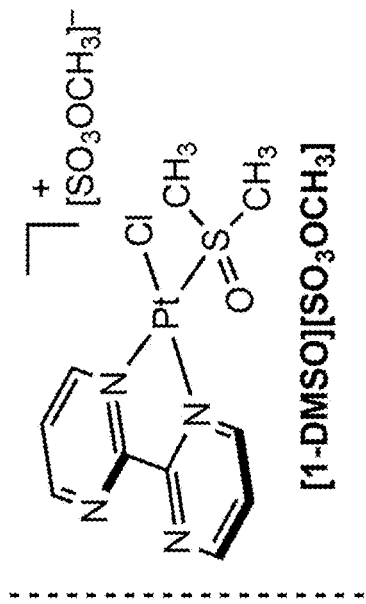
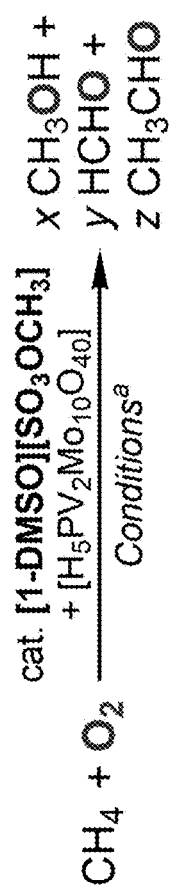
FIG. 2

FIG. 3A
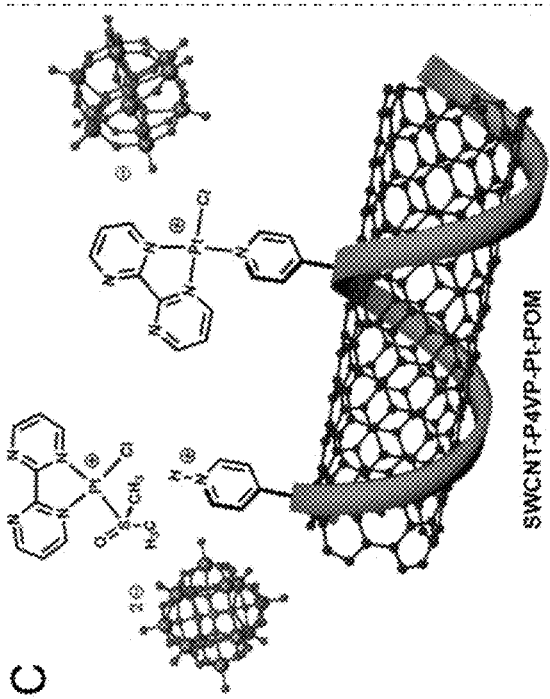
FIG. 3B
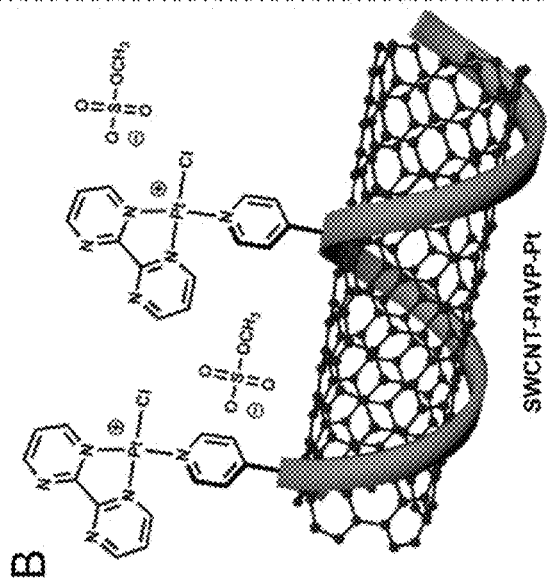
FIG. 3C
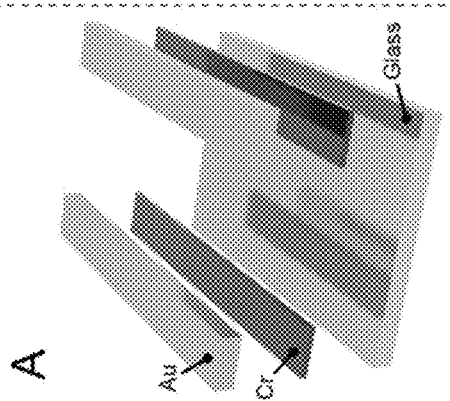
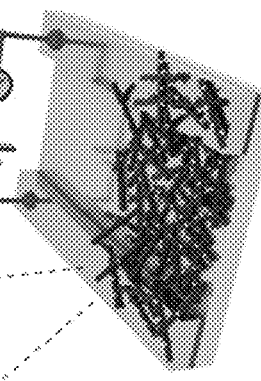
SWCNT-P4VP
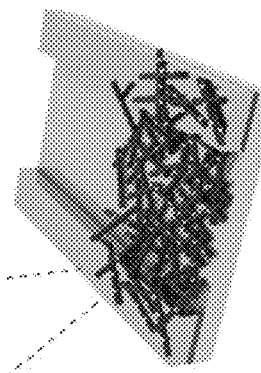
SWCNT-P4VP-Pt
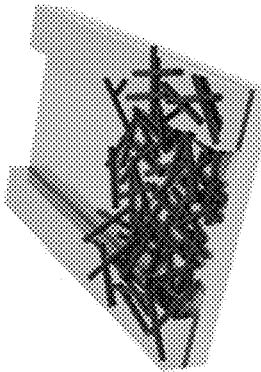
SWCNT-P4VP-Pt-POM

| Deviation from Standard Conditions | Outcome |
|---|---|
| 50-100 kΩ SWCNT-P4VP Base Resistance | Significant baseline drift. |
| 0.1-0.5 kΩ SWCNT-P4VP Base Resistance | Decreased sensitivity to $CH_4$ (LOD > 100 ppm). |
| Dilute [1-DMSO][SO$_3$OCH$_3$] soak (1.6 mM) | Decreased sensitivity to $CH_4$ (LOD > 500 ppm). |
| Concentrated [1-DMSO][SO$_3$OCH$_3$] soak (42 mM) | No change. |
| Dilute [H$_5$PV$_2$Mo$_{10}$O$_{40}$] soak (1.6 mM) | Decreased sensitivity to $CH_4$ (LOD > 200 ppm). |
| Concentrated [H$_5$PV$_2$Mo$_{10}$O$_{40}$] soak (42 mM) | No change. |

FIG. 18

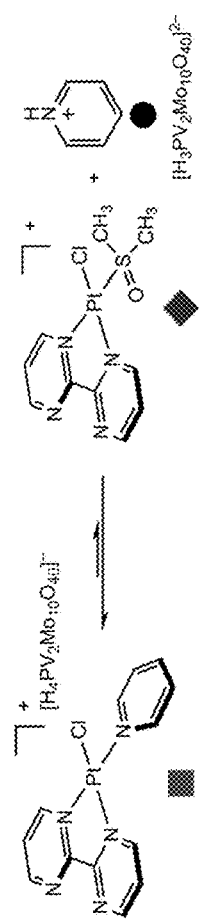
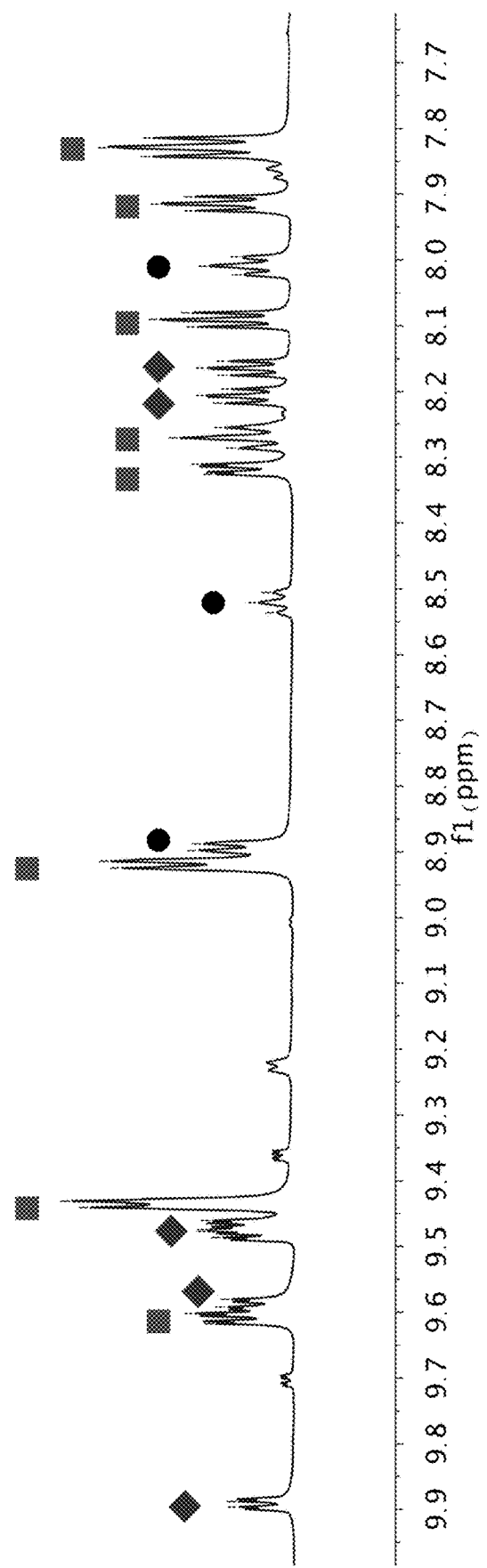
FIG. 22

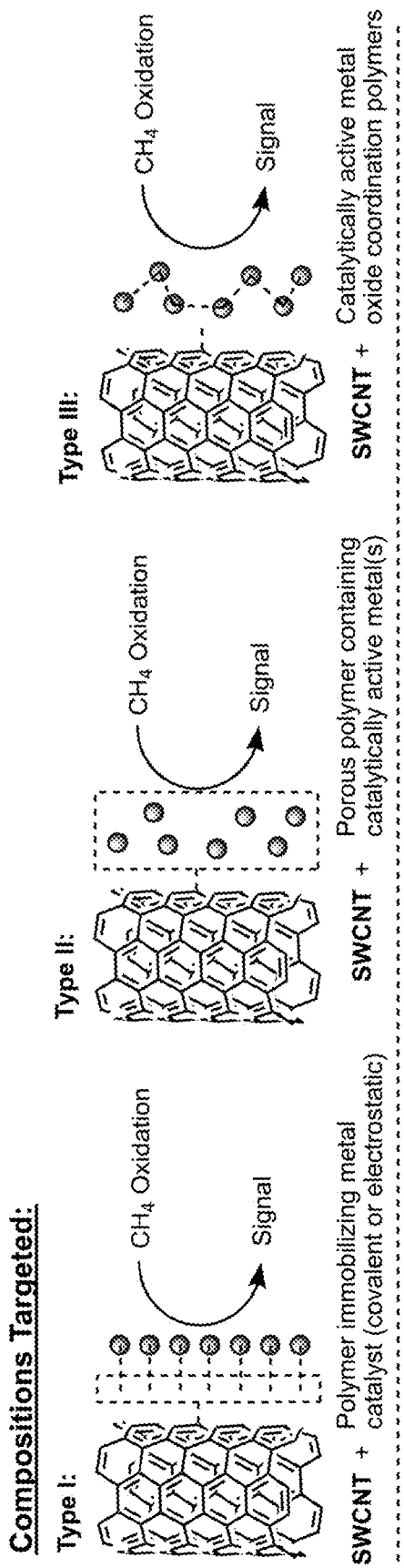
FIG. 23A
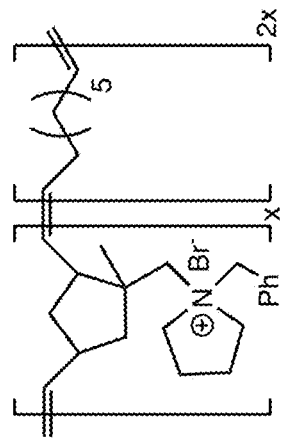
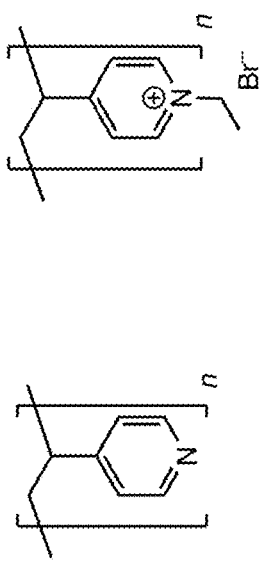
FIG. 23B

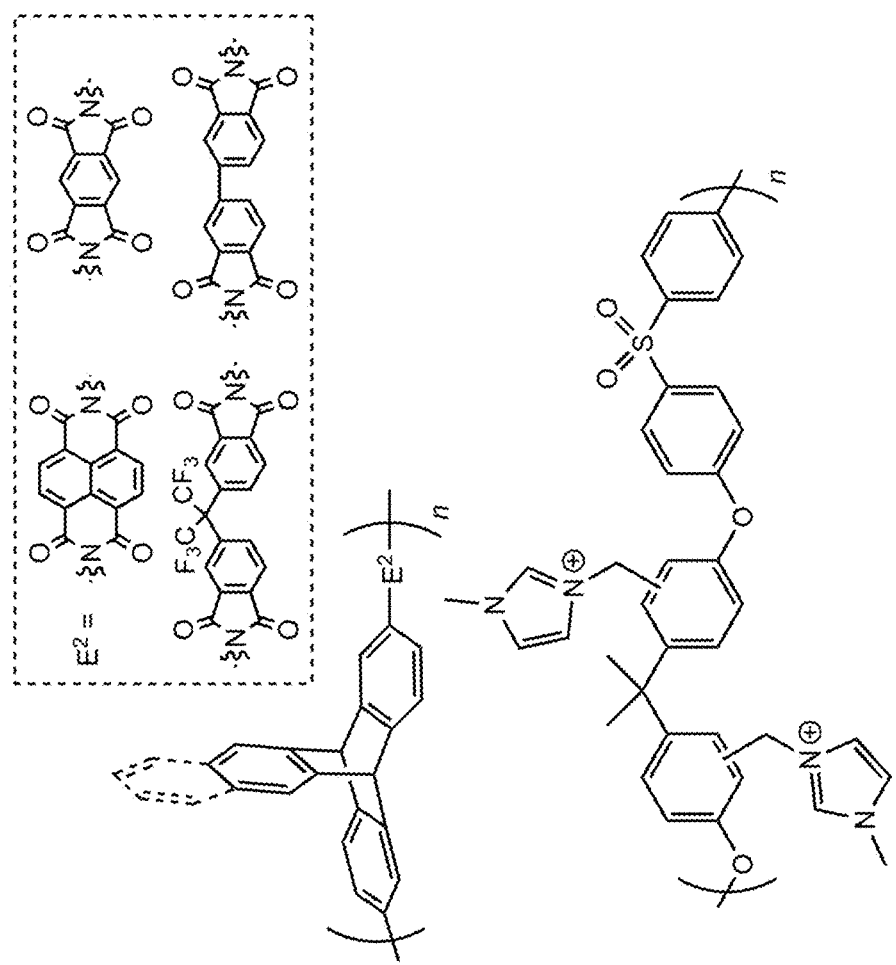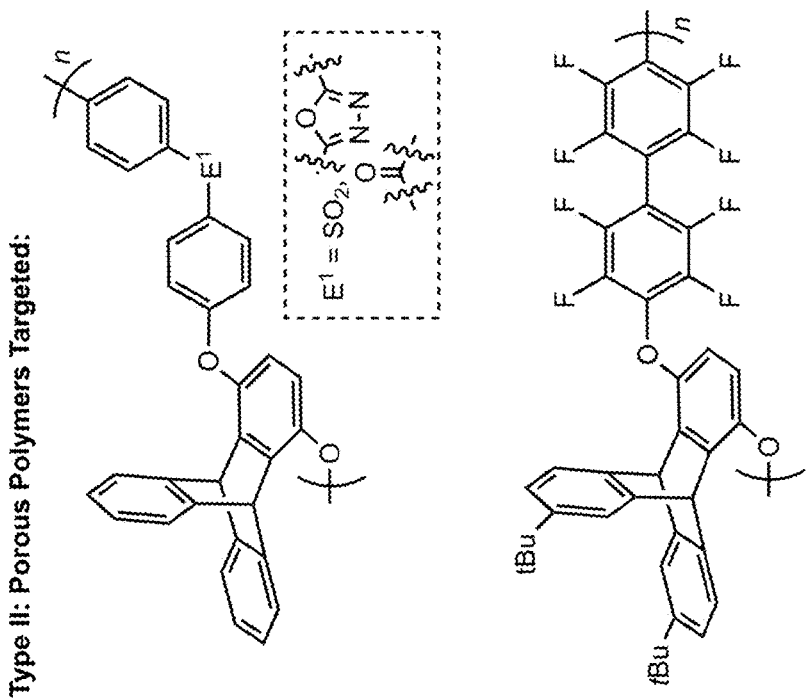
FIG. 23C

Type III: Metal oxides Targeted: $(WO_3)_n$ $(MoO_3)_n$ $(Fe_3O_4)_n$ $(Co_3O_4)_n$ $(V_2O_5)_n$ $(MnO_2)_n$
FIG. 23D
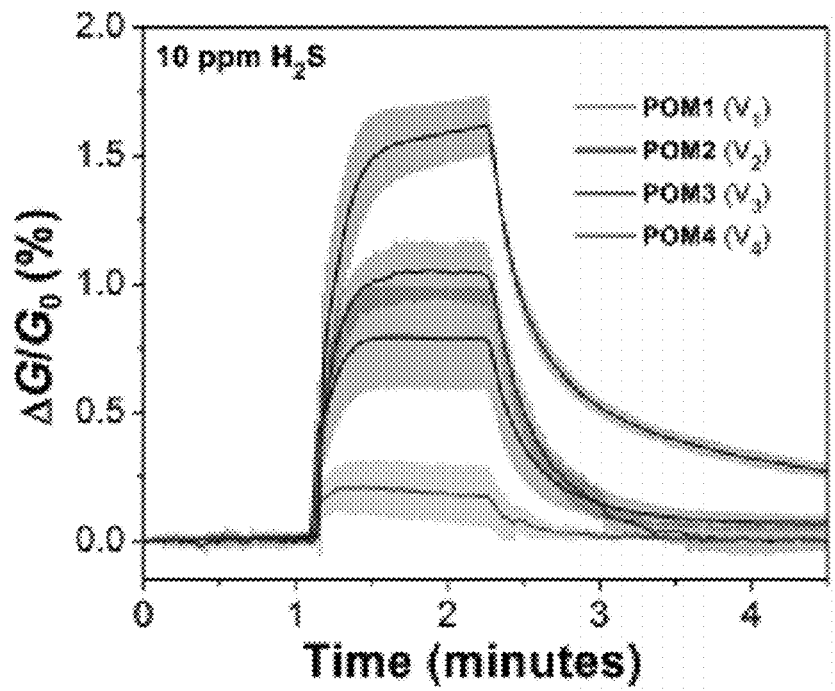
FIG. 24A
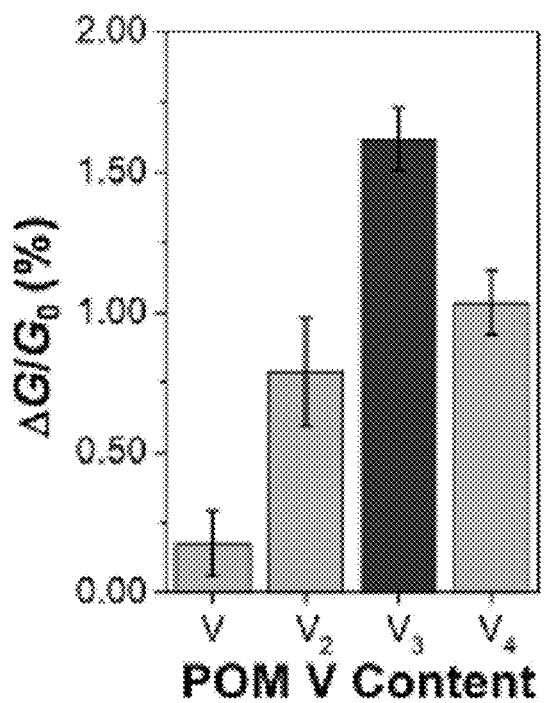
FIG. 24B

SENSOR ENABLED BY CATALYTIC SYSTEM

PRIORITY CLAIM

The application claims priority to U.S. Provisional Patent Application No. 63/018,412, filed Apr. 30, 2020, which is incorporated by reference in its entirety.

TECHNICAL FIELD

The invention relates to sensors and methods of sensing.

BACKGROUND

The selective detection of methane ($CH_4$) is paramount to environmental health as well as human safety in both domestic and industrial settings. On one hand, $CH_4$ is a high-impact anthropogenic greenhouse gas with a global warming potential 86 times larger than that of carbon dioxide ($CO_2$) over a 20-year period. See, for example, G. Myhre, et al. in *Climate Change* 2013: *The Physical Science Basis. Contribution of Working Group I to the Fifth Assessment Report of the Intergovernmental Panel on Climate Change* (Eds.: T. F. Stocker, D. Qin, G.-K. Plattner, M. Tignor, S. K. Allen, J. Boschung, A. Nauels, Y. Xia, V. Bex, P. M. Midgley). Cambridge University Press, Cambridge, United Kingdom and New York, NY, USA, 2013, pp. 659-740, which is incorporated by reference in its entirety. Colorless and odorless, methane also poses an acute explosion hazard at a concentration range of ca. 5-15% in air, an omnipresent risk in distribution centers, mines, and petroleum fractional distillation plants. See, for example, M. G. Zabetakis; 1965; Bulletin 627: Flammability Characteristics of Combustible Gases and Vapors. Washington, U.S. Department of the Interior, Bureau of Mines, which is incorporated by reference in its entirety.

Hydrogen sulfide ($H_2S$) is a highly corrosive contaminant gas omnipresent in natural gas streams that is also produced by the anaerobic bacterial breakdown of organic matter. See, for example, G. Hammer, et al. "Natural Gas" in *Ullmann's Encyclopedia of Industrial Chemistry*, 2006, Wiley-VCH, Weinheim, and L. Zhang, et al., *Water Res.* 2008, 42, 1-12, each of which is incorporated by reference in its entirety. With a permissible human exposure limit of ca. 20 ppm and immediate danger to life above 100 ppm defined by the National Institute for Occupational Safety and Health (NIOSH), the acute toxicity of $H_2S$ motivates the advancement of low-cost and portable sensing technologies that can rapidly identify $H_2S$ at trace concentrations in settings such as mines, natural gas pipelines and wastewater treatment plants. See, for example, NIOSH Pocket Guide to Chemical Hazards. "#0337". National Institute for Occupational Safety and Health (NIOSH), which is incorporated by reference in its entirety. Accordingly, $H_2S$ has attracted considerable research interest as a target analyte and the development of $H_2S$ sensors continues apace. See, for example, S. K. Pandey, et al., *Trends Anal. Chem* 2012, 32, 87-99, which is incorporated by reference in its entirety. Contemporary technologies for $H_2S$ detection include metal oxide/nanoparticle chemiresistors, electrochemical sensors as well as fluorescence-based detectors. See, for example, S. Mubeen, et al., *Anal. Chem.* 2010, 82, 250-257; Z. Song, et al., *Chem. Mater.* 2016, 28, 1205-1212; S. Park, et al., *Mater. Lett.* 2016, 181, 231-235; D. Feng, et al., *ACS Sens.* 2021, 6, 733-741; A. V. Kroll, et al., *Sens. Actuator B-Chem.* 1994, 21, 97-100; J. R. Hall, M. A. Schoenfisch, *Anal. Chem.* 2018, 90, 5194-5200; M. Strianese, et al., *Inorg. Chem.* 2020, 59, 15977-15986; and W.-M. He, et al., *Angew. Chem. Int. Ed.* 2021, 60, 8505-8509, each of which is incorporated by reference in its entirety. While high sensitivities can now be achieved using some of these materials and approaches, typical drawbacks of contemporary technologies include elevated operational temperatures, high power requirements, cross-selectivity issues with respect to volatile organic compounds (VOCs), bulky device enclosures, and short sensor lifetimes that hamper mobile deployment and real-time $H_2S$ monitoring. Therefore, it is imperative to develop new $H_2S$ sensing technologies that satisfy a range of key criteria for in-field application such as room temperature operation, low power requirements, rapidly reversible $H_2S$ response, high selectivity, as well as consistent device performance over time.

SUMMARY

In one aspect, a sensor for detecting an analyte can include a composition including a semiconducting material, an oxidation catalyst proximate to the semiconducting material, and an oxidation enhancer associated with the oxidation catalyst.

In another aspect, a sensor for detecting an analyte can include a composition including a semiconducting material, and a molecular methane oxidation catalyst that is proximate the semiconducting material. In certain embodiments, the sensor can include an oxidation enhancer.

In another aspect, a method of sensing an analyte can include exposing a sensor of any to a sample, and measuring an electrical property of the sensor. The sensor can detect methane, a thiol, or both.

In another aspect, a method of preparing a sensor for detecting an analyte can include placing a substrate, a semiconducting material, an oxidation catalyst proximate to the semiconducting material, and an oxidation enhancer associated with the oxidation catalyst in electrical communication with at least two electrodes.

In another aspect, a sensor array can include a first sensor and a second sensor, the first sensor responding to a first gas and the second sensor responding to a second gas, wherein the sensor array provides information about a gas mixture composition. The first sensor and the second sensor, independently, can be a sensor as described herein, for example, for $CH_4$ and thiol detection.

In certain circumstances, the sensor can include a polymer associating the oxidation catalyst with the semiconducting material. The polymer can include poly(4-vinylpyridine) (P4VP). The polymer can be hyperbranched, the polymer backbone can contain non-carbon elements, the polymer backbone can include non-carbon elements, for example, it can be partially or entirely comprised of non-carbon elements, or the polymer can have a porous structure. In certain circumstances, the polymer can be produced from condensation of metal or main group element with other elements from groups 15, 16 of 17, for example, the group 16 elements can contain oxygen or sulfur. The polymer can have crystalline domains that are connected together.

In one aspect, a conductivity of the semiconducting material changes when the oxidation catalyst is reacting with methane.

In one aspect, a conductivity of the semiconducting material changes when the oxidation catalyst is reacting with a thiol.

In certain circumstances, the thiol can be an alkyl thiol or hydrogen sulfide.

In certain circumstances, the semiconductor material can function as the oxidation enhancer. The semiconducting material can include a carbon nanotube, for example, a single-walled carbon nanotube. The semiconducting material can include a nanocarbon material. The semiconducting material can contain graphene.

In certain circumstances, the semiconducting material can be modified to bind the oxidation catalyst.

In certain circumstances, the oxidation enhancer can include a polyoxometalate, for example, a tungsten polyoxometalate or a molybdenum polyoxometalate. In certain circumstances, the polyoxometalate can include vanadium. The oxidation enhancer can include a polymer, an inorganic oxide, inorganic salt, inorganic halide, a high electron affinity molecule, nanoparticles, or a porous solid.

In certain circumstances, the oxidation catalyst can be a methane oxidation catalyst.

In certain circumstances, the oxidation catalyst can be a thiol oxidation catalyst. For example, the oxidation catalyst can be a hydrogen sulfide oxidation catalyst.

In certain circumstances, the oxidation catalyst can include platinum, tungsten, molybdenum, copper, iron, osmium, cobalt, rhodium, palladium, vanadium, osmium, gold, cerium, iridium, iron, manganese, silver, or europium.

In certain circumstances, the oxidation catalyst can include nanoparticles.

In certain circumstances, the sensor is configured to that the composition is located between two electrodes.

In certain circumstances, the composition can be deposited on a flexible substrate.

In certain circumstances, the sensor can detect methane by a change in conductivity of electrical characteristics of a circuit containing the sensor.

In certain circumstances, the sensor can detect a thiol by a change in conductivity of electrical characteristics of a circuit containing the sensor.

In certain circumstances, the sensor can detect methane, a thiol or both by a change in conductivity of electrical characteristics of a circuit containing the sensor. For example, the sensor response can inform about the composition of a gas mixture.

In certain circumstances, the sensor can detect a thiol by a change in conductivity of electrical characteristics of a circuit containing the sensor.

In certain circumstances, the sensor can include a second composition that differs from the composition. For example, the second composition can include a different enhancer.

Other aspects, embodiments, and features will be apparent from the following description, the drawings, and the claims.

BRIEF DESCRIPTION OF THE DRAWINGS

FIG. 1 depicts a schematic illustration of catalyst incorporation into SWCNT-P4VP composite and catalytic methane oxidation. N/p doping can give rise to conductance change and therefore sensor response. P4VP=poly(4-vinylpyridine).

FIG. 2 depicts aerobic methane oxidation with a platinum-polyoxometalate precatalyst under mild conditions. Conditions: 2.88 mol of precatalyst, 2 mL of $H_2O$, 30 mol of $[H_5PV_2Mo_{10}O_{40}]$, 30 bar $CH_4$, 2 bar $O_2$, 50° C., 4 h. x=46, y=9, z=41.

FIGS. 3A-3C depict a device fabrication schematic and composition of SWCNT-P4VP-Pt-POM on a glass substrate containing a gold electrode pattern.

FIG. 4A shows control $CH_4$ sensing experiments omitting all selector components, P4VP, $[1\text{-DMSO}]^+$ or $[H_5PV_2Mo_{10}O_{40}]$ contrasted with the sensing response of SWCNT-P4VP-Pt-POM. Inset: averaged conductance trace of SWCNT-P4VP-Pt-POM in response to 0.5% of $CH_4$ in air (RH=10±5%) at room temperature. FIG. 4B shows averaged conductance trace of SWCNT-P4VP-Pt-POM in response to three repeated 120 s exposures of 0.5% of $CH_4$ each in air at room temperature. FIG. 4C shows chemiresistive responses of SWCNT-P4VP-Pt-POM to 120 s exposures to various $CH_4$ concentrations in air (maroon), dry air (gray) or $N_2$ (blue) carrier gas at room temperature. FIG. 4D shows chemiresistive responses of SWCNT-P4VP-Pt-POM to 120 s exposures to various $CH_4$ concentrations in air at room temperature. Shaded areas represent standard deviations (N=4).

FIG. 6A shows an average device response of SWCNT-P4VP-Pt-POM with standard deviations (N=4 sensors) toward 400 ppm of various interferants in air at room temperature. FIG. 6B shows a normalized average response of freshly prepared and aged SWCNT-P4VP-Pt-POM devices with standard deviations (N=4 sensors) toward 0.5% of $CH_4$ in air at room temperature.

FIG. 8A shows survey XPS spectrum of SWCNT-P4VP-Pt-POM. FIGS. 8B-8G show high-resolution XPS spectra highlighting composition changes between SWCNT-P4VP-Pt (red) and SWCNT-P4VP-Pt-POM (blue). Note that in c), overlap of peaks corresponding to N (is) and Mo (3p) is observed for SWCNT-P4VP-Pt-POM.

FIG. 13A shows before and FIG. 13B shows after exposure of SWCNT-P4VP-Pt-POM device to ~0.5% of $CH_4$ in air (120 s). FIG. 13C shows a purging device enclosure with air for 120 s returns the initial resistance readout, demonstrating sensor reversibility. In this experiment, the multimeter leads were connected directly to the device breadboard platform shown in FIG. 10B.

FIGS. 17A-17C show SEM images of the SWCNT-P4VP-Pt-POM device surface at various magnifications. FIG. 17D shows cross-sectional SEM image of the SWCNT-P4VP-Pt-POM device edge.

FIG. 18: Optimization of chemiresistor fabrication procedure.

FIG. 22 depicts the aromatic region of the $^1H$ NMR (400 MHz) spectrum of the reaction between [1-Py][$SO_3OCH_3$] and [$H_5PV_2Mo_{10}O_{40}$] in DMSO-$d_6$ at 23° C.

FIGS. 23A-23D depict polymer types targeted.

FIG. 24A depicts a graph showing averaged conductance trace (represented as $\Delta G/G_0$, %) of SWCNT-P4VP-POMX (X=1-4) in response to 10 ppm of $H_2S$. FIG. 24B depicts a graph showing chemiresistive responses of SWCNT-P4VP-Pt-POMX (X=1-4) to 1 min $H_2S$ exposures (10 ppm). Shaded areas and error bars represent standard deviations (N=4), all data were collected in air at room temperature.

In FIG. 26B, high resolution XPS spectrum of V 2p of $H_6PV_3Mo_9O_{40}$ shown for reference.

DETAILED DESCRIPTION

Figure 4A:
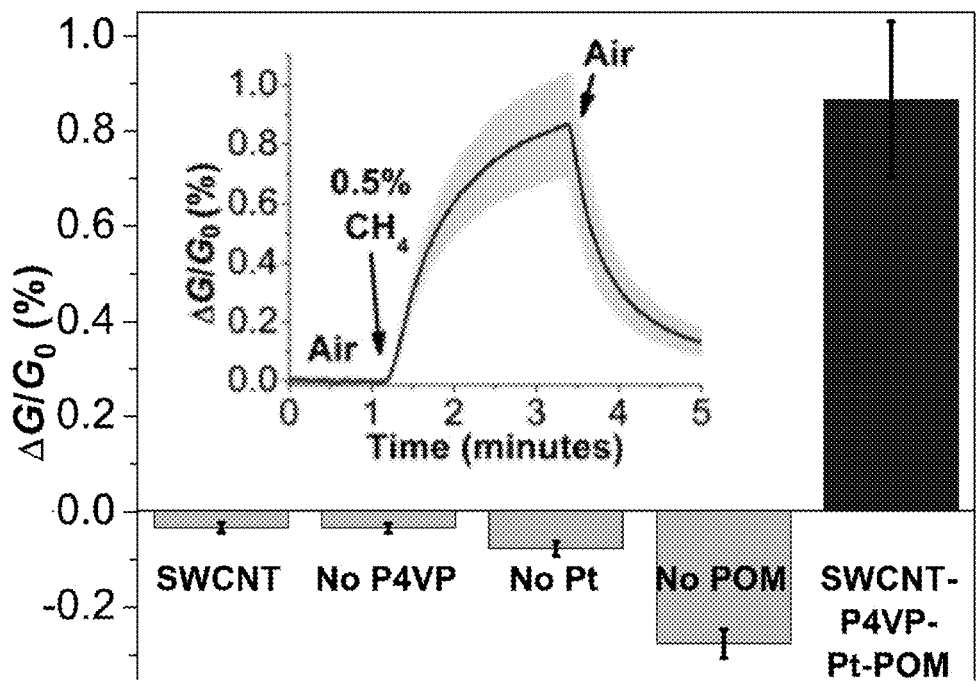
FIGS. 4A-4D depict chemiresistive responses of a sensor.
Figure 4B:
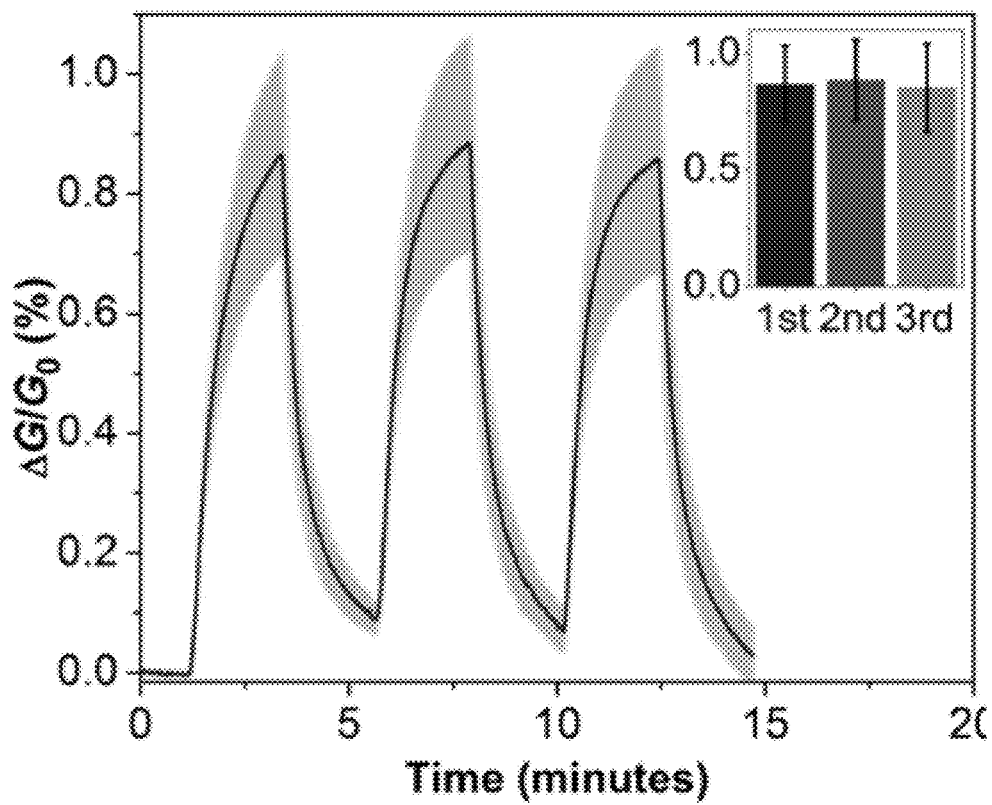

A chemiresistive sensor is described for the detection of hydrocarbons, such as methane ($CH_4$), a potent greenhouse gas that also poses an explosion hazard in air. The chemiresistor allows for the low-power, low-cost and distributed sensing of $CH_4$ with environmental implications for gas leak detection in homes, production facilities and pipelines. For example, the chemiresistors can be based on single-walled carbon nanotubes (SWCNTs) noncovalently functionalized with poly(4-vinylpyridine) (P4VP) that enable the incorporation of a platinum-polyoxometalate (Pt-POM) $CH_4$ oxidation precatalyst into the sensor by P4VP coordination. The resulting SWCNT-P4VP-Pt-POM composite showed ppm-level sensitivity to $CH_4$ and good stability to air as well as time, wherein the generation of a high-valent platinum intermediate during $CH_4$ oxidation is proposed as the origin of the observed chemiresistive response. In addition, the chemiresistor exhibits a selective response for $CH_4$ over heavier hydrocarbons such as benzene, toluene and hexanes at room temperature in air. The utility of the sensor in detecting $CH_4$ using a simple handheld multimeter was also demonstrated. Another SWCNT-P4VP-Pt-POM composition can be used to detect hydrogen sulfide.

Polyoxometalates (POMs) that adopt a "Keggin" structure of the general formula $H_{(3+n)}[PV_nMo_{(12-n)}O_{40}]$ (n=1-6) can catalyze the aerobic oxidation of a wide range of organic substrates including thiols. See, for example, I. A. Weinstock, et al., Chem. Rev. 2018, 118, 2680-2717, which is incorporated by reference in its entirety. A key to the rich aerobic oxidative catalytic reactivity of $H_{(3+n)}[PV_nMo_{(12-n)}O_{40}]$ is a propensity to participate in reversible redox chemistry and regeneration by $O_2$ upon reduction. See, for example, R. Neumann, Inorg. Chem. 2010, 49, 3594-3601, which is incorporated by reference in its entirety.

The sensor described herein can be used to detect an analyte. In general, the sensor includes a composition. The composition can include a semiconducting material, an oxidation catalyst proximate to the semiconducting material, and an oxidation enhancer associated with the oxidation catalyst. The oxidation catalyst can be associated with the semiconducting material through a covalent or non-covalent functionalization. Electronic properties of the composition can change in the presence of the analyte. For example, a conductivity property of the semiconducting material can change in the presence of the analyte because of an oxidation reaction promoted by the oxidation catalyst, the oxidation enhancer, or the combination thereof. The conductivity property can include conductance, resistance, or another property of the composition. For example, increased conductivity can be used to change the frequency of an associated resonance circuit that can be excited electrically of with electromagnetic radiation.

The oxidation catalyst is proximate to the semiconducting material. The oxidation catalyst interacts interact with the semiconductor material in a way that changes its conductivity. The oxidation catalyst can undergo electron transfer or partial change transfer with the semiconductor. The oxidation catalyst could additionally switch between states as part of the catalytic cycle that modulates local electrostatic interactions that impede or enhance carrier (holes or electrons) transport in the semiconducting material. This effect can be the result of geometry changes or changes in the coordination about the catalyst. For example, the oxidation catalyst can be bound to a ligand that is covalently anchored to a carbon nanotube. The oxidation catalyst can also directly interact with the semiconductor and for example could be bound to either oxygen or sulfur atoms in the case that the semiconductor is inorganic. For a carbon containing semiconductor it could be bound to nitrogen or carbon groups. Alternatively, the oxidation catalyst can be present in a carrier, such as a fluorocarbon oil, that is in contact with the semiconductor material. In this case the catalyst can be reversibily associating and dissociating with the semiconductor. It is also possible that another molecule or nanoparticle in the mixture could mediate the charge transfer events between the catalyst and the semiconductor. In this case, methane, oxygen and other gases can diffuse into the oil. In some cases, it may be advantageous to have a porous polymer overcoating over the semiconductor material that contains the catalyst and/or oxidation enhancer. In this context, porous indicates a material in which gas can diffuse. In some cases, the porous polymer can actually concentrate the methane from its surroundings. In some cases, the porous polymer can selectively concentrate methane or thiol from its surroundings over water vapor, such that the sensor can operate under variable humidity conditions. In another example, the oxidation catalyst can be deposited by evaporation of a solution on the semiconductor material. The proximity leads to a sensor in which conductivity of the semiconducting material changes when the oxidation catalyst is interacting with the analyte, such as methane or a thiol. The thiol can be an alkyl thiol or hydrogen sulfide.

The semiconductor material can include a semiconductor nanowire, a nanocarbon material, a network of semiconductor nanowires, or a semiconductive solid. In certain circumstances, the semiconductor material can include a carbon nanotube, graphene, p-type non-carbon based semiconductor, inorganic semiconductor, or n-type semiconductor. The p-type non-carbon based semiconductor can be SnO, $MoS_2$, CuO or NiO. The n-type semiconductor can be $SnO_2$, $TiO_2$, $V_2O_5$, $WO_3$, $MoO_3$ or ZnO. For example, the semiconductor material can be a single-walled carbon nanotube or a plurality of single-walled carbon nanotubes.

In certain circumstances, the semiconductor material can be modified to bind the oxidation catalyst. The binding can be covalent or by coordination. In certain circumstances, the semiconductor materials can function as the oxidation enhancer in the composition, for example, in compositions including $TiO_2$, $V_2O_5$, $WO_3$, and $MoO_3$.

The composition can include a polymer associating the oxidation catalyst with the semiconducting material. In this embodiment, the polymers can be organized into three classes, represented as examples in FIGS. 23A-23D. Type I polymers immobilize the metal catalyst by coordination or electrostatic attraction of a charged group. Type II porous polymers contain large free volumes and are good hosts for catalytically active nanoparticles. Type III coordination polymers that can include metal oxides, metal sulfides, metal halides, silica sol-gels, silicates, metal ligand compositions, or mixtures thereof. In some cases materials such as the metal oxides can function as catalysts themselves or may host additional metals. In all cases, the composite is expected to efficiently oxidize an analyte, such as methane, and give rise to a sensing response.

In certain circumstances, the polymer can be a vinyl-based polymer, such as poly(4-vinylpyridine) (P4VP). In accordance with the Type I, Type II and Type III polymer classes, the polymer can be hyperbranched, the polymer backbone can contain non-carbon elements, be completely composed of inorganic elements, or the polymer can have a porous structure, or combinations of these features. For example, the polymer can be produced from condensation of metal or main group element with other elements from groups 15, 16 of 17. In certain embodiments, the group 16 element can contain oxygen or sulfur. In other cases the polymer can be generated by hydrolysis of precursors to give oxide materials. For example, $Si(OEt)_4$ can be hydrolyzed to create silicate polymers and the addition of organic groups can be readily incorporated by including R—Si(OEt)$_3$ as the sole silicon group or as a component of the composition. Similar polymers can be generated based on phosphorous in its +5 high oxidation state. For example, polyphosphoric acid could be the polymer used in conjunction with other materials. The R group attached to the polymer can be any molecular fragment that produces desirable properties. For example, some cases R can have an affinity for methane and in other cases R can be used to interact with the oxidation catalyst or oxidation enhancer.

The oxidation enhancer is a component that interacts with the oxidation catalyst to improve the performance of the catalyst, in terms of efficiency, turn over rate, selectivity, or combinations thereof. The oxidation enhancer can include a polyoxometalate, for example, a tungsten polyoxometalate or a molybdenum polyoxometalate. The polyoxometalate can include phosphorous, platinum, tungsten, molybdenum, copper, iron, osmium, cobalt, rhodium, palladium, vanadium, osmium, gold, cerium, iridium, iron, manganese, silver, or europium. For example, the polyoxometalates (POMs) can have the general formula $H_{(3+n)}[PV_nMo_{(12-n)}O_{40}]$ (n=1-6). In certain embodiments, the oxidation enhancer can include a polymer, an inorganic oxide, nanoparticles, or a porous solid.

In the composition, the oxidation catalyst is a catalyst that oxidizes the analyte. The oxidation catalyst can include a molecular oxidation catalyst such as a molecular methane oxidation catalyst or a thiol oxidation catalyst. The oxidation catalyst can include a metal or metal ion. The oxidation catalyst can include platinum, tungsten, molybdenum, copper, iron, osmium, cobalt, rhodium, palladium, vanadium, osmium, gold, cerium, iridium, iron, manganese, silver, or europium, or combinations thereof. For example, the oxidation catalyst can be a platinum complex, $EuCl_3$, $Eu(CH_3CO_2)_3$, $Eu_2(CO_3)_3$, $Eu_2(NO_3)_3$, [(n-Bu$_4$N]VO$_3$-pyrazine-2-carboxylic acid —$H_2O_2$, $VO(acetylacetonate)_2$, $VOF_3$—$(CF_3CO)_2O$, $V_2O_5$—$(CF_3CO)_2O$, $Pd(CH_3CO_2)_2$, $RhCl_3$, $CoCl_2$, $OsCl_3$, $FeCl_3$, $CuCl_2$, or [(n-Bu)$_4$N]$_4$[W$_{10}$O$_{32}$]-UV light, or combinations thereof. In certain embodiments, the oxidation catalyst can include nanoparticles. In some cases, these nanoparticles are metal nanoparticles composed of one of more types of metallic element. The polymer structures can be used to stabilize small high activity metal nanoparticles that are more reactive with methane. The metal nanoparticles can have other groups associated with their surfaces that enhance reactivity.

A method of preparing a sensor for detecting an analyte can include placing a substrate, a semiconducting material, an oxidation catalyst proximate to the semiconducting material, and an oxidation enhancer associated with the methane oxidation catalyst in electrical communication with at least two electrodes. A method of sensing an analyte can include exposing a sensor to a sample, and measuring an electrical property of the sensor. The electrical property can be determined directly through wiring it in a circuit or can be read by a change in the resonant characteristics of the circuit. For example, a circuit can be tuned to resonate at a frequency that is used for radio signals. This can result in a circuit that can be powered and read by radio waves and such technology result in sensors that can be read and powered even by a smartphone. The sensor can detect the analyte, for example, methane or a thiol, by a change in conductivity or electrical characteristics of a circuit containing the sensor.

In certain embodiments, a sensor can include a conductive region in electrical communication with at least two electrodes, where the conductive region includes a composite. In certain embodiments, the polymer can include a nitrogenous group available to form a covalent bond with a linker. In certain embodiments, the linker can form a quaternary nitrogen bond with the polymer. In certain embodiments, the linker is derived from an alkyl halide group. The nitrogenous group is a group having a nitrogen nucleophilic nitrogen atom. The nitrogenous group can be a pendant amino, pyridyl, pyrimidyl, oxazolyl, parazole, imidazole, thiazole, quinolinyl, purinyl, or isoquinolinyl moiety. In certain embodiments, the linker on the substrate can be activated to bind the polymer by dehydration reaction with activating electrophiles such as thionyl chloride of triflic anhydride. In certain embodiments, the composite includes a carbon nanotube that is functionalized with poly(4-vinylpyridine) (P4VP). The functionalization can be non-covalent. The sensor can behave as a dosimeter giving an integrated (irreversible) response to a desired analyte.

Carbon nanotubes can be constructed with length-to-diameter ratio of up to 132,000,000:1, significantly larger than for any other material. These cylindrical carbon molecules have unusual properties, which are valuable for nanotechnology, electronics, optics and other fields of materials science and technology. In particular, owing to their extraordinary thermal conductivity and mechanical and electrical properties, carbon nanotubes find applications as additives to various structural materials.

Carbon nanotubes are members of the fullerene structural family. These sheets are rolled at specific and discrete (chiral) angles, and the combination of the rolling angle and radius decides the nanotube properties. Nanotubes are categorized as single-walled nanotubes (SWNTs) and multi-walled nanotubes (MWNTs). Individual nanotubes naturally align themselves into "ropes" held together by van der Waals forces, more specifically, π-stacking.

Applied quantum chemistry, specifically, orbital hybridization best describes chemical bonding in nanotubes. The chemical bonding of nanotubes is composed entirely of $sp^2$ bonds, similar to those of graphite. These multiple bonds, which are stronger than the individual single $sp^3$ bonds found in alkanes and diamond, provide nanotubes with their unique strength.

Functionalization can be based on the formation of a linkage between functional entities and the carbon skeleton of nanotubes. The linkage can be covalent. It could also be divided into direct covalent sidewall functionalization and indirect covalent functionalization with carboxylic groups on the surface of CNTs. Direct covalent sidewall functionalization is associated with a change in hybridization from $sp^2$ to $sp^3$ and a simultaneous loss of conjugation. In some cases two carbons next to each other can be functionalized and a ring structure can connect functional groups to the graphene surface of the CNT. Ligands that interact with the catalyst can be attached to the CNTs. Indirect covalent functionalization takes advantage of chemical transformations of carboxylic groups at the open ends and defects in the sidewalls. These carboxylic groups might have existed on the as-grown CNTs and also be further generated during oxidative treatments. In order to increase the reactivity of CNTs, the carboxylic acid groups usually need to be converted into acid chloride and then undergo an esterification or amidation reaction. The drawback of covalent functionalization is that the structure of CNTs has to be destroyed, resulting in significant changes in their physical properties.

Non-covalent functionalization is mainly based on supramolecular complexation using various adsorption forces, such as van der Waals force, hydrogen bonds, electrostatic force, and π-stacking interactions. Compared to the chemical functionalization, non-covalent functionalization has the advantages that it could be operated under relatively mild reaction conditions and the graphitic electronic structure of CNTs could be maintained with minimal disruption.

In certain embodiments, a sensor can include a composite of a polymer and SWCNTs immobilized onto a substrate. In certain embodiments, the substrate can include metal electrodes, and a linker can be grafted on the substrate. The linker can connect the substrate and the composite of the polymer and SWCNTs. In certain embodiments, the linker can covalently bond the polymer to the substrate. In other cases the polymers can be bound by electrostatic or ionic interaction to the substrate. For purely inorganic polymers, including metal oxides and metal sulfides, the grafting interactions will involve many ionic or electrostatic interactions as well as bonding. In certain embodiments, metal nanoparticles or ions can be further included as a metal sensitizer to confer further selectivity or sensitivity to the device. The metal nanoparticles or ions can be coordinated by residual moieties in the polymer that are not consumed by grafting to the substrate. In certain embodiments, the polymer can act as a ligand for a variety of metal ions. By incorporating a specific metal ion, the sensor can selectively detect an analyte.

The substrate can be either rigid or flexible. In certain embodiments, the substrate can be made of rigid materials, such as glass, plastic, wood, concrete, rocks, metal chalcogenides, rigid polymers and their composites, passivated metals, bone, asphalt, graphite, silicon, semiconductors, a resonant circuit, ceramics, marble, or granite. In certain embodiments, the substrate can be made of flexible materials, such as paper, polymers, skin, cloth, tissue, plants, leather, thin sheets of semiconductors or metals, and tires. In certain embodiments, the substrate can be a flexible polymer substrate, for example, a polyimide.

In certain embodiments, the electrodes can include graphite, copper, aluminum, gold, or silver.

In certain embodiments, the linker can include an alkyl halide group. For example, the linker can be 3-bromopropyltrichlorosilane. In certain embodiments, the linker can be a cationic surface, for example, created by alkylating surface pyridyl groups which quaternizes the pyridine to form pyridinium groups.

In certain embodiments, metal nanoparticles can include silver, copper, gold, mercury, zinc, cobalt, rhodium, iridium, nickel, platinum, palladium, iron, ruthenium, manganese, tin, lead oxides or sulfides thereof.

For example, the glass substrate was patterned with gold electrodes and then subjected to grafting between gold electrodes and then subjected to organosilanization with 3-bromopropyltrichlorosilane. The resulting pendant alkyl bromide groups on the glass surface are then available to undergo quaternization chemistry with the pyridyl groups in a composite of P4VP and SWCNTs, thereby covalently bonding the polymer to the substrate. Residual pyridyl groups in the P4VP that are not consumed in the quaternization can subsequently be used to coordinate metal nanoparticles or metal ions chosen to confer further selectivity or sensitivity to the device. Many other ligands are possible to attach to the polymers and can include chelating ligands, carboxylates, phosphonates, sulfoxides, and ethers.

While environmental $CH_4$ levels are typically monitored using gas chromatography and optical gas analyzers' the development of alternative materials and approaches for $CH_4$ detection is ongoing and includes pellistors, metal oxides, photoacoustic devices as well as electrochemical and thermal wave sensors. See, for example, E. J. Dlugokencky, et al., *J. Geophys. Res.* 1994, 99, 17021-17043; J. Shemshad, et al., *Sens. Actuators B* 2012, 8, 77-92; D. R. Caulton, et al., *Proc. Natl. Acad. Sci. U.S.A.* 2014, 111 6237-6242; A. K. Thorpe, et al., *Remote Sens. Environ.* 2016, 179, 104-115; D. R. Caulton, et al., *Environ. Sci. Technol* 2019, 53, 4747-4754; T. Hong, et al., *Trends Anal. Chem* 2020, 78, 115820; J. Kamieniak, et al., *Trends Anal. Chem* 2015, 73, 146-157; N. S. Lawrence, *Talanta* 2006, 2, 385-392; A. Baranov, et al., *Sens. Actuators A* 2015, 233, 279-289; H. Ma, et al., *Sens. Actuators B: Chem.* 2013, 187, 221-226; A. Dey, *Mater. Sci. Eng. B* 2018, 229, 206-217; M. van den Bossche, et al., *Sens. Actuators B* 2017, 238, 501-509; D. Haridas, V. Gupta, *Sens. Actuators* B 2012, 166-167, 156-164; N. M. Vuong, et al., *Sens. Actuators B* 2014, 192, 327-333; G.-C. Liang, et al., *J. Phys. Chem. A* 2000, 104, 10179-10183; Z. Wang, et al., *Analyst* 2014, 139 5140-5147; T. Otagawa, et al., *J. Electrochem. Soc.* 1985, 132, 2951-2957, and J. A. Garcia, et al., *Int. J. Hydrogen. Energy* 1996, 9, 761-764, each of which is incorporated by reference in its entirety. Although high sensitivities can be achieved using some of these methods, drawbacks typically include poor selectivity, high device power consumption, elevated operational temperatures as well as expensive and bulky device enclosures that are impractical for real time, high spatial resolution field measurements. As a result, new methane sensing technologies are needed that are compact, inexpensive and portable with operational capability at or near ambient conditions.

Chemiresistors sensitive to analyte interactions offer a potential solution to these challenges. See, for example, T. M. Swager, *Angew. Chem. Int. Ed.* 2018, 57, 4248-4257, which is incorporated by reference in its entirety. In particular, single-walled carbon nanotubes (SWCNTs) are an attractive chemiresistor class owing to inexpensive fabrication, room temperature operation as well as ultra-low power requirements. See, for example, D. R. Kauffman, A. Star, *Angew. Chem.* 2008, 120, 6652-6673; *Angew. Chem. Int. Ed.* 2008, 47, 6550-6570; and V. Schroeder, S. Savagatrup, M. He, S. Lin, T. M. Swager, *Chem. Rev.* 2019, 119, 599-663, each of which is incorporated by reference in its entirety. Pristine (unfunctionalized) SWCNTs show no response to methane at room temperature, and as a result introduction of a selector is necessary to translate a molecular interaction into an electrical signal. Methane sensing using SWCNTs is still at an early stage however, owing to the difficulty of obtaining a selective response to the non-polar and inert $CH_4$ molecule via traditional selector-analyte interaction strategies such as adsorption, swelling, receptor/guest interactions or chemical reaction. See, for example, A. M. Rao, et al., *Nature* 1997, 388, 257-259; (b) J. Kong, et al., *Science* 2000, 287, 622-625; P. C. Jurs, et al., *Chem. Rev.* 2000, 100, 2649-2678; C. M. Hangarter, et al., *Nano Today* 2013, 8, 39-55; X. Tang, et al., *Nano Lett.* 2006, 6, 1632-1636; J. Wang, et al., *Environ. Sci. Technol.* 2008, 42, 2688-2693; Y. Weizmann, et al., *J. Am. Chem. Soc.* 2011, 133, 3238-3241; S. Savagatrup, et al., *Angew. Chem., Int. Ed.* 2017, 56, 14066-14070; B. Esser, et al., *Angew. Chem. Int. Ed.* 2012, 51, 5752-5756; and S. F. Liu, et al. *Angew. Chem. Int. Ed.* 2015, 54, 6554-6557, each of which is incorporated by reference in its entirety. For example, Star et al. constructed gas sensor arrays using metal-decorated SWCNTs but found no significant response to methane in the composites featuring 18 different metals. See, for example, A. Star, et al., *J. Phys. Chem. B* 2006, 110, 21014-21020, which is incorporated by reference in its entirety. Previously, conductance changes were reported for both SWCNTs and multi-walled CNTs decorated with Pd and $SnO_2$/ZnO nanocrystals, respectively, upon exposure to $CH_4$. See, for example, Y. Lu, et al., *Chem. Phys. Lett.* 2004, 391, 344-348; M. T. Humayun, et al., *J. Vac. Sci. Technol. A* 2016, A 34, 01A131-1-01A131-7; and M. T. Humayun, et al., *J. Vac. Sci. Technol. B* 2015, 33, 06FF01-1-06FF01-7, each of which is incorporated by reference in its entirety. However, selectivity studies were not carried out and the origin of the observed response in each case was not experimentally interrogated. Therefore, both sensitivity as well as selectivity for $CH_4$ continue to be significant challenges for metal-CNT composites.

An emerging strategy for analyte detection using SWCNTs involves a room-temperature chemical reaction of the analyte catalyzed by a selector on the SWCNT surface. See, for example, V. Schroeder, T. M. Swager, *J. Am. Chem. Soc.* 2018, 140, 10721-10725, which is incorporated by reference in its entirety. This approach is particularly attractive because the selector is not consumed during analyte detection, thus enabling long-term device stability and dose-independent sensitivity. Because SWCNT charge carrier densities are sensitive to surface electronic changes and can be modulated by catalyst redox cycling, the chemoselectivity of the surface reaction may be translated to selective analyte detection. Herein the application of this concept is reported to the detection of $CH_4$ under ambient conditions. Specifically, (Pt-POM) aerobic $CH_4$ oxidation precatalyst reported by Neumann and coworkers was incorporated into a platinum-polyoxometalate into a SWCNT-based chemiresistor (FIG. 2). See, for example, I. Bar-Nahum, et al., *J. Am. Chem. Soc.* 2004, 126, 10236-10237; for a structural revision of the Pt precatalyst reported therein, see: J. M. Villalobos, et al., *Organometallics* 2010, 29, 257-262, each of which is incorporated by reference in its entirety. By repurposing the known precatalyst as a selector, a lightweight chemiresistor for the selective detection of $CH_4$ at room-temperature in air was obtained, presenting a viable technology for the in-field, real-time monitoring of this challenging analyte.

The studies commenced with the fabrication of a SWCNT-based film incorporating the Pt-POM precatalyst in FIG. 2 for use as a chemiresistor. First, SWCNTs were dispersed in a DMF solution containing P4VP (P4VP=poly (4-vinylpyridine); SWCNT:P4VP 1:10 w/w) and spray-coated between gold electrodes on glass at 140° C. (1 mm gap, chromium adhesive layer) in a 4-channel array with a shared counter electrode (FIGS. 3A-3C, step 1). P4VP serves to de-bundle SWCNTs through pyridyl lone pair-π and π-π interactions with the CNT sidewalls, thereby increasing the analyte-accessible SWCNT surface area while restricting nanotube conduction pathways, attributes that are expected to yield improved chemiresistive sensing properties. See, for example, J. H. Rouse, *Langmuir* 2005, 21, 1055-1061, which is incorporated by reference in its entirety. In addition, free pyridyl groups in P4VP can be utilized to introduce metal selectors into the SWCNT-P4VP matrix by coordination. See, for example, B. Yoon, et al., *Chem. Mater.* 2016, 28, 5916-5924, each of which is incorporated by reference in its entirety. Accordingly, the device bearing the SWCNT-P4VP film was soaked in a DMSO solution containing [(bpym)Pt(DMSO)Cl][$SO_3OCH_3$] ([1-DMSO][$SO_3OCH_3$]; bpym=2,2'-bipyrimidine, DMSO=dimethylsulfoxide) for 18 hours at room temperature in order to immobilize the Pt complex in the SWCNT-P4VP network (FIGS. 3A-3C, step 2). The device was subsequently soaked in a DMSO solution of the POM [$H_5PV_2Mo_{10}O_{40}$] for 18 hours at room temperature in order to achieve anion exchange, thus furnishing the targeted SWCNT-P4VP-Pt-POM composite (FIGS. 3A-3C, step 3). The speciation of the Pt-POM complex on the chemiresistor surface is discussed in greater detail below.

In other circumstances, the POM can be tuned to alter the reactivity and sensitivity of the sensor. The combination of Pt-POM precatalysts with SWCNTs should yield composites of sufficiently high reactivity to rapidly oxidize $H_2S$ to $S_xO_y$ under ambient conditions and therein translate aerobic oxidation catalysis to a chemiresistive sensing response. Thus, SWCNT-Pt-POM composites can serve as a versatile starting point for the development of a new class of $H_2S$ sensors that operate via aerobic $H_2S$ oxidation catalysis. By rationally tuning the oxidizing ability of the constituent POMs, a high-performance sensor can be obtained that exhibits rapid and reversible responses to $H_2S$ at room temperature in air. The chemiresistor can be capable of detecting trace hydrogen sulfide with ppb-level detection limit, exhibits high selectivity to $H_2S$ over interferent gases and VOCs, and shows multi-month benchtop stability.

Compatibility of the chemiresistor with flexible polyimide substrates is also demonstrated.

Figure 7:
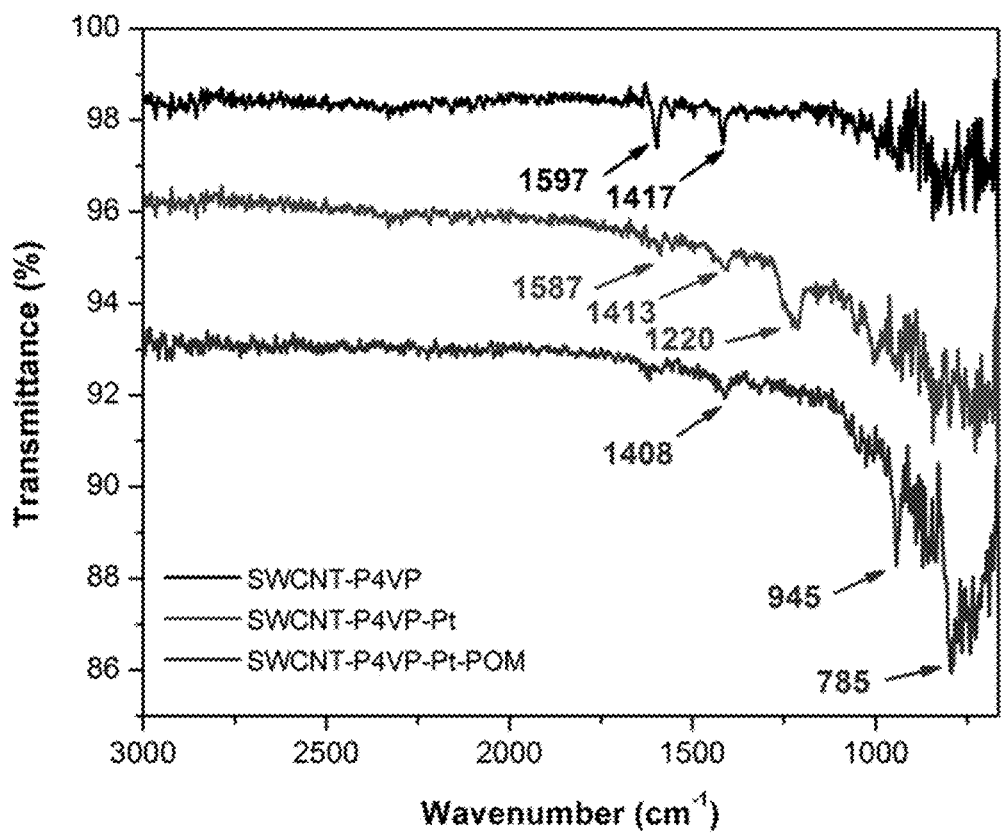
FIG. 7 depicts ATR-FTIR spectra of SWCNT-P4VP (black), SWCNT-P4VP-Pt (red) and SWCNT-P4VP-Pt-POM (blue) thin films on glass substrates.
Figure 8A:
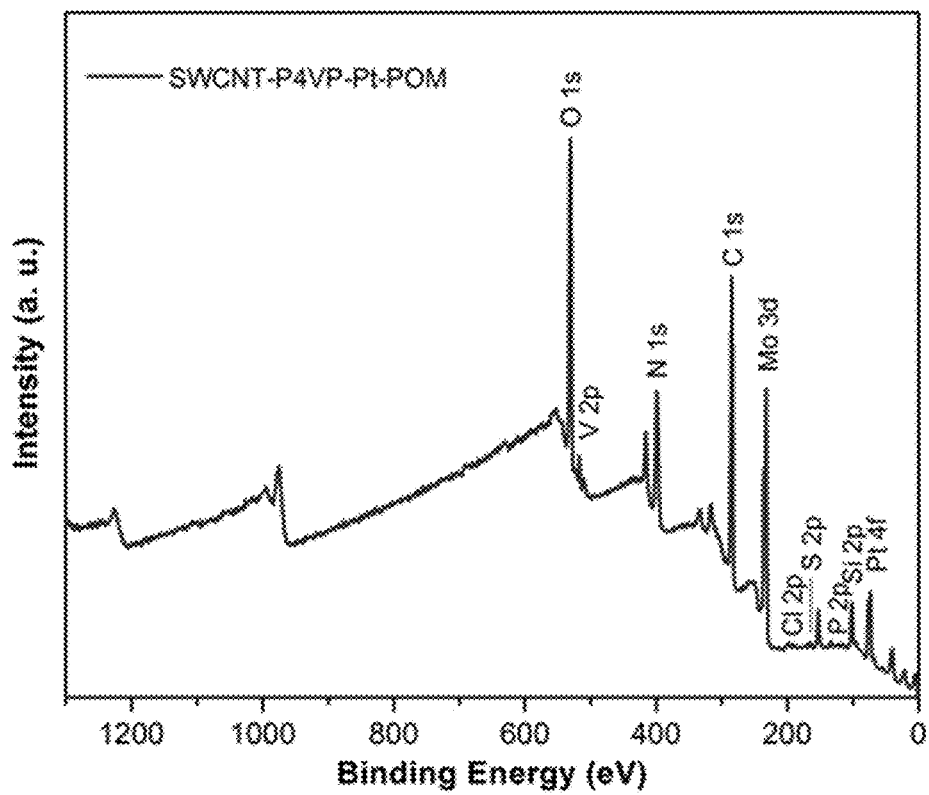
FIG. 8A-8G depict XPS spectra of a sensor.
Figure 8B:
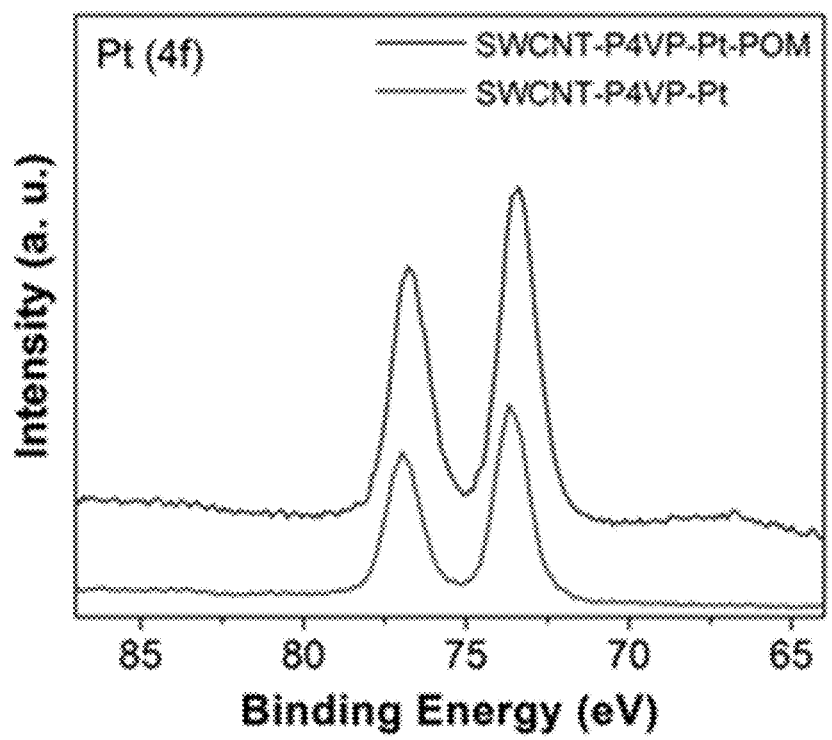
Figure 8C:
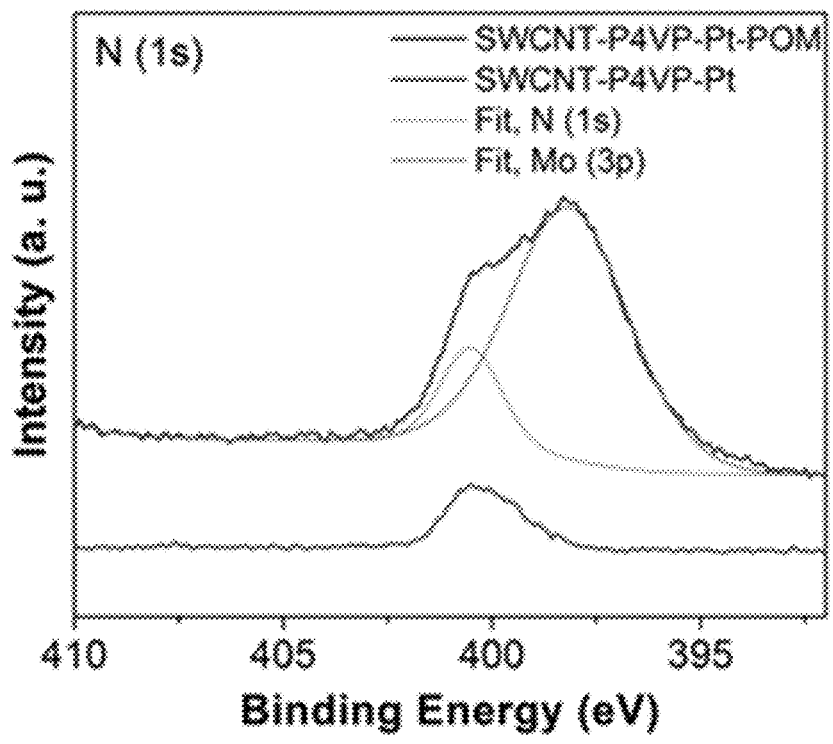
Figure 8D:
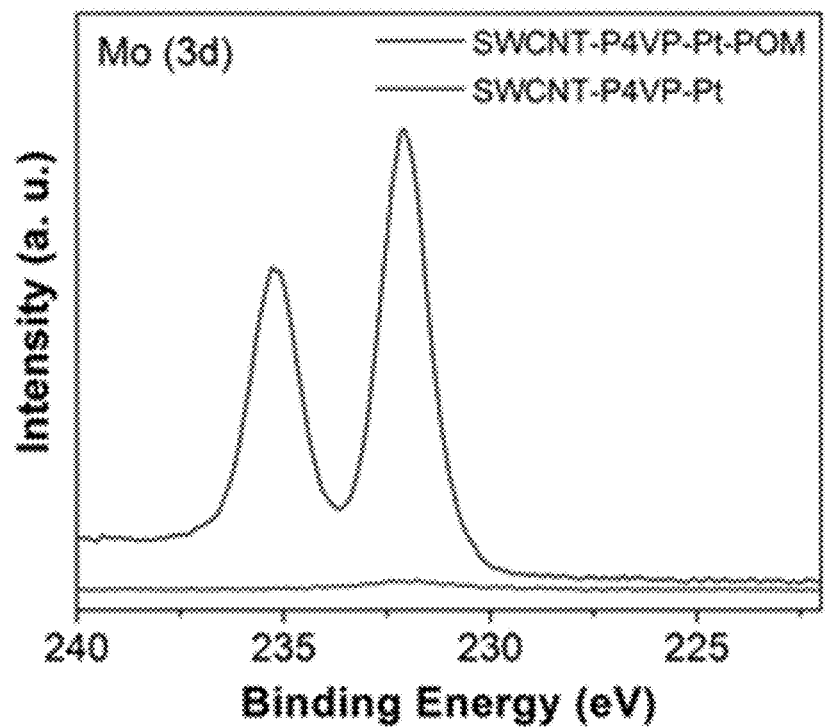
Figure 8E:
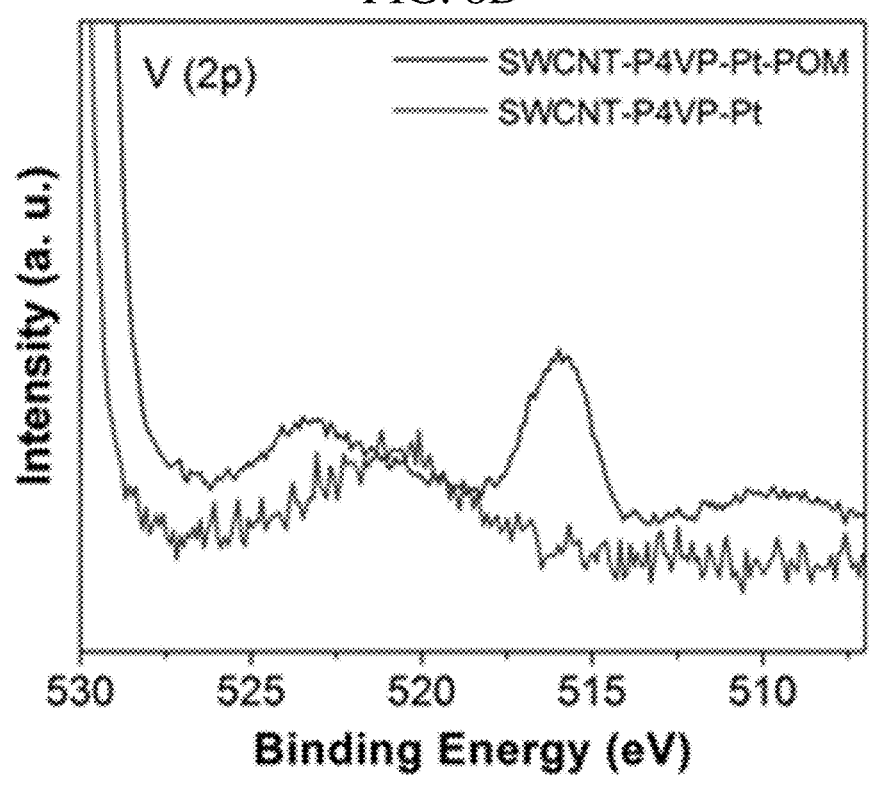
Figure 8F:
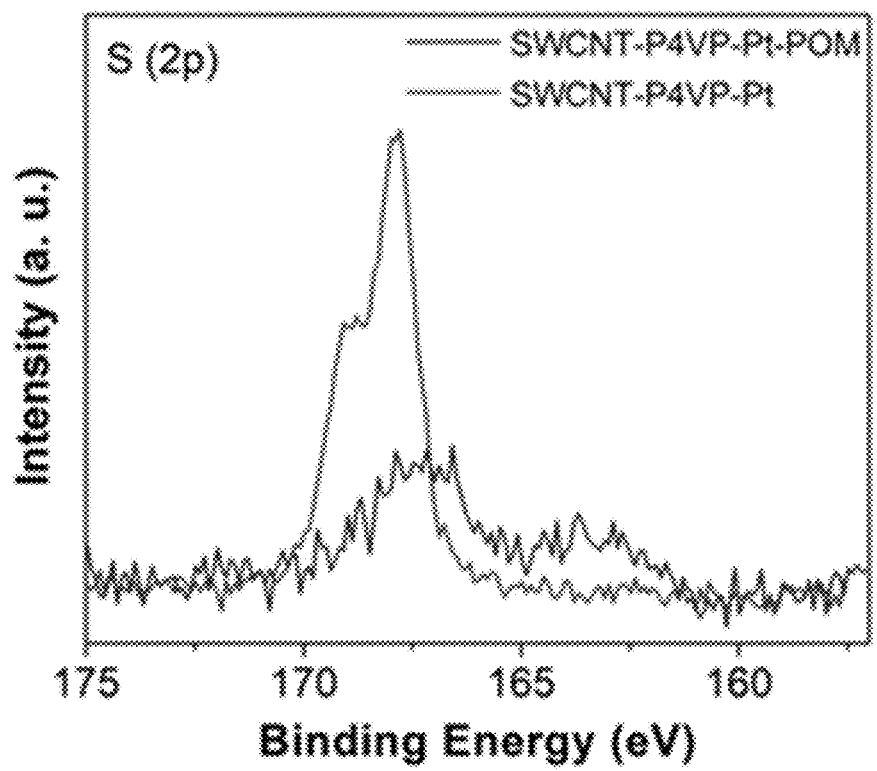
Figure 8G:
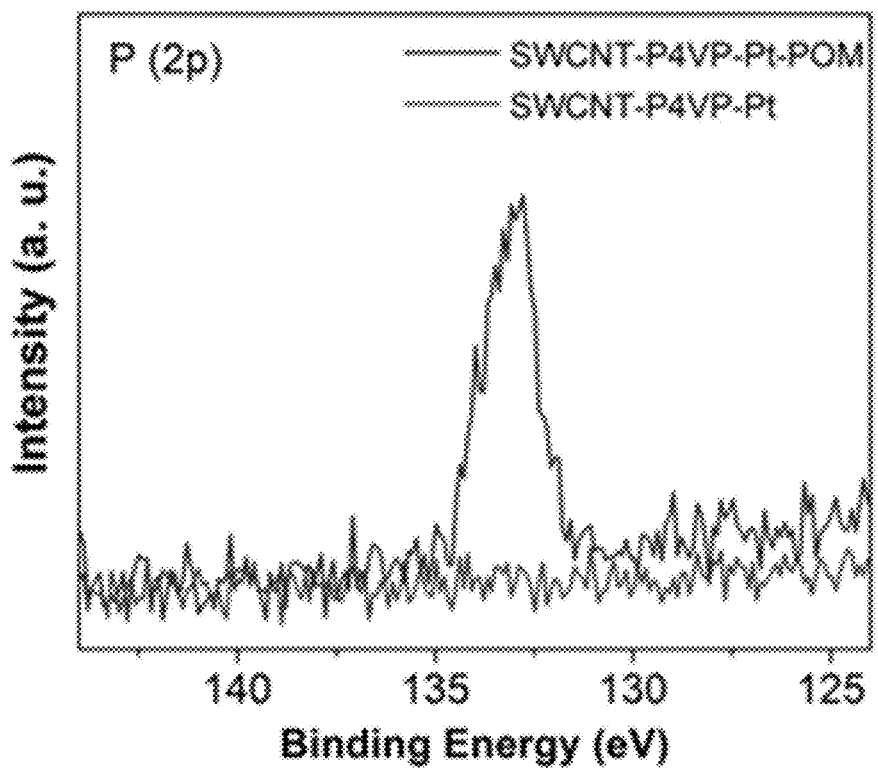

The composites SWCNT-P4VP, SWCNT-P4VP-Pt and SWCNT-P4VP-Pt-POM were characterized by Fourier transform infrared (FTIR) spectroscopy in order to probe surface immobilization chemistry and subsequent anion exchange (FIG. 7). The FTIR spectrum of a SWCNT-P4VP film exhibits diagnostic bands at 1597 and 1417 $cm^{-1}$ corresponding to free pyridyl ring vibrations. In SWCNT-P4VP-Pt, metal coordination was evidenced by the shifting of these bands to 1587 and 1413, respectively, while a new vibration was observed at 1220 $cm^{-1}$, attributed to the [$SO_4Me$]$^-$ anion. See, for example, Sigma-Aldrich FTIR documentation for "methyl sulfate sodium salt", which is incorporated by reference in its entirety. Upon treatment with [$H_5PV_2Mo_{10}O_{40}$], anion exchange in the SWCNT-P4VP-Pt-POM composite was confirmed by the disappearance of the band at 1220 $cm^{-1}$ while new bands appeared at 945 and 785 $cm^{-1}$ that correspond to the POM anion.

Metal incorporation as well as anion exchange in SWCNT-P4VP-Pt-POM was further probed by X-ray photoelectron spectroscopy (XPS; FIGS. 8A-8G). Diagnostic peaks corresponding to $Pt_{4f(5/2)}$ and $Pt_{4f(7/2)}$ binding energies were observed at 76.8 and 73.4 eV, respectively, supporting the incorporation of Pt(II) into the composite. Further, a high-resolution $N_{1s}$ scan revealed a broad peak at 400.5 eV in SWCNT-P4VP-Pt, indicating that the majority of nitrogen atoms in both P4VP as well as the bpym ligand exist in a coordinated, rather than free form upon addition of the Pt complex to SWCNT-P4VP. See, for example, B. Yoon, et al., *ACS Appl. Mater. Interfaces* 2018, 10, 33373-33379, which is incorporated by reference in its entirety. Finally, a marked decrease was observed for $S_{2p}$ binding energy (167.8 eV) in SWCNT-P4VP-Pt-POM compared to SWCNT-P4VP-Pt, while new peaks were observed that correspond to $Pe_p$, $V_{2p(1/2)}$, $V_{2p(3/2)}$ $MO_{3d(3/2)}$ and $MO_{3d(5/2)}$ binding energies at 132.8, 523.5, 516.0, 235.3 and 232.1 eV in SWCNT-P4VP-Pt-POM, respectively. Taken together, these XPS results confirm anion exchange and POM incorporation into the SWCNT-P4VP-Pt-POM composite.

Figure 9A:
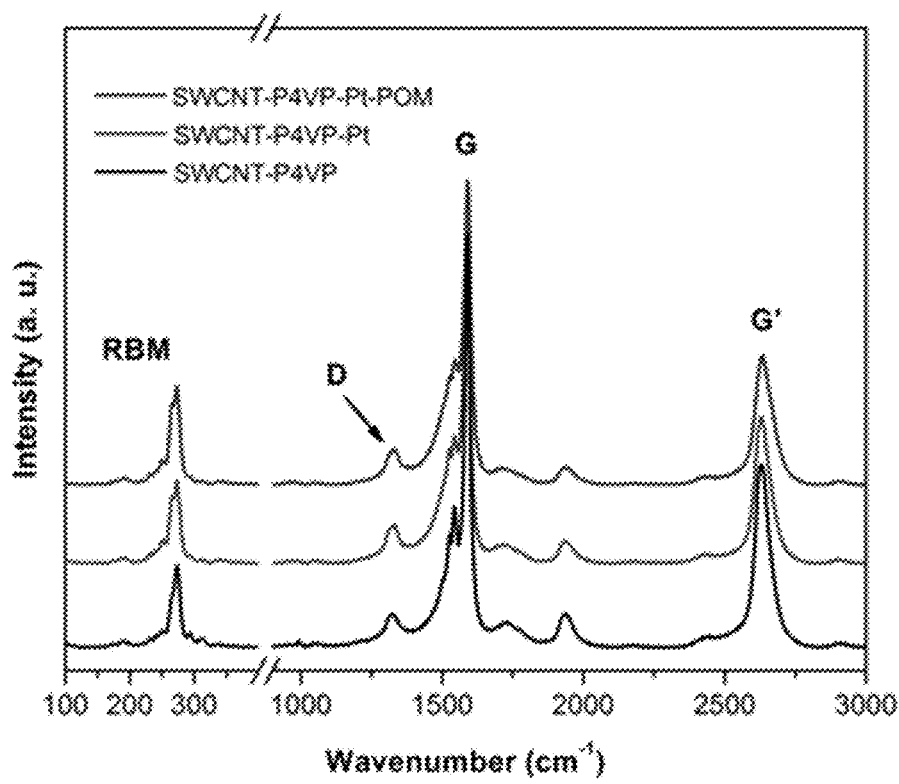
FIGS. 9A-9B depict Raman spectra of SWCNT-P4VP (black), SWCNT-P4VP-Pt (red) and SWCNT-P4VP-Pt-POM (blue) thin films on glass substrates (FIG. 9A) and Expanded view of D/G bands in the Raman spectra of SWCNT-P4VP, SWCNT-P4VP-Pt and SWCNT-P4VP-Pt-POM thin films on glass substrates (FIG. 9B).
Figure 9B:
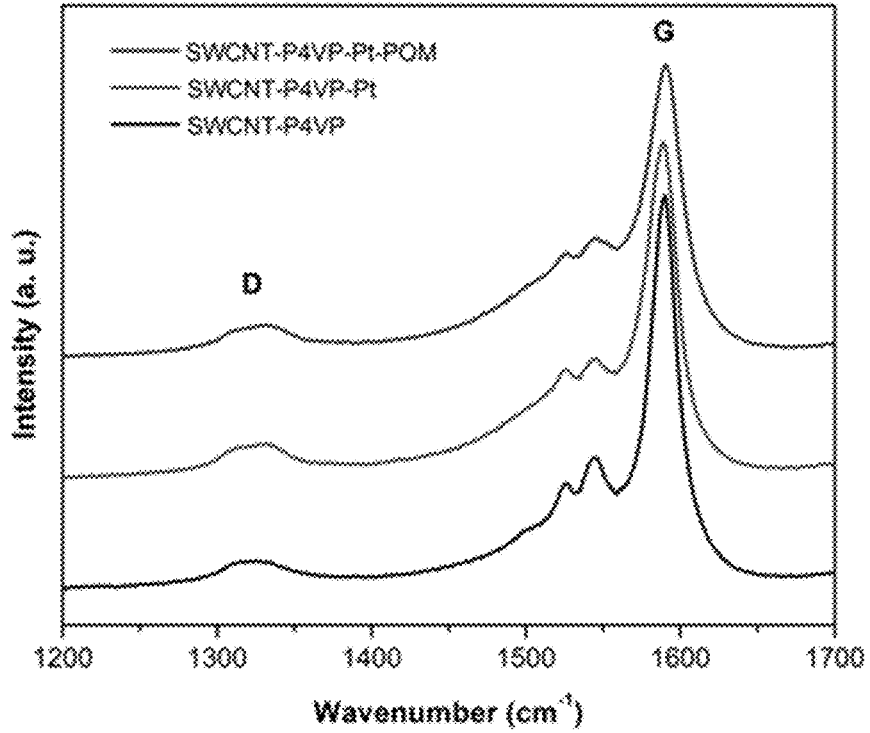

To probe whether the incorporation of Pt-POM disrupts the π-electronic states in the SWCNT network by nanotube wall modification, SWCNT-P4VP, SWCNT-P4VP-Pt and SWCNT-P4VP-Pt-POM films were also characterized by Raman spectroscopy (532 nm excitation; FIGS. 9A-9B). In particular, the D/G band ratio was of interest in each composite, wherein nanotube sidewall defects give rise to a diminished G-band that corresponds to $sp^2$ C—C stretching modes in graphitic materials. Importantly, the D/G ratios in SWCNT-P4VP, SWCNT-P4VP-Pt and SWCNT-P4VP-Pt-POM were virtually unchanged (D/G=0.2), indicating that the Pt-POM incorporation steps do not significantly affect the electronic structure of the SWCNTs.

Figure 4C:
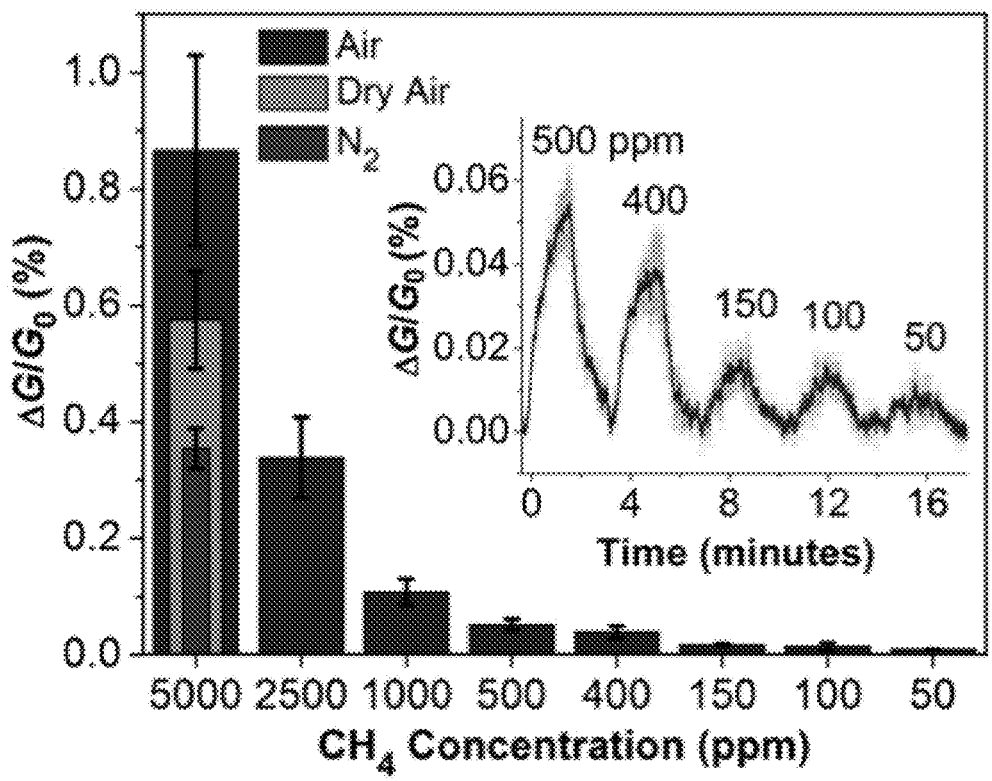
Figure 4D:
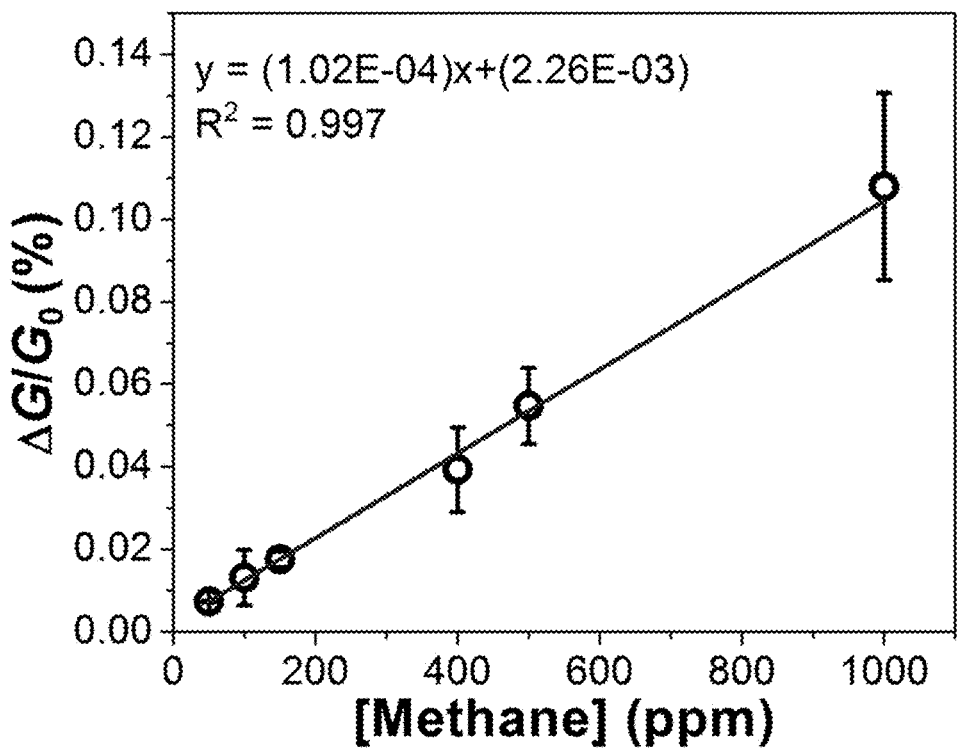
Figure 10A:
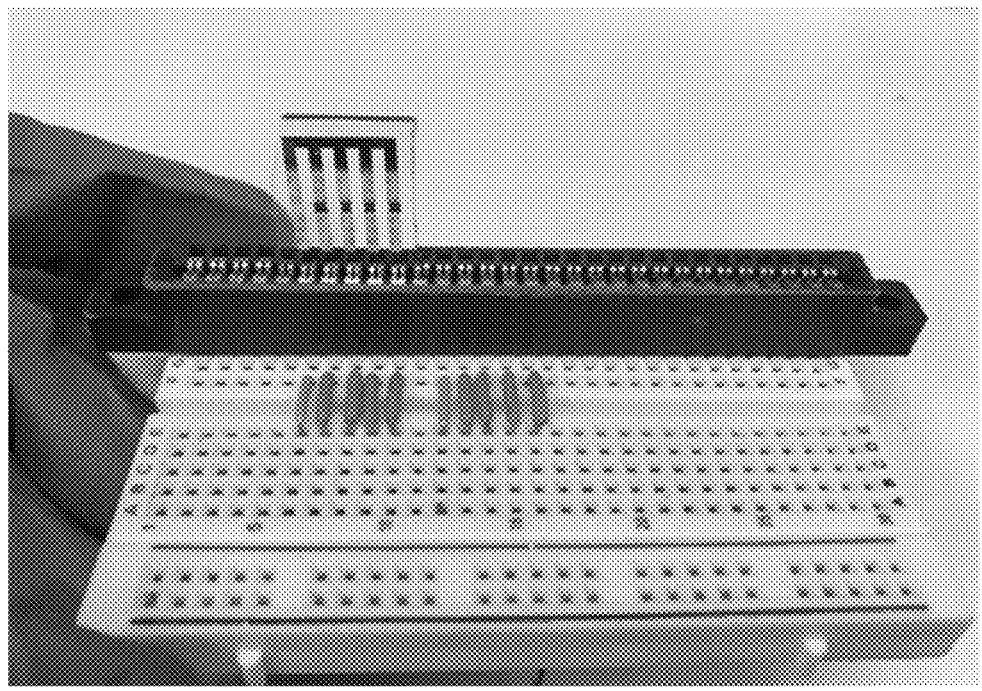
FIGS. 10A-10C Single chemiresistor device (4 channels) inserted into edge connector-breadboard platform. b) Gastight enclosure fitted on connector-breadboard platform. c) Electrical leads connecting the breadboard to a potentiostat for the collection of sensing data. In this configuration, 4 channels are monitored in parallel.

Having established the composition of SWCNT-P4VP-Pt-POM, the utility of the composite as a chemiresistor in $CH_4$ sensing was examined. The proof-of-concept sensing experiments were conducted in a gas-tight enclosure wherein two mass-flow controllers (MFCs) were utilized to deliver a mixture of $CH_4$ in air (RH=10±5%) at a flow rate of 1 L/min to the device (see FIGS. 10A-10C for sensing schematic). The sensor signal was taken as the normalized change in device conductance [$\Delta G/G_0$ (%)=(I–$I_0$)/$I_0$×100%; $I_0$=initial current] upon application of a voltage (0.1 V) between the electrodes. Exposing the device to 0.5% (5000 ppm) of $CH_4$ for 120 seconds at room temperature resulted in a significant sensor response corresponding to a 0.87±0.16% increase in device conductance. The sensor response was found to be reversible, wherein nearly full baseline recovery was observed after purging for 120 seconds with air. Importantly, a detrimental effect on sensor response was observed when each component of the SWCNT-P4VP-POM-Pt composite were omitted. For instance, a device fabricated with exclusion of P4VP yielded a negligible sensor response on the order of that observed for pristine SWCNTs, confirming that the pyridyl moiety is essential for anchoring the selector on the SWCNT surface. Further, while exclusion of the Pt cation resulted in a near-negligible sensor response, a device fabricated with the exclusion of POM (SWCNT-P4VP-Pt) showed a low-magnitude inverted response corresponding to a decrease in device conductance (–0.28±0.03%), likely due to a change in sensing mechanism (FIG. 4A). Overall, these experiments establish that P4VP, Pt cation, the POM anion, are key for the observed chemiresistive $CH_4$ sensing using SWCNT-P4VP-Pt-POM. Exposure of the sensor to varying $CH_4$ concentrations yielded a linear change in response in the range measured (5000-50 ppm), wherein the theoretical limit of detection (LOD; LOD=3×($rms_{noise}$)×$(slope)^{-1}$, wherein slope is the linear regression fit of the sensor response vs concentration curve) for 120 s of exposure was calculated to be 22 ppm (FIG. 4D).

Figure 11A:
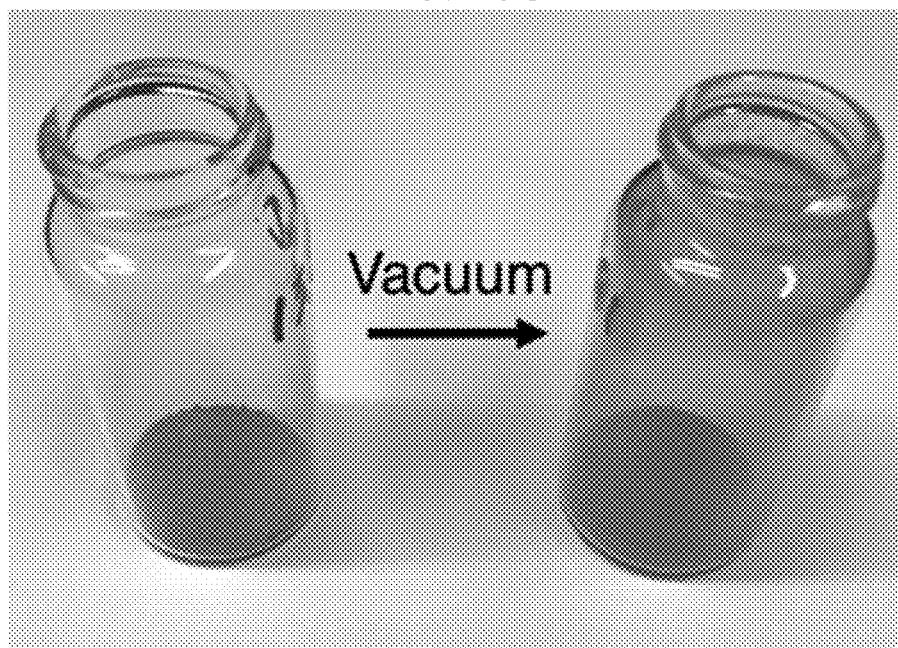
FIGS. 11A-11B depict freshly prepared $[H_5PV_2Mo_{10}O_{40}]\cdot 32H_2O$ sample before and after exposure to vacuum (5 h) (FIG. 11A) and chemiresistive response of a new SWCNT-P4VP-Pt-POM device compared with the response after exposure to vacuum (5 h) and the response of the same device immersed in water following exposure to vacuum (5 h) (FIG. 11B). In all cases, devices were exposed to 0.5% of $CH_4$ in air for 120 s at room temperature.
Figure 11B:
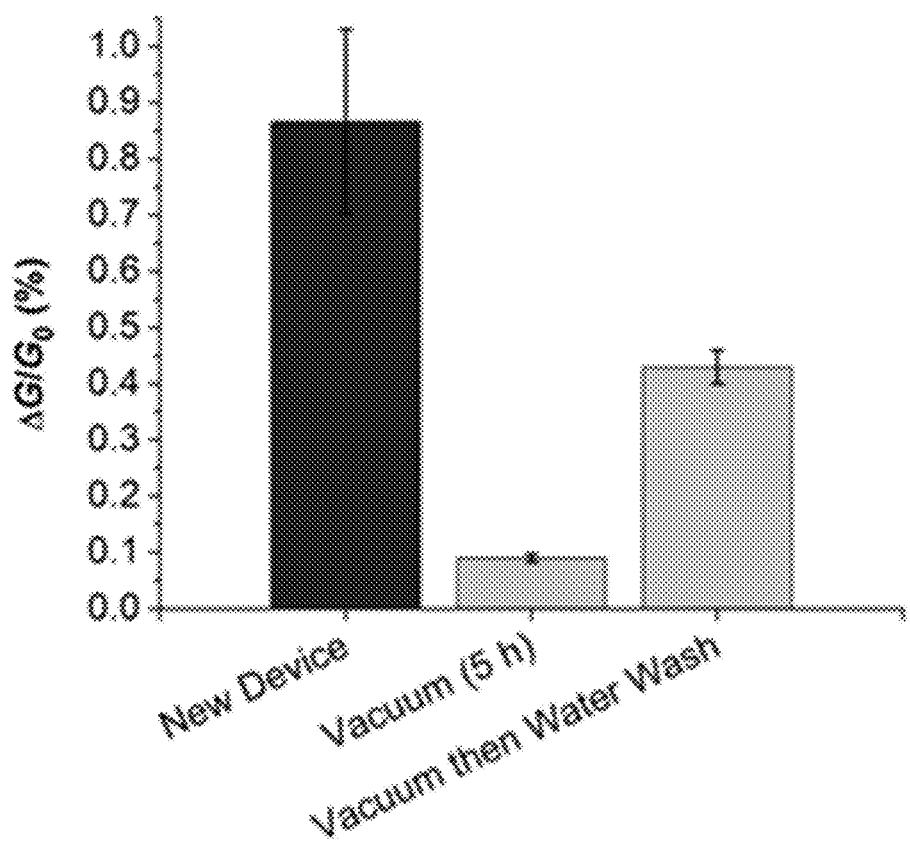

The reversible increase in device conductance observed when SWCNT-P4VP-Pt-POM was exposed to $CH_4$ is consistent with the working hypothesis that $CH_4$ oxidation should give rise to a signal. If a Shilov-type methane oxidation mechanism is operative, some platinum centers will transiently exist in a formal Pt(IV) oxidation state. See, for example, A. Labinger, J. E. Bercaw, Top. Organomet. Chem. 2011, 35, 29-59; and N. J. Gunsalus, et al. Chem. Rev. 2017, 117, 8521-8573, each of which is incorporated by reference in its entirety. Given that SWCNTs are known to undergo p-doping upon exposure to $O_2$ in air, interactions with the high-valent, electron-deficient metal centers will likely increase hole carrier density and thereby proportionally increase conductance. See, for example, P. G. Collins, et al., A. Zettl, Science 2000, 287, 1801-1804; and D. Kang, et al., Nanotechnology 2005, 16, 1048-1052, each of which is incorporated by reference in its entirety. Consistent with an oxidation event in SWCNT-P4VP-Pt-POM is the observation that use of dinitrogen in place of air as the analyte carrier gas significantly attenuated the magnitude of observed response but maintained its direction ($\Delta G/G_0$=0.35±0.03%; 5000 ppm $CH_4$, 120 s exposure; FIG. 4C). In addition, the presence of humidity was also found to be key for optimal sensor performance as indicated by a lower response to $CH_4$ when dry air (RH=0%) was used as the carrier gas ($\Delta G/G_0$=0.58±0.08%; 5000 ppm $CH_4$, 120 s exposure; FIG. 4C). The humidity effect was attribute to the proposed role of POM as an oxidant in enabling the key Pt(II)/(IV) oxidation. See, for example, I. Bar-Nahum, et al., J. Am. Chem. Soc. 2004, 126, 10236-10237; R. Neumann, Prog. Inorg. Chem. 1998, 47, 317-370; and R. Neumann, Inorg. Chem. 2010, 49, 3594-3601, each of which is incorporated by reference in its entirety. In this context, it is important to note that $[H_5PV_2Mo_{10}O_{40}]$ is a hydrate in the solid-state, containing 32 water equivalents/mol, wherein dehydration results in a noticeable color change of the compound from orange to yellow-brown (FIG. 11A) likely impacting its oxidation potential. See, for example, G. A. Tsigdinos, C. J. Hallada, Inorg. Chem. 1968, 7, 437-441, each of which is incorporated by reference in its entirety. Consistent with this qualitative observation, exposure of SWCNT-P4VP-Pt-POM vacuum for 5 hours resulted in a dramatically lowered $CH_4$ response of $\Delta G/G_0$=0.09±0.01% (5000 ppm $CH_4$, 120 s exposure, FIG. 11B). Interestingly, submerging the device in water and subsequent evaluation of its sensing performance resulted in partial recovery of the signal to $\Delta G/G_0$=0.43±0.03% (FIG. 11B), implying that the de-hydration process is partially reversible. Overall, these results are consistent with a $CH_4$ oxidation event by establishing the roles of $O_2$, $H_2O$ and POM structural integrity during sensing.

Figure 5:
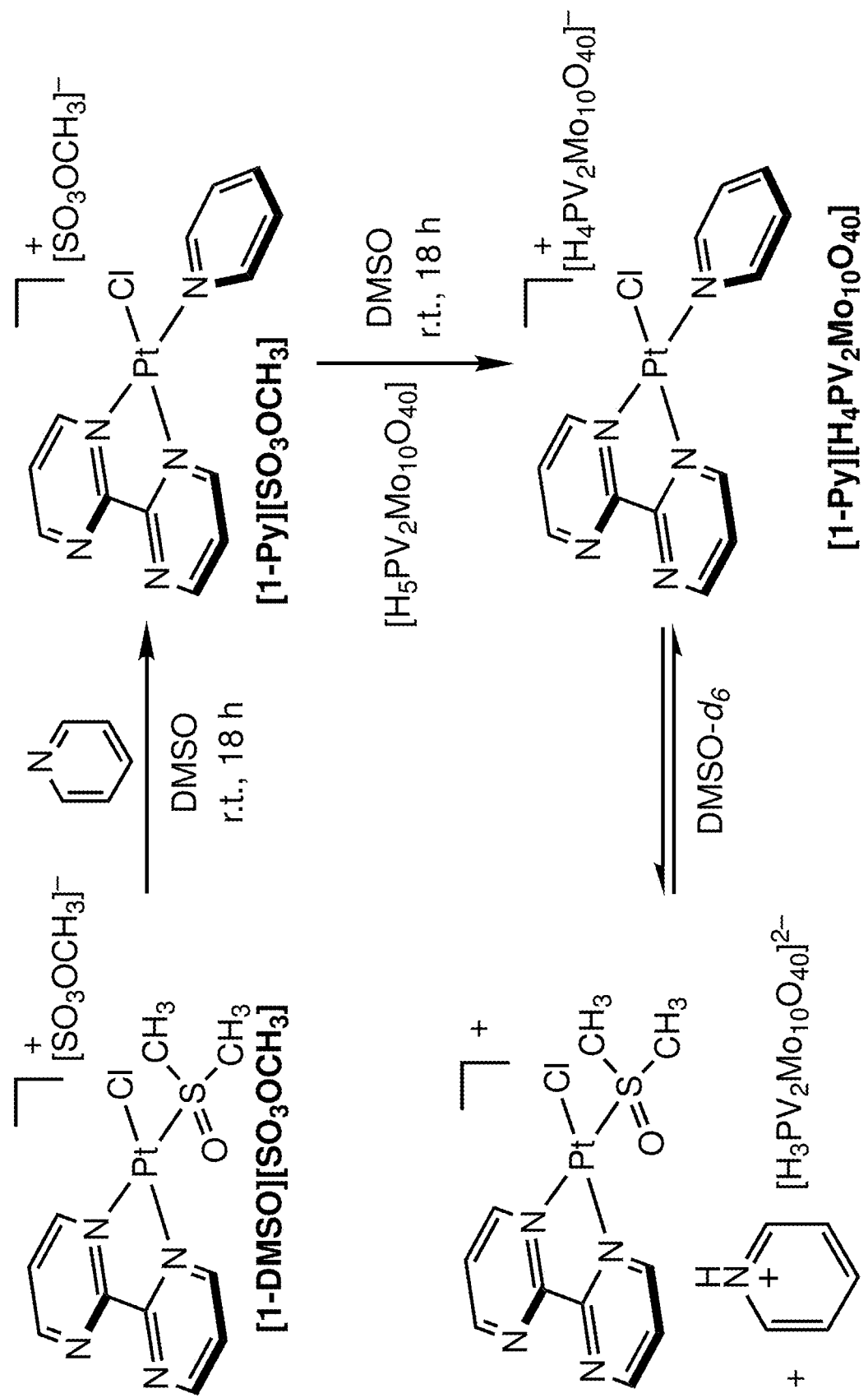
FIG. 5 depicts synthesis of $[1\text{-Py}][SO_3OCH_3]$ and subsequent reaction with $[H_5PV_2Mo_{10}O_{40}]$.

Pt speciation in the sensor composite was studied in order to further support the working hypothesis invoking a Pt-mediated $CH_4$ oxidation. To this end, a $^1H$ NMR study was performed with soluble Pt complexes and pyridine as a model for P4VP. Stirring a DMSO-$d_6$ solution of [1-DMSO][$SO_3OCH_3$] in the presence of one equivalent of pyridine at room temperature for 18 hours resulted in quantitative substitution of the DMSO ligand to afford the pyridine adduct [1-Py][$SO_3OCH_3$] (FIG. 5). The $^1H$ NMR spectrum of [1-Py][$SO_3OCH_3$] exhibits the number of resonances indicative of an overall $C_s$ molecular symmetry, with pyridine resonances observed at 8.92, 8.27 and 7.82 ppm, consistent with coordination to the platinum center. Also indicative of DMSO ligand substitution was the lack of a diagnostic DMSO vibration in the IR spectrum of [1-Py][$SO_3OCH_3$] ($V_{S=O}$=1128 $cm^{-1}$ in [1-DMSO][$SO_3OCH_3$]). These data demonstrate that the Pt complex is likely immobilized by the substitution of the DMSO ligand by P4VP in SWCNT-P4VP-Pt.

Figure 12:
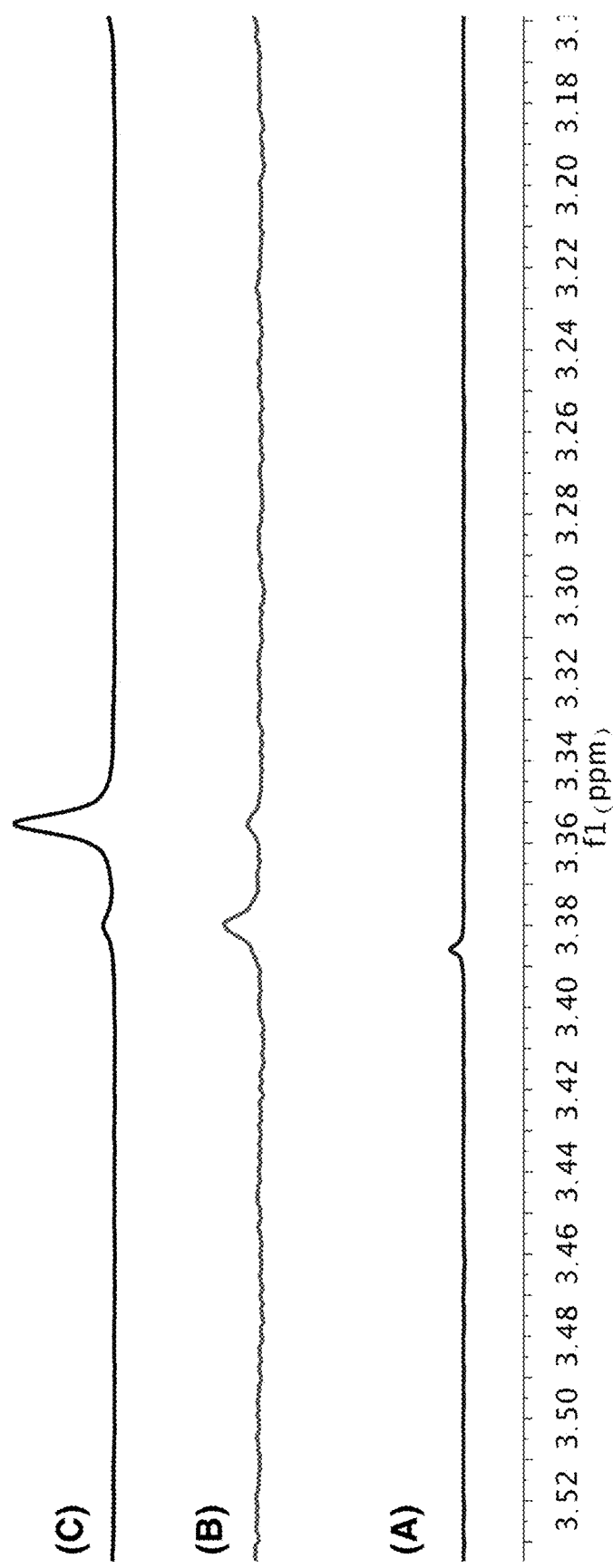
FIG. 12 depicts expanded $^1H$ NMR spectra corresponding to: Panel A: Reaction product of $[1\text{-Py}][SO_3OCH_3]+[H_5PV_2Mo_{10}O_{40}]$ in $D_2O$; Panel B: Reaction product of $[1\text{-Py}][SO_3OCH_3]+[H_5PV_2Mo_{10}O_{40}]$ stirred under an atmosphere of $CH_4$ for 30 minutes in $D_2O$; and Panel C: Authentic MeOH added to the sample depicted in Panel B. Spectra collected at 23° C.
Figure 14A:
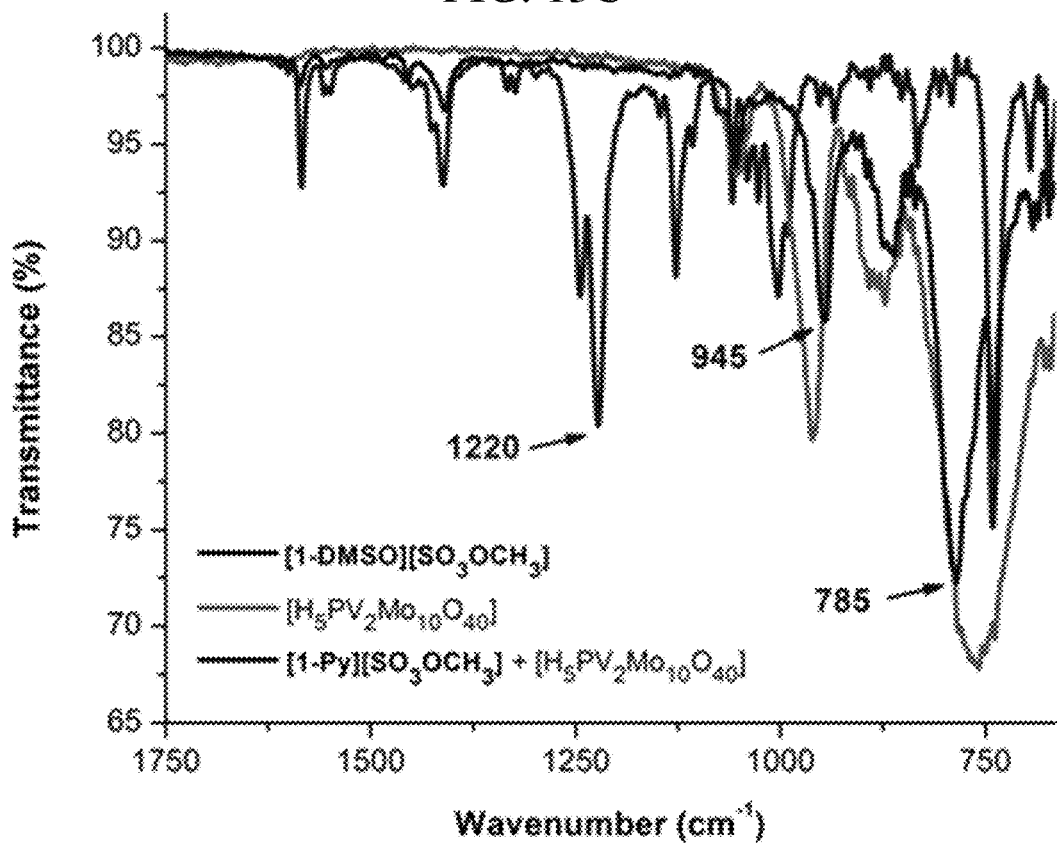
FIGS. 14A-14B depict ATR-FTIR spectra of [1-DMSO][$SO_3OCH_3$], [$H_5PV_2Mo_{10}O_{40}$] and the reaction between [1-Py][$SO_3OCH_3$] and [$H_5PV_2Mo_{10}O_{40}$] (FIG. 14A) and an expanded view of the C=N vibrational bands in the ATR-FTIR spectra of [1-DMSO][$SO_3OCH_3$], [$H_5PV_2Mo_{10}O_{40}$] and the reaction between [1-Py][$SO_3OCH_3$] and [$H_5PV_2Mo_{10}O_{40}$] (FIG. 14B).
Figure 14B:
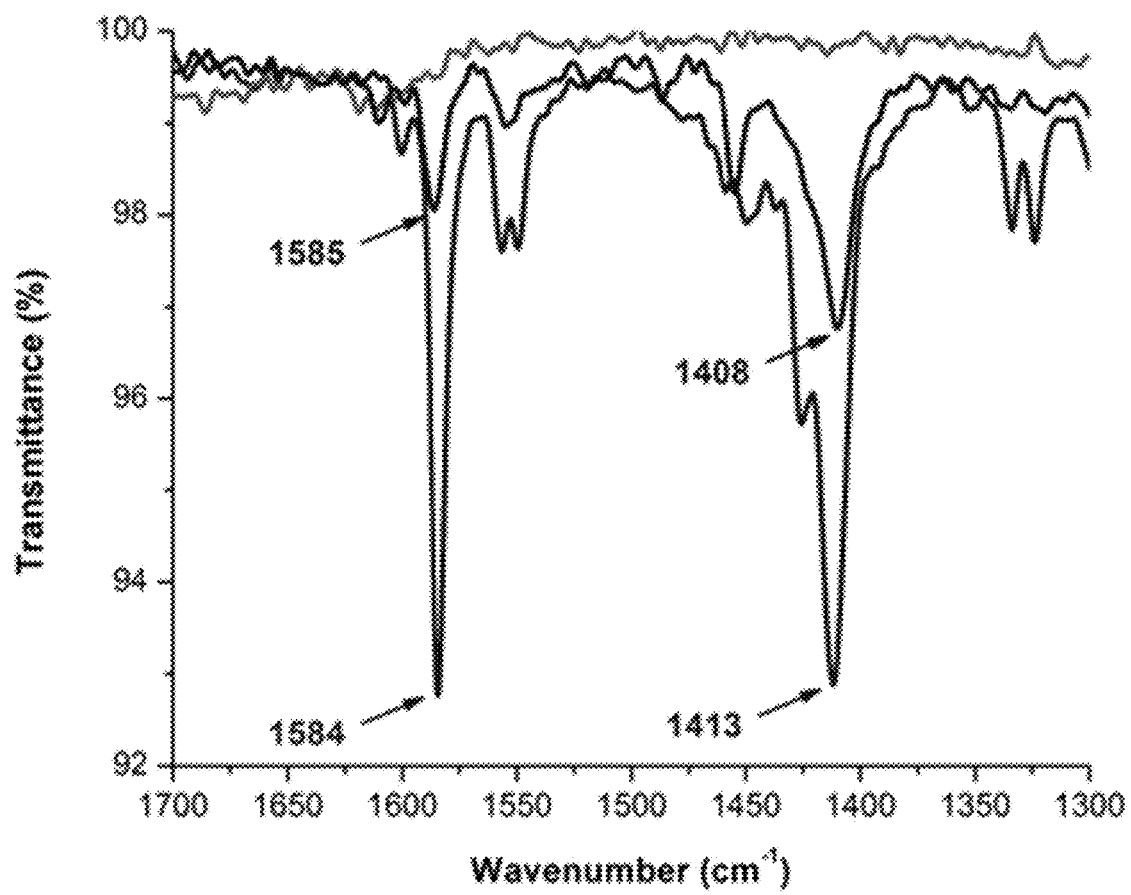

To examine the speciation of the Pt complex in SWCNT-P4VP-Pt-POM following the anion exchange with $[H_5PV_2Mo_{10}O_{40}]$, the solution-state reactivity of the POM acid with the model complex [1-Py][$SO_3OCH_3$] was next examined. Addition of $[H_5PV_2Mo_{10}O_{40}]$ load to a DMSO-$d_6$ solution containing [1-Py][$SO_3OCH_3$] initially resulted in anion exchange to furnish [1-Py][$H_4PV_2Mo_{10}O_{40}$]. However, monitoring the DMSO-$d_6$ solution of [1-Py][$H_4PV_2Mo_{10}O_{40}$] by $^1H$ NMR spectroscopy over the course of for 18 hours at room temperature revealed that the polyoxometalate anion partially protonates the coordinated pyridine to yield an equilibrium mixture of products containing the starting [1-Py][$H_4PV_2Mo_{10}O_{40}$] complex, as well as [1-DMSO]$^+$, and pyridinium (FIG. 5). These results indicate that the speciation of SWCNT-P4VP-Pt-POM is likely best described as containing protonated pyridyl groups, in addition to P4VP- and DMSO-ligated cationic platinum bipyrimidine complexes that are immobilized by P4VP coordination and electrostatic attraction to POM anions, respectively (FIGS. 3A-3C). A solid-state IR spectrum of the isolated equilibrium mixture containing [1-Py][$H_4PV_2Mo_{10}O_{40}$] and [1-DMSO][Py-H][$H_3PV_2Mo_{10}O_{40}$] exhibited diagnostic peaks that matched those observed for the SWCNT-P4VP-Pt-POM film (FIGS. 14A-14B), validating the relevance of the model system to the chemiresistor surface composition. Importantly, these model studies demonstrate that the known $CH_4$ oxidation precatalyst [1-DMSO][$H_4PV_2Mo_{10}O_{40}$] is present on the chemiresistor surface and likely provides a facile entry point to $CH_4$ oxidation. Indeed, stirring a $D_2O$ slurry of the isolated equilibrium mixture containing [1-Py][$H_4PV_2Mo_{10}O_{40}$], [1-DMSO]$^+$, and pyridinium under an atmosphere of $CH_4$ furnished $CH_3O(H/D)$ as observed by $^1H$ NMR spectroscopy (FIG. 12). It is important to note that for the purposes of chemiresistive $CH_4$ sensing, C—H oxidation need not proceed with high yield and/or selectivity. Given that $CH_4$ oxidation using [1-DMSO][$SO_3OCH_3$]/[$H_5PV_2Mo_{10}O_{40}$] was reported to proceed at 50° C., oxidation product yields at room temperature on the timescale of the sensing experiments are likely not synthetically relevant.

Figure 6A:
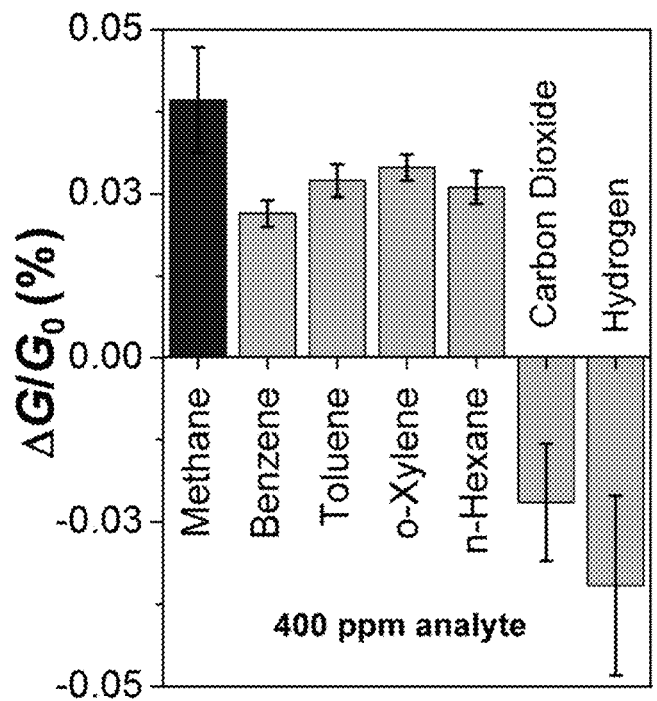
FIGS. 6A-6B depict response of a sensor.

Having examined the chemiresistive response of SWCNT-P4VP-Pt-POM to $CH_4$ and its origin, the selectivity and stability of the device was tested. Accordingly, the response of SWCNT-P4VP-Pt-POM upon exposure to representative hydrocarbon contaminants likely to be found in a $CH_4$ stream were tested. The results are shown in FIG. 6A and demonstrate that SWCNT-P4VP-Pt-POM exhibits selectivity for $CH_4$ over hexanes as well as benzene/toluene/o-xylene (BTX). These results are particularly surprising in that higher boiling analytes tend to partition to sensors more effectively and typically give rise to a significantly larger responses when compared to volatile $CH_4$ by traditional sensing mechanisms such as swelling. See, for example, P. C. Jurs, G. A. Bakken, H. E. McClelland, Chem. Rev. 2000, 100, 2649-2678; (b) C. M. Hangarter, N. Chartuprayoon, S. C. Hernandez, Y. Choa, N. V. Myung, Nano Today 2013, 8, 39-55, each of which is incorporated by reference in its entirety. While the mild selectivity observed for $CH_4$ appears to be a unique feature of SWCNT-P4VP-Pt-POM, the observation of a sensor response to n-hexane as well as BTX are qualitatively consistent with the proposed sensing mechanism, as Shilov-type oxidation precatalysts are expected to engage both aliphatic as well as aromatic hydrocarbons. See, for example, M. Lersch, M. Tilset, *Chem. Rev.* 2005, 105, 2471-2526, each of which is incorporated by reference in its entirety.

In addition to heavier hydrocarbons, the response of SWCNT-P4VP-Pt-POM to interferent gases commonly found in processed $CH_4$ streams was also examined. Specifically, SWCNT-P4VP-Pt-POM was found to exhibit selectivity for $CH_4$ over carbon dioxide ($CO_2$) as well as hydrogen ($H_2$). Upon exposure to these gases, a decrease in device conductance was observed that points to n-type doping, opposite of the p-type sensor response to $CH_4$ (FIG. 6A). The observed reversal in response likely indicates a mechanistic pivot for the non-hydrocarbon analytes and provides a diagnostic detection handle for differentiating $CH_4$ from $CO_2$ and $H_2$ using SWCNT-P4VP-Pt-POM.

Figure 6B:
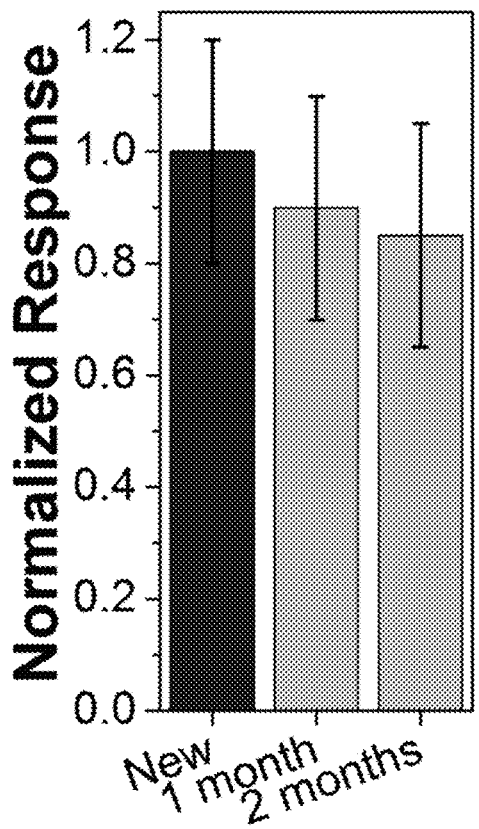

Importantly, the device showed excellent stability over time with minimal decrease in $CH_4$ response after storage on a laboratory bench for 2 months, a consequence of its robust, air-stable components (FIG. 6B).

Figure 13A:
FIGS. 13A-13C depict multimeter and mass flow controller (MFC) readings.
Figure 13B:
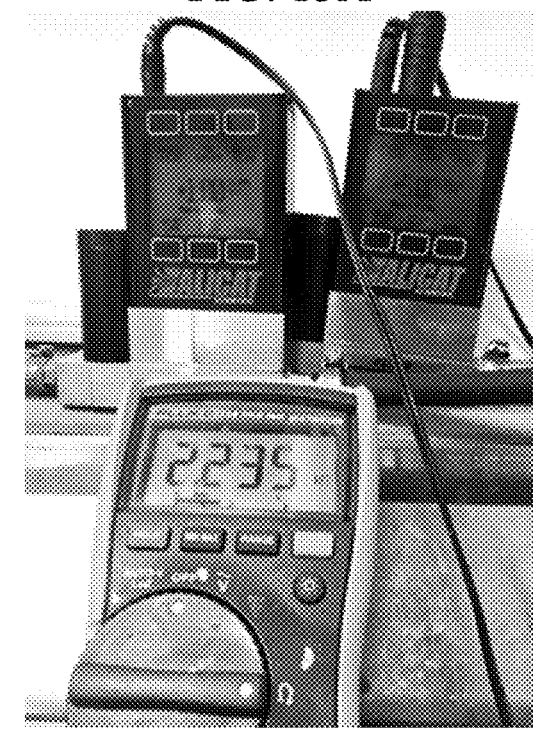
Figure 13C:

To evaluate the potential utility of the sensor outside of a laboratory setting, its $CH_4$ sensing performance was tested using a simple handheld multimeter. In this experiment, the multimeter was connected with leads directly to the sensing chamber and monitored the resistance readout. Using a device that was previously stored on the laboratory benchtop for 2 months, a resistance change from 2.250 kΩ to 2.235 kΩ was observed upon exposure to 5000 ppm of $CH_4$ in air for 120 s at room temperature, corresponding to a 0.67% increase in device conductance (FIGS. 13A-13C). This result highlights that costly analytical equipment is not needed to obtain a diagnostic $CH_4$ response using SWCNT-P4VP-Pt-POM.

In summary, a chemiresistive $CH_4$ sensor was fabricated from SWCNT-P4VP composites incorporating a platinum-polyoxometalate-based $CH_4$ oxidation precatalyst. The chemiresistor operates at room temperature in air, offers ppm-level sensitivity for $CH_4$ as well as selectivity over heavier hydrocarbons. The devices can be used in conjunction with a handheld multimeter, highlighting the potential of the method for the rapid, inexpensive and portable detection of $CH_4$.

Evaluation of composites incorporating other C—H oxidation precatalysts for $CH_4$ detection can be used Immobilization of a methane oxidation catalyst on the surface of a semiconducting material, in this case single-walled carbon nanotubes (SWCNTs). During methane oxidation, catalyst will cycle between different oxidation states that may include electron-poor intermediates (ie. Pt(IV)) that may inject charge carriers into SWCNT and thereby give rise to an increased device conductance. Other catalysts may cycle through electron-rich intermediates that may compensate charge carriers and give rise to a decreased conductance. In both cases, changes in device conductance (whether positive or negative) will serve as the sensor response.

Key to this approach is identification of methane oxidation catalysts that function at low temperature (approx. 50° C. or below) and incorporation into SWCNT-based composite. The work described herein has shown the viability of this approach for low-temperature methane sensing using a proof-of-concept platinum-polyoxometallate catalytic system. Other catalytic systems for low-temperature methane oxidation can also provide sensory responses such as those detailed in Table 1. These systems are attractive because they have been previously shown to undergo low-temperature methane oxidation in solution, and it is our goal to repurpose these catalysts as sensors. In Table 1, more active catalysts (having high turnover numbers) are expected to yield better sensors.

TABLE 1

List of targeted homogeneous catalysts for low-temperature methane oxidation and performance in catalysis.

| Catalyst | Temp (K) | Pressure (bar) | Turnover frequency ($h^{-1}$) | Turnover number | Reference |
|---|---|---|---|---|---|
| $EuCl_3$ | 298 | 10 | 4 | 4 | [1] |
| | 298 | 16 | 5.3 | 5.3 | [1] |
| | 298 | 1 | 1.6 | 1.6 | [1] |
| | 323 | 10 | 5.3 | 5.3 | [1] |
| $Eu(CH_3CO_2)_3$ | 298 | 10 | 4 | 4 | [1] |
| $Eu_2(CO_3)_3$ | 298 | 10 | 3 | 3 | [1] |
| $Eu_2(NO_3)_3$ | 298 | 10 | 2.8 | 2.8 | [1] |
| $[NBu_4]VO_3$-PCA-$H_2O_2$ | 296 | 75 | 7.3 | 176 | [2] |
| $VO(acac)_2$ | 353 | 50 | 0.8 | 18.5 | [3] |
| $VOF_3, (CF_3CO)_2O$ | 353 | 50 | 1.3 | 30.9 | [3] |
| $V_2O_5, (CF_3CO)_2O$ | 353 | 50 | 2.3 | 55.6 | [3] |
| $Pd(OAc)_2$ | 353 | 20 | 0.2 | 3.8 | [4] |
| $RhCl_3$ | 353 | 69 | 3 | 232 | [5] |
| $CoCl_2$ | 363 | 30 | 5.6 | 5.6 | [6] |
| $OsCl_3$ | 363 | 30 | 12 | 12 | [6] |
| $FeCl_3$ | 363 | 30 | 7.2 | 7.2 | [6] |
| $CuCl_2$ | 363 | 30 | 4.7 | 4.7 | [6] |
| $[(n-Bu)_4N]_4[W_{10}O_{32}]$, UV light | N/A | N/A | N/A | N/A | [7] |

PCA = pyrazine-2-carboxylic acid;
acac = acetylacetonate ($[CH_3COCHCOCH_3]^-$);
OAc = acetate ($[CH_3CO_2]^-$).
References (each reference is incorporated by reference in its entirety)
[1] I. Yamanaka, M. Soma, K. Otsuka, *J. Chem. Soc. Chem. Commun.* 1995, 2235.
[2] G. V. Nizova, G. Sgss-Fink, G. B. Shul'pin, *Chem. Commun.* 1997, 397.
[3] Y. Seki, J. S. Min, M. Misono, N. Mizuno, *J. Phys. Chem. B* 2000, 104, 5940.
[4] M. Muehlhofer, T. Strassner, W. A. Herrmann, *Angew. Chem. Int. Ed.* 2002, 41, 1745.
[5] M. Lin, T. E. Hogan, A. Sen, *J. Am. Chem. Soc.* 1996, 118, 4574.
[6] Q. Yuan, W. Deng, Q. Zhang, Y. Wang, *Adv. Synth. Catal.* 2007, 349, 1199.
[7] M. D. Tzirakis, I. N. Lykakis, M. Orfanopoulos, *Chem. Soc. Rev.* 2009, 38, 2609.

The general workflow will involve positioning the catalysts proximate to the semiconductor by physical deposition or by selected binding. For example by coordination to poly(4-vinylpyridine; P4VP)-SWCNT dispersions. The catalysts shown in Table 1 may produce superior sensors when paired with an oxidation enhancer. For example, polyoxometalate acids such as $[H_5PV_2Mo_{10}O_{40}]$ could enhance methane sensing performance. In addition to known methane oxidation catalysts, the methane sensing activity of polyoxometallates such as $(n-Bu)_4[W_{10}O_{32}]$ under UV irradiation is also possible, as these compounds are known to oxidize heavier hydrocarbons such as cyclohexane. Photoactivation of materials can result in enhanced reactivity and the application of light can be in principle used to enhance or even enable many of the catalytic compositions imagined. This effect is particularly well suited to metal oxides, but the oxidation activity of metal ligand combinations can be enhanced by light absorption and this can be translated into superior sensor responses.

In another example, a sensor directed to the detection of hydrogen sulfide can be prepared.

In this example, the fabrication of chemiresistors containing a series of POMs, $H_{(3+n)}[PV_nMo_{(12-n)}O_{40}]$ (n=1-4) was undertaken. This POM series was targeted because the degree of vanadium content influences oxidation reactivity and can be readily tuned. See, for example, A. M. Khenkin, R. Neumann, *J. Organomet. Chem.* 2015, 793, 134-138; G. A. Tsigdinos, C. J. Hallada, *Inorg. Chem.* 1968, 7, 437-441; and V. F. Odyakov, E. G. Zhizhina, *React. Kinet. Catal. Lett.*

2008, 95, 21-28, each of which is incorporated by reference in its entirety. The chemiresistive sensing platform utilized in the investigation described herein is based on SWCNTs noncovalently functionalized with poly(4-vinylpyridine) (SWCNT-P4VP). Here, the P4VP serves to de-bundle SWCNTs and thereby increases their analyte-accessible surface areas and restricts conduction pathways while also providing pyridyl "anchors" for immobilization of metal selectors by coordination. See, for example, J. H. Rouse, Langmuir 2005, 21, 1055-1061, which is incorporated by reference in its entirety. A uniformly dispersed SWCNT-P4VP films between Au electrodes (0.5 mm gap, Cr adhesive layer) was introduced on the surface of glass substrates according to previously described spray-coating procedures. See, for example, B. Yoon, et al., Chem. Mater. 2016, 28, 5916-5924, which is incorporated by reference in its entirety. A typical device contained four SWCNT-P4VP chemiresistor channels in parallel sharing a common counter electrode as described herein wherein the spray-coating was optimized out to achieve a 1-5 k$\Omega$ resistance across each channel. Subsequent soaking of the device in a DMSO solution (8 mM) of the complex Pt at room temperature for 18 hours achieved cation immobilization by coordination (as described herein) while subsequent soaking in DMSO solutions (8 mM) of the POMs $H_4[PVMo_{11}O_{40}]$ (POM1), $H_5[PV_2Mo_{10}O_{40}]$ (POM2), $H_6[PV_3Mo_9O_{40}]$ (POM3) and $H_7[PV_4Mo_8O_{40}]$ (POM4) at room temperature for 18 hours resulted in anion exchange and fabrication of the targeted chemiresistor series. While IR and X-ray photoelectron spectroscopy (XPS) showed successful Pt-POM incorporation into each composite, increasing vanadium content across the series as probed by XPS was found to be in good agreement with the values predicted by the molecular formulae of the POMs 1-4.

The chemiresistor series containing Keggin POMs $H_{(3+n)}[PV_nMo_{(12-n)}O_{40}]$ (n=1-4) in $H_2S$ sensing was evaluated (Devices 1-4, respectively). In a typical experiment, the chemiresistors were fitted in a gas-tight enclosure and exposed to $H_2S$ diluted with air as the carrier gas at a constant flow rate of 1 L min$^{-1}$. A bias voltage was then applied across the electrodes and the resulting current was recorded. The sensor responses are given as normalized changes in device conductance [$\Delta G/G_0$ (%)=(I-I$_0$)/I$_0$×100%; I$_0$=initial current] averaged across four devices and reported with standard deviations. As shown in FIGS. 24A-24B, devices 1-4 were found to exhibit an increase in conductance upon 60 seconds of exposure to 10 ppm of $H_2S$ in air at room temperature. Notably, the response times were rapid and reversible with swift baseline recovery observed upon purging with air. Interestingly, an increasing trend in response magnitude was observed with increased vanadium content in the constituent POMs wherein devices 1-3 exhibited responses of $\Delta G/G_0$=0.17±0.12%, 0.79±0.19% and 1.6±0.11%, respectively. By contrast, a lowered response of $\Delta G/G_0$=1.0±0.11% was observed for the highest vanadium containing POM4. This trend correlates with the effect of increased vanadium substitution in Keggin POMs, wherein introduction of V(V) atoms yields more reactive but less stable POMs. See, for example, I. A. Weinstock, et al., Chem. Rev. 2018, 118, 2680-2717, which is incorporated by reference in its entirety. The data suggests that for this system and detecting hydrogen sulfide, the ideal balance between POM oxidation reactivity and stability in the context of $H_2S$ detection is achieved with POM3. The consequences of POM stability on long-term device performance are discussed to a greater extent below.

Figure 25A:
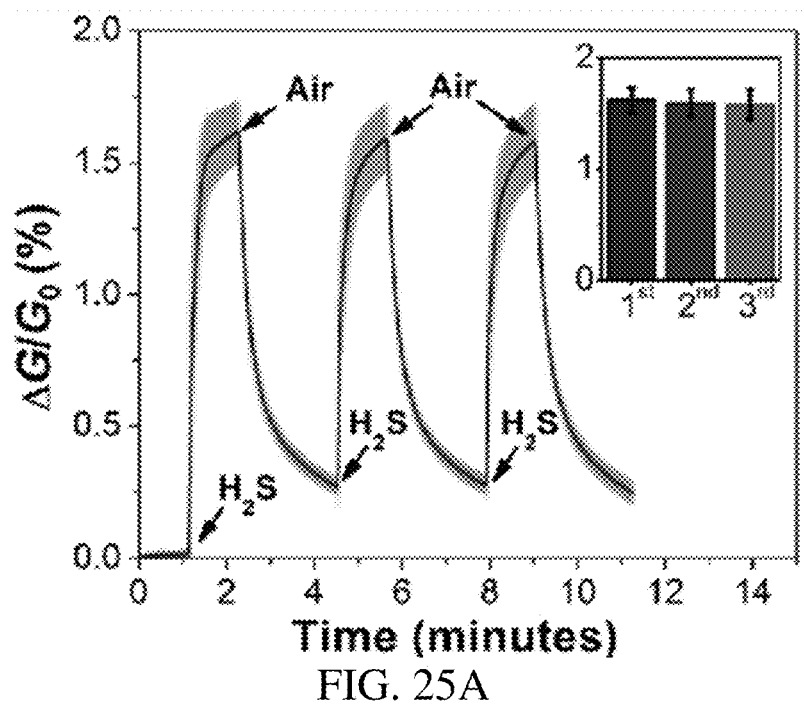
FIG. 25A depicts a graph showing averaged conductance trace of SWCNT-P4VP-Pt-POM3 in response to three repeated 1 min exposures of 10 ppm of $H_2S$ each.
Figure 25B:
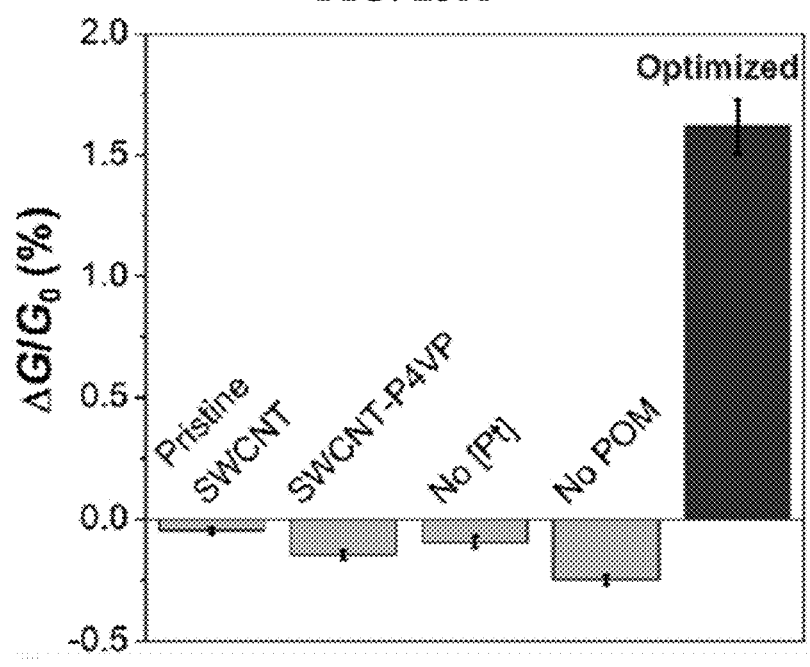
FIG. 25B depicts a graph showing control $H_2S$ sensing experiments omitting selector components compared with the sensing response of SWCNT-P4VP-Pt-POM3 to a 1 min exposure of 10 ppm of $H_2S$.
Figure 25C:
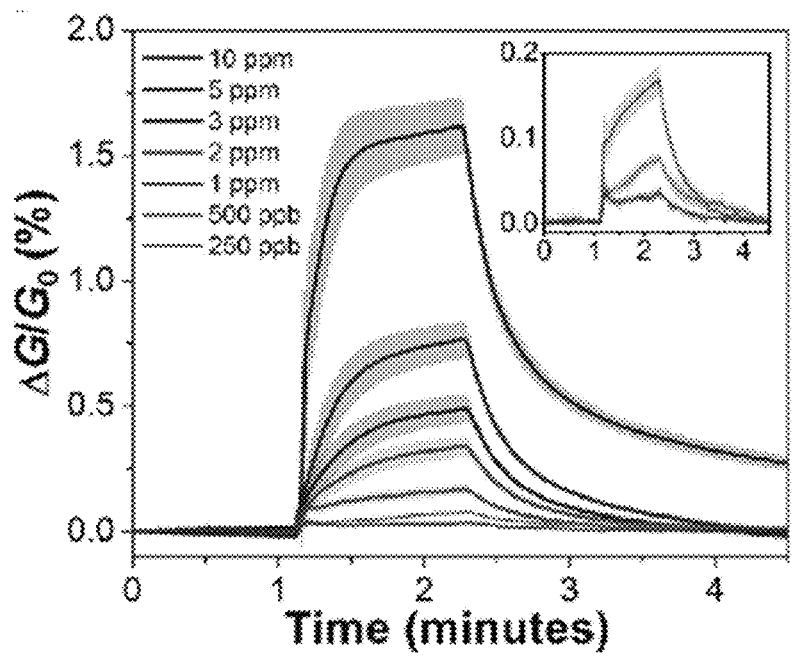
FIG. 25C depicts a graph showing averaged conductance traces of SWCNT-P4VP-Pt-POM3 in response to 1 min exposures of varying $H_2S$ concentrations.
Figure 25D:
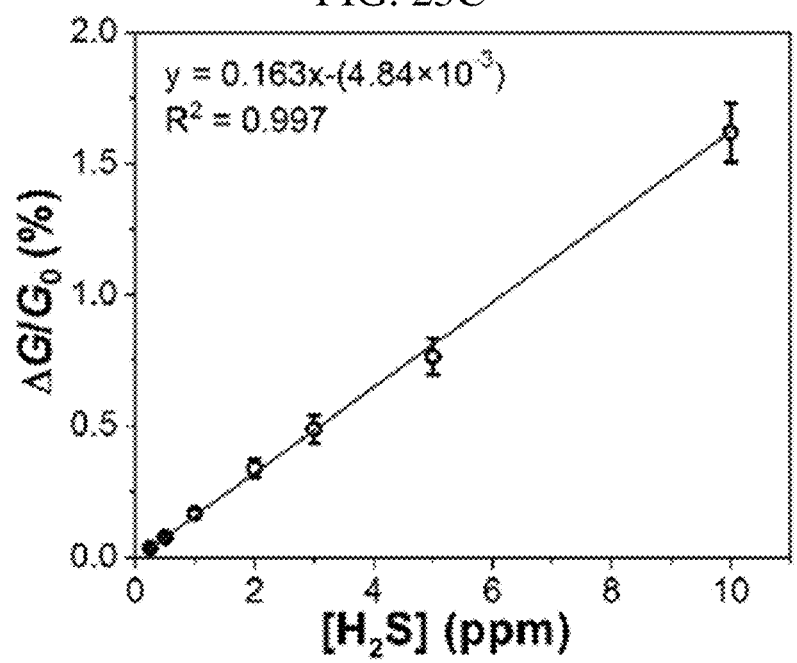
FIG. 25D depicts a graph showing chemiresistive responses of SWCNT-P4VP-Pt-POM3 to 1 min $H_2S$ exposures of varying concentration. Shaded areas and error bars represent standard deviations (N=4), all data were collected at room temperature in air.

Having identified the optimal POM for $H_2S$ sensing, the chemiresistive sensing performance of device SWCNT-P4VP-Pt-POM3 was used to further probed. Repeatedly exposing the sensor to 10 ppm of $H_2S$ in air and purging between $H_2S$ doses gave rise to reversible responses of consistent magnitude, underscoring the stability of the chemiresistor with respect to the analyte of interest (FIG. 25A). Control devices fabricated with the systematic exclusion of one or more key selector components all yielded significantly lower $H_2S$ responses, establishing that all components are necessary for the observed $H_2S$ sensing performance of SWCNT-P4VP-Pt-POM3 (FIG. 25B). Exposing the sensor to varying $H_2S$ concentrations gave rise to linear change in response in the range 10-0.25 ppm (0.163% ppm$^{-1}$, FIG. 25C). The theoretical detection limit for a 60 second exposure was calculated to be 14 ppb, representing ultra-high $H_2S$ sensing performance at room temperature with respect to trace $H_2S$ (FIG. 25D).

Figure 26A:
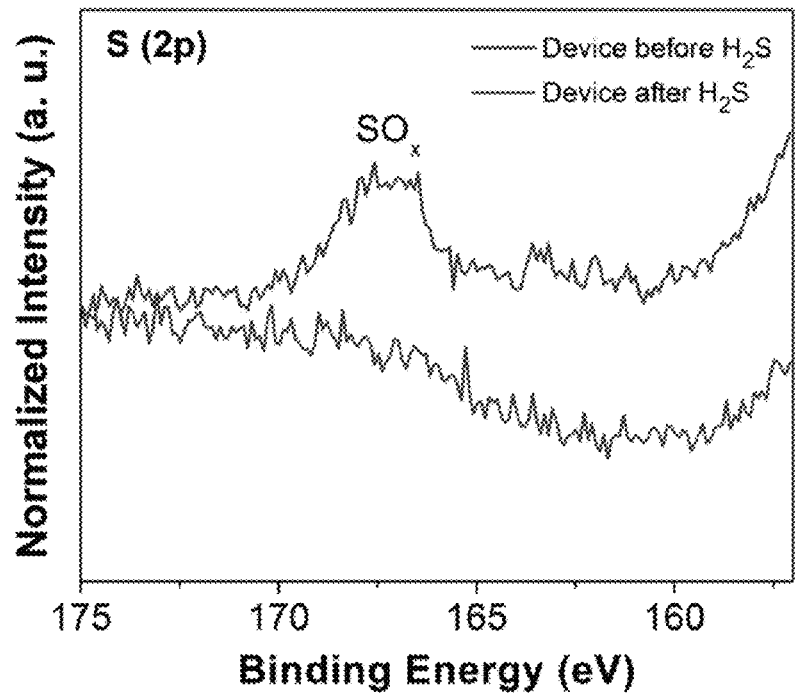
FIGS. 26A-26B depict graphs showing high resolution XPS spectra of S 2p (FIG. 26A) and V 2p (FIG. 26B) of SWCNT-P4VP-Pt-POM3 before and after exposure to $H_2S$ gas (10 ppm) for 1 h at room temperature in air.
Figure 26B:
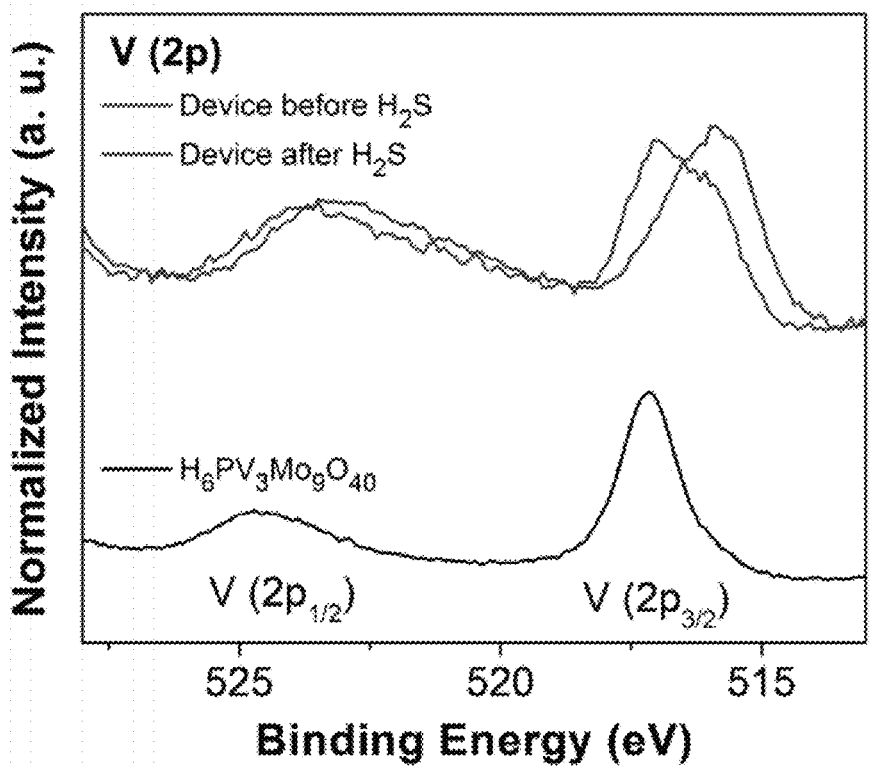

Further experiments were conducted to test the hypothesis that $H_2S$ oxidation gives rise to the chemiresistive sensing response in SWCNT-P4VP-Pt-POM3. Repeated exposure of the device to 10 ppm of $H_2S$ using $N_2$ as the carrier gas resulted in responses of diminishing magnitude, suggesting that $O_2$ is key for consistent sensing responses observed. In a similar vein, repeated exposure of the chemiresistor containing POM2 with lowered vanadium content to $H_2S$ resulted in systematically attenuated responses demonstrating that the importance of increased oxidation reactivity of POM3 in ensuring consistent $H_2S$ sensing performance. Further, probing the chemiresistor surface composition in devices by XPS before and after $H_2S$ exposure showed the appearance of a S 2p peak at 167.3 eV consistent with the generation of $S_xO_y$ species during sensing (FIG. 26A). Integration of the S 2p and Pt 4f peaks areas at three randomly selected locations on the chemiresistor film established a statistically significant increase in surface S content relative to Pt following 1 h of exposure to 10 ppm $H_2S$ at room temperature in air (3.6±1.4% vs 8.7±0.7%). Concurrently, distinct shifts in V 2p binding energies were observed from 517.0 to 515.9 eV (V 2p$_{3/2}$) and from 523.8 to 523.0 eV (V 2p$_{1/2}$) upon $H_2S$ exposure, consistent with the generation of V(IV) in the POM (FIG. 26B). See, for example, C. T. Buru, et al., ACS Appl. Nano Mater. 2019, 3, 658-664, which is incorporated by reference in its entirety.

Figure 27:
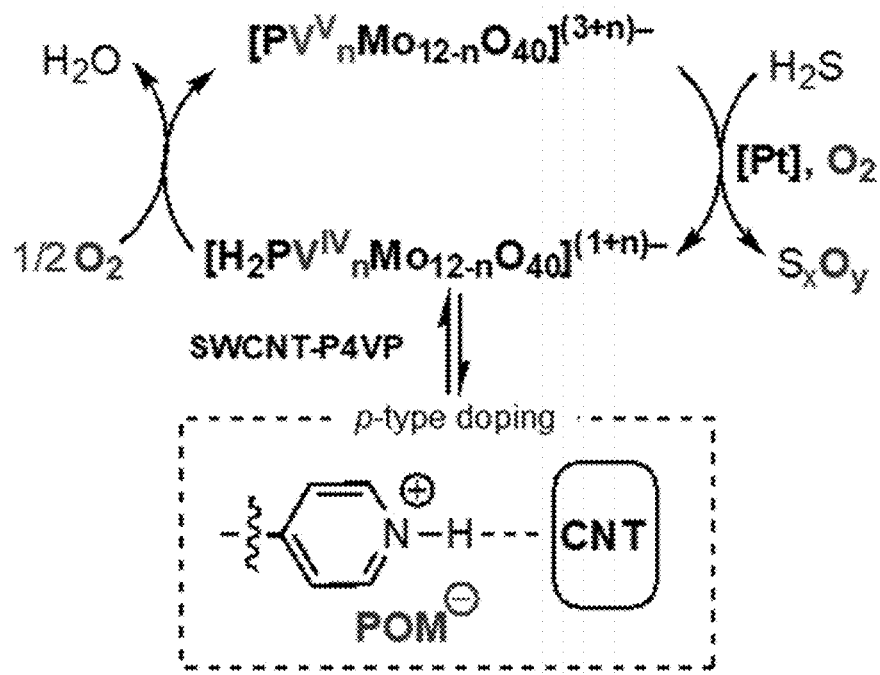
FIG. 27 depicts a schematic of a proposed $H_2S$ sensing mechanism.

Based on the behavior of the sensing system and results of this XPS study, a sensing mechanism shown in FIG. 27 can be proposed. First, $H_2S$ oxidation at the chemiresistor surface can be proposed to generate $S_xO_y$ species wherein $H^+$ and $e^-$ equivalents derived from $H_2S$ are transferred to $[PV^V_nMo_{(12-n)}O_{40}]^{(3+n)-}$ to form $[H_2PV^{IV}_nMo_{(12-n)}O_{40}]^{(1+n)-}$. This step is proposed to proceed according to the known reactivity of Keggin POMs in the aerobic oxidation of organic substrates. Notably, V atoms in the POM are reduced from V(V) to V(IV) and the POM exhibits and increased degree of protonation. It is proposed that proton equivalents generated during $H_2S$ oxidation lead to p-type doping of the SWCNT network, either through direct interaction with the SWCNT sidewalls (see, for example, S. Lin, T. M. Swager, ACS Sens. 2018, 3, 569-573, which is incorporated by reference in its entirety) or by generating pyridinium moieties in P4VP (see for example, B. Yoon, et al., ACS Appl. Mater. Interfaces 2018, 10, 33373-33379, which is incorporated by reference in its entirety). Given that SWCNTs are p-doped in air (see, for example, P. G. Collins, et al., Science 2000, 287, 1801-1804; and D. Kang, et al., Nanotechnology 2005, 16, 1048-1052, each of which is incorporated by reference in its entirety), the electrophilic species in FIG. 27 would give rise to electron depletion at the nanotube surface, increasing hole carrier density and thereby triggering increased conductance in the presence of $H_2S$. In the absence of analyte, $H_2[PV^{IV}{}_nMo_{(12-n)}O_{40}]^{(1+n)-}$ is re-oxidized by $O_2$ with concomitant $H_2O$ formation, thus completing the cycle and regenerating the starting sensing material where initial chemiresistor conductance is restored.

Figure 28A:
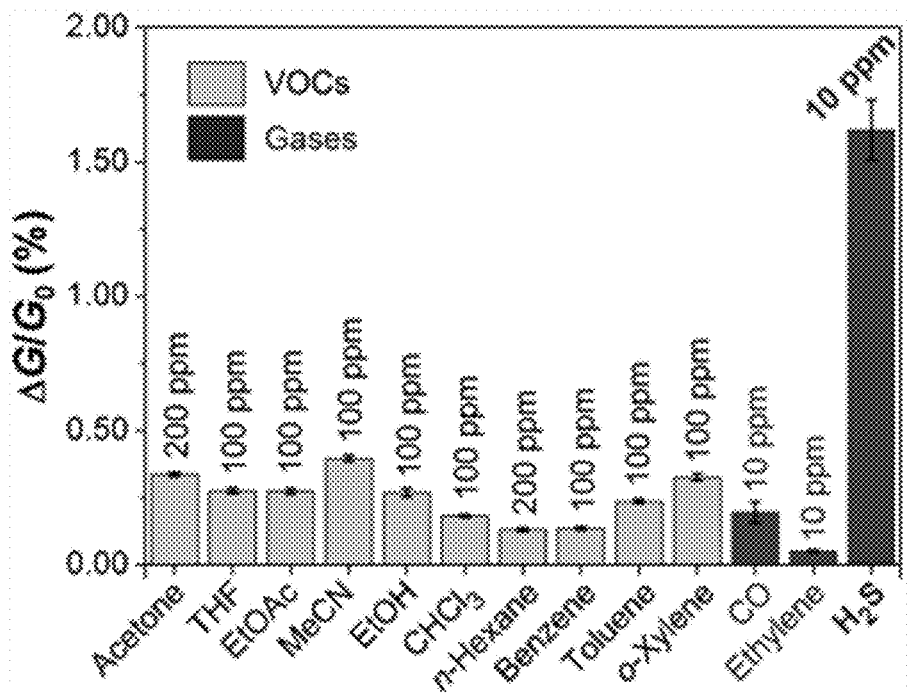
FIG. 28A depicts a graph showing chemiresistive response of SWCNT-P4VP-Pt-POM3 to various interferants.
Figure 28B:
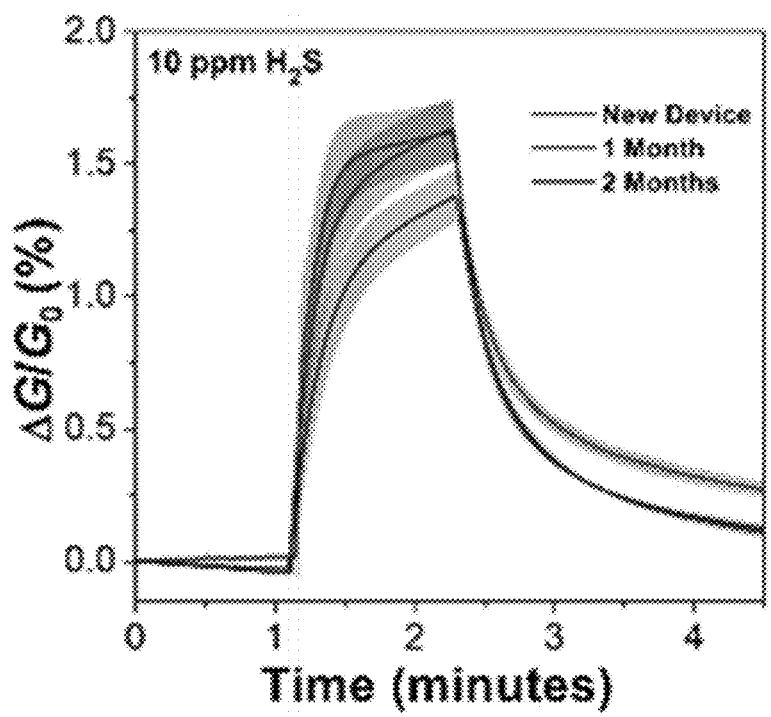
FIG. 28B depicts a graph showing an averaged conductance trace of SWCNT-P4VP-Pt-POM3 in response to 10 ppm of $H_2S$ after storage on laboratory bench for varying time periods.
Figure 28C:
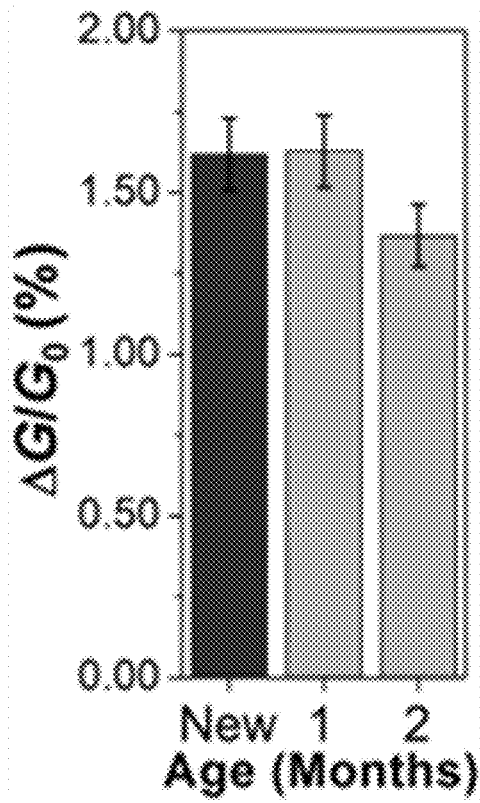
FIG. 28C depicts a graph showing chemiresistive responses of SWCNT-P4VP-Pt-POM3 to 1 min $H_2S$ exposures (10 ppm) after storage on laboratory bench for varying time periods. Shaded areas and error bars represent standard deviations (N=4), all data were collected in air at room temperature.

Having probed the origin of the $H_2S$ response in SWCNT-P4VP-Pt-POM3, the selectivity and stability of the chemiresistor were next examined. Accordingly, the response of SWCNT-P4VP-Pt-POM3 to a range of VOCs and gases were tested and the chemiresistor was found to exhibit excellent selectivity for $H_2S$ (FIG. 28A). The high degree of selectivity compared to molecules such as acetonitrile (MeCN), tetrahydrofuran (THF), carbon monoxide (CO) highlights an advantage of our approach, as these molecules typically interfere in sensing mechanisms relying on metal coordination (see, for example, B. Esser, et al., *Angew. Chem. Int. Ed.* 2012, 51, 5752-5756; and W.-T. Koo, et al., *Chem. Mater.* 2019, 31, 5413-5420, each of which is incorporated by reference in its entirety) but in this case are less prone to undergo oxidative processes. The device showed excellent benchtop stability over time, wherein a minimal loss of $H_2S$ response was observed after storage on a laboratory benchtop for 2 months (FIGS. 28B and 28C). Notably, a of device response $\Delta G/G_0=0.87\pm0.040\%$ to 100 pm of $H_2S$ was retained even after extended storage (3 months), underscoring the robustness of the chemiresistor platform.

In order to examine the broader applicability of the devices described herein, the optimized chemiresistors were incorporated into flexible substrates. Replacing the rigid glass component of the device with a flexible material permits greater form factor variability such that the $H_2S$ sensor architectures can be customized according to the desired application. For this purpose, aromatic polyimides films such as poly(4,4'-oxydiphenylene-pyromellitimide) (Kapton) that have found widespread applications in photoresists, liquid crystal displays and high-performance coatings are particularly attractive due to high thermal stability and favorable mechanical properties. See, for example, Polyimides; D. Wilson, H. D. Stenzenberger, P. M. Hergenrother, Eds.; Blackie: London, 1990; pp 57-78; and Polyimides: Fundamentals and Applications; M. K. Ghosh, K. L. Mittal, Eds.; Marcel Dekker: New York, 1996; pp 7-48, 71-120, each of which is incorporated by reference in its entirety. However, deposition of SWCNT films onto Kapton can be challenging, as de-sorption is facile from the polyimide surface with consequent loss of utility. Accordingly, chemical surface functionalization of Kapton was employed in order to covalently tether P4VP-wrapped SWCNTs onto the polyimide surface.

Figure 29:
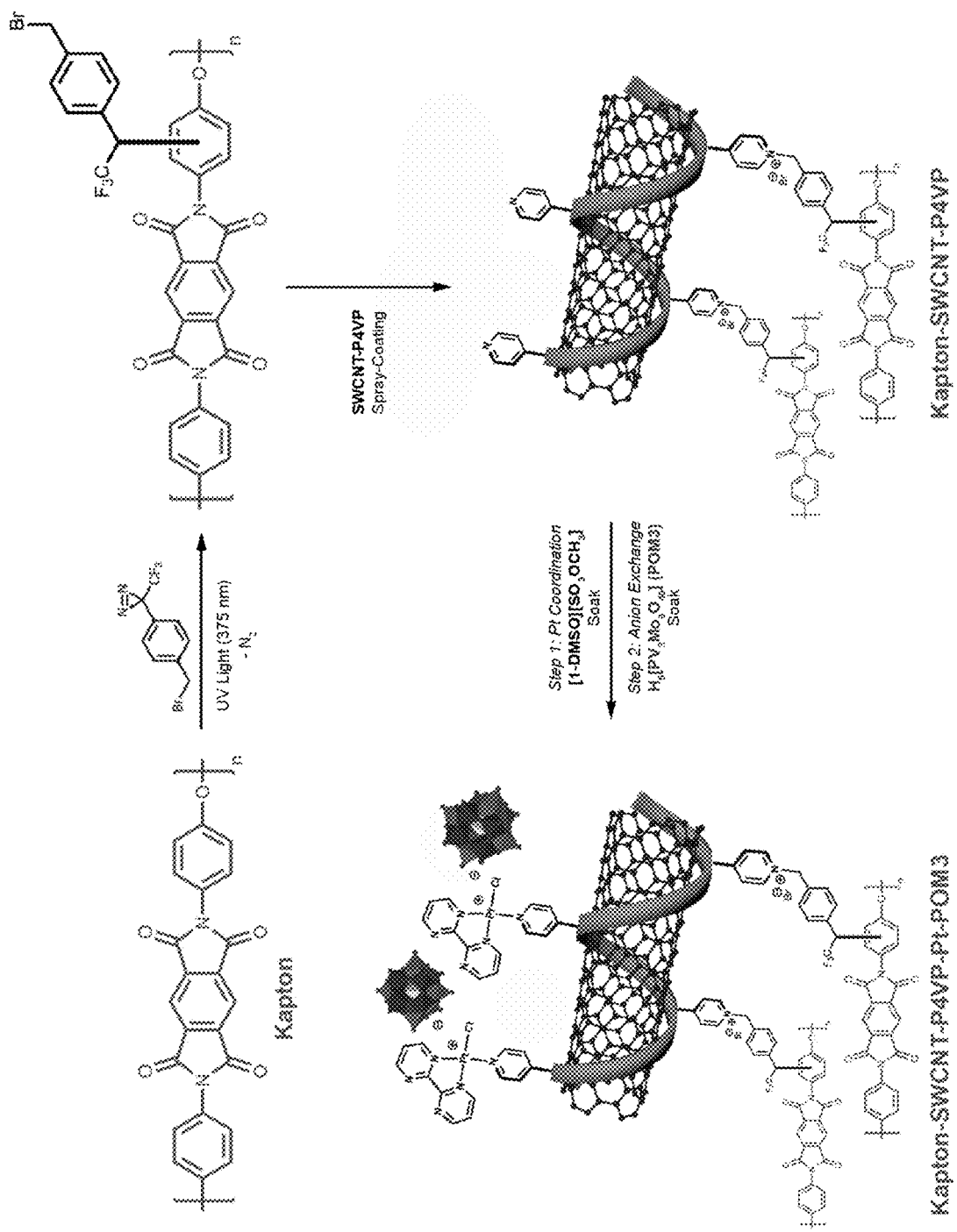
FIG. 29 depicts a scheme for functionalizing a polymer surface.

The Kapton surface functionalization strategy involved installation of alkyl bromide functional groups that can form covalent bonds with P4VP by pyridyl quaternization. To this end, following thermal deposition of electrode patterns on Kapton, the electrode gap surfaces were photochemically functionalized with a diazirine reagent bearing benzyl bromide groups (FIG. 29). See, for example, H. Nakashima, et al., *J. Am. Chem. Soc.* 2006, 128, 15092-15093, which is incorporated by reference in its entirety. The diazirine reagent 3-(4-(bromomethyl)phenyl)-3-(trifluoromethyl)-3H-diazirine was selected due to an optimal balance between reactivity, and ease of synthetic access. The extent and uniformity of surface functionalization were evaluated by XPS using data collected at four randomly chosen locations on the surface. The presence of F and Br in an approximately 3:1 ratio supports the presence of a diazirine-derived organic group on the surface. Following Kapton functionalization, the SWCNT-P4VP composite was deposited in the electrode gaps by spray-coating and annealed at 140° C. for 18 h to ensure reaction between the benzyl bromide groups on the substrate and pyridyl moieties on SWCNT-P4VP composite (FIG. 29). Subsequent immersion of devices in DMF solvent and sonication removed excess/unbound SWCNT-P4VP but resulted in significant amount of SWCNT-P4VP remaining on the Kapton film. The same sonication procedure resulted in rapid SWCNT-P4VP desorption in control devices where the composite was spray-coated on bare Kapton, supporting the productive pyridyl anchoring in the surface-functionalized devices.

With a robust P4VP-SWCNT film deposited onto to the polyimide substrate, the optimized oxidation catalyst system SWCNT-P4VP-Pt-POM3 was introduced into the composite by soaking of the flexible device in respective Pt and POM3 solutions (8 mM, DMSO) (FIG. 29). The performance of the resulting devices in $H_2S$ sensing was excellent, with rapid and reversible responses observed upon exposure to 10 ppm of $H_2S$ in air. In addition, a linear change in response was observed for $H_2S$ concentrations in the range 0.25-10 ppm, with a theoretical LOD of 0.21 ppm. The higher LOD observed for Kapton substrates compared to glass is likely a result of fewer pyridyl sites being available for immobilizing the Pt-POM catalysts due to covalent binding to the functionalized Kapton surface. Nevertheless, the performance of the chemiresistor on flexible Kapton substrates still exceeds detection standards established by NIOSH (see above), demonstrating the generality of our approach in permitting the incorporation of the chemiresistor into both rigid and flexible material supports.

A sensor array can be developed combining two different sensor compositions as described herein. The two different sensor compositions can be directed to two different gases. In the array, the different compositions give different responses to the two different gasses and can differentiate between them. For example, the sensor array can have varying responses to methane and $H_2S$, such that the sensor response informs about a gas mixture composition. This sensor array can detect particular combinations of gases and report relative concentrations of gases, for example.

EXAMPLES

All chemicals, reagents and SWCNTs (CoMoCAT SWCNTs with an average diameter of 1.0 nm, ≥89% carbon basis, ≥99% as carbon nanotubes, lot #: MKBP3333V) were purchased from Sigma-Aldrich and used without additional purification unless noted otherwise. Poly(4-vinylpyridine) ($M_v$=200,000 g/mol) purchased from Scientific Polymer Products, Inc and used as received. Deuterated solvents for NMR spectroscopy were purchased from Cambridge Isotope Laboratories. The compounds $H_{(3+n)}[PV_nMo_{(12-n)}O_{40}]$ (n=1-4), (G. A. Tsigdinos, C. J. Hallada, Inorg. Chem. 1968, 7, 437-441, which is incorporated by reference in its entirety), and [(bpym)Pt(DMSO)Cl][$SO_3OCH_3$] ([1-DMSO][$SO_3OCH_3$]; bpym=2,2'-bipyrimidine, DMSO=dimethylsulfoxide) (J. M. Villalobos, A. J. Hickman, M. S. Sanford, Organometallics 2010, 29, 257-262, and I. Bar-Nahum, A. M. Khenkin, R. Neumann, J. Am. Chem. Soc. 2004, 126, 10236-10237, each of which is incorporated by reference in its entirety), were prepared according to literature procedures. Gas cylinders containing ultra-high purity $CH_4$ and $H_2S$ were purchased from Airgas (Airgas, Dorchester, MA) and equipped with a gas flow regulator to control the output pressure to ~15 psi.

$^1$H NMR spectra were recorded on a Bruker AVANCE 500 (400) spectrometer operating at 500.46 (400) MHz. $^{13}$C NMR spectra were recorded on a 500 spectrometer operating at 125.85 MHz. All $^1$H and $^{13}$C NMR chemical shifts are reported in ppm relative to SiMe$_4$ using the $^1$H (DMSO-d$_6$: 2.50 ppm) and $^{13}$C (DMSO-d$_6$: 39.5 ppm) chemical shifts of the solvent as a standard. $^1$H NMR data is reported as follows: chemical shift, multiplicity (s=singlet, d=doublet, t=triplet, q=quartet, p=pentet, br=broad, m=multiplet, app=apparent, obsc=obscured), coupling constants (Hz), integration, assignment.

ATR-FTIR spectra were obtained using a Thermo Scientific Nicolet 6700 FTIR with a Ge crystal for ATR. Raman spectra were collected with excitation at 532 nm laser using a Horiba LabRAM HR800 Raman spectrometer. X-ray photoelectron spectroscopy (XPS) was performed with a Thermo Scientific K-Alphat Scanning electron microscope (SEM) images were obtained using a Zeiss Merlin high-resolution SEM at an accelerating voltage of 5 kV.

Preparation and Use of Sensors

Preparation of glass sensor substrate. Glass substrates deposited with chromium adhesion layers (10 nm) and gold electrodes (100 nm) were prepared according to a modified literature procedure. See, K. M. Frazier, T. M. Swager. Anal. Chem. 2013, 85, 7154-7158, which is incorporated by reference in its entirety. Briefly, glass slides (VWR Microscope Slides) were cleaned by sonication in acetone and isopropyl alcohol for 5 minutes each. After drying with an N$_2$ stream, the glass substrates were immersed in piranha solution (H$_2$SO$_4$:H$_2$O$_{2(aq)}$, 1:1, v/v) for 30 minutes, rinsed thoroughly with distilled water and then dried in an oven (180° C.) for 18 hours. After cooling to room temperature, a 10 nm layer of chromium (99.99%, R.D. Mathis) and a subsequent 100 nm layer of gold (99.99%, R.D. Mathis) were deposited on the glass slides through a custom stainless-steel mask using a thermal evaporator (Angstrom Engineering). This resulted in five sets of electrode patterns on a single glass slide (FIG. 15 panel A), which was cut into five individual devices. Each device contains a gold pattern of four isolated working electrodes with one shared reference-counter electrode on the glass substrate. The gap between one pair of gold electrodes is 1 mm Prior to the deposition of the chemiresistor platform, the glass substrates were cleaned again by sonication in acetone and isopropyl alcohol for 5 minutes each to remove dust. After drying completely, the glass substrates were immersed in piranha solution (H$_2$SO$_4$:H$_2$O$_{2(aq)}$, 3:1, v/v) for 30 min, rinsed thoroughly with distilled water and then dried under N$_2$.

Preparation of flexible sensor substrate. In a small beaker, the Kapton substrate with printed electrodes was immersed in CH$_2$Cl$_2$ (10 mL). The beaker was placed in an ultrasonic bath for 5 min to clean the sample, after which the sample was allowed to dry under air. The sample was placed on aluminum foil on top of an electric hot plate in the "off" mode. At each gap junction, a single 5.0 µL drop of a solution of 3-(4-(bromomethyl)phenyl)-3-(trifluoromethyl)-3H-diazirine (10 mg/mL in CH$_2$Cl$_2$) was carefully deposited using a micropipette. The drops may coalesce with neighboring drops during this procedure. The hot plate was switched at 50° C. until the solvent had evaporated. The portions of the device on either side of the gaps were covered with a small square of white paper to prevent excessive irradiation of the non-gap areas. Next, the Petri dish was placed under a handheld UV lamp and irradiated with long-wave UV light (~375 nm) for 1 h. The sample was then placed into a small beaker, covered with CH$_2$Cl$_2$ (10 mL), and placed in an ultrasonic bath for 5 min. The sample was then rinsed with acetone to remove any residual diazirine reagent.

Figure 15:
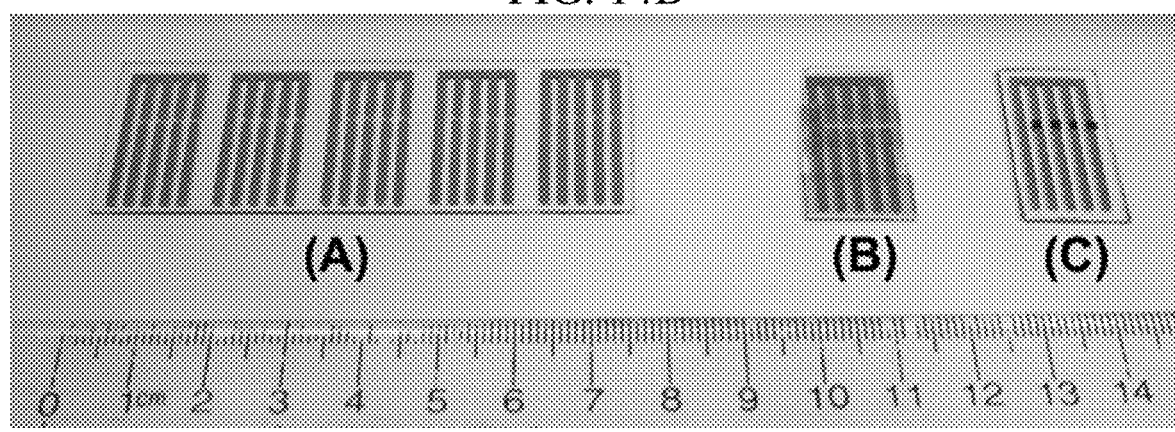
FIG. 15 depicts a sensor. Panel A shows a microscope glass slide with five electrode patterns after thermal deposition of Cr (10 nm) and Au (100 nm) layers. Panel B shows an individual device with film mask prior to spray coating. Panel C shows an individual device with spray-coated SWCNT-P4VP network after removal of film mask.

Fabrication of SWCNT-P4VP Chemiresistor Platform. A literature procedure was adapted. See, B. Yoon, S. F. Liu, T. M. Swager, Chem. Mater. 2016, 28, 5916-5924, which is incorporated by reference in its entirety. To a solution containing 0.050 g of P4VP dissolved in 10 mL of DMF, 0.005 g of SWCNT was added and then the resulting mixture was sonicated for 1 hour in an ultrasonic bath (Branson, 3510) chilled with ice. The supernatant was directly used for the device fabrication via spray coating as follows. The desired amount of SWCNT-P4VP dispersion (0.5 mL) was loaded into an airbrush (Revolution BR, Iwata) and manually spray-coated on the gap of gold electrodes on the sensor substrate (glass or Kapton) through a homemade transparency film (CG3700, 3M) mask (FIG. 15 panel B). In order to prevent unwanted nozzle drips and over-wetting of the substrate surface that results in non-uniform deposition of composites, the dispersion was sprayed intermittently (~0.5 second spray exposures) multiple times with an injection rate of about 40 µL/min at a distance of 10 cm from the substrate placed on a 140° C. hot plate using N$_2$ carrier gas (2 bar pressure). The spraying process was repeated with a second 0.5 mL portion of SWCNT-P4VP dispersion and the device was allowed to dry on the hot plate for 15 minutes. After this time, the film mask was removed and the resulting substrate was thermally annealed at 140° C. for 18 hours. In order to remove excess polymers and non-immobilized P4VP-SWCNT composites, the chemiresistor substrate was then soaked in 10 mL of acetonitrile (MeCN) for 30 minutes followed by washing with MeCN dropwise (5 mL) and dried under vacuum for 6 hours. The resistance across the SWCNT-P4VP network after this procedure typically ranged between 1.0-3.0 kΩ as measured by an ohmmeter (FIG. 15 panel c).

Metal Incorporation into SWCNT-P4VP Chemiresistor Platform and Anion Exchange. The substrate (glass or Kapton) containing the SWCNT-P4VP composite was first soaked in 5 mL of a DMSO solution containing [1-DMSO][SO$_3$OCH$_3$] (0.04 mmol) for 18 hours at room temperature. The substrate was then soaked in 10 mL of pure DMSO for 30 minutes at room temperature to remove unbound Pt complexes, washed with DMSO dropwise (5 mL) and dried under vacuum for 6 hours. The resulting composite is denoted as SWCNT-P4VP-Pt. In order to achieve anion exchange, the device was then soaked in 5 mL of a DMSO solution containing H$_{(3+n)}$[PV$_n$Mo$_{(12-n)}$O$_{40}$] (n=1-4) (0.04 mmol) for 18 hours at room temperature. The substrate was then soaked in 10 mL of pure DMSO for 30 minutes at room temperature to remove unbound POMs, washed with DMSO dropwise (5 mL) and soaked in DI water for 5 minutes at room temperature. The device was then washed with DI water dropwise (5 mL) and air dried. The chemiresistor thus obtained is denoted as SWCNT-P4VP-Pt-POMX (X=1-4).

Figure 10B:
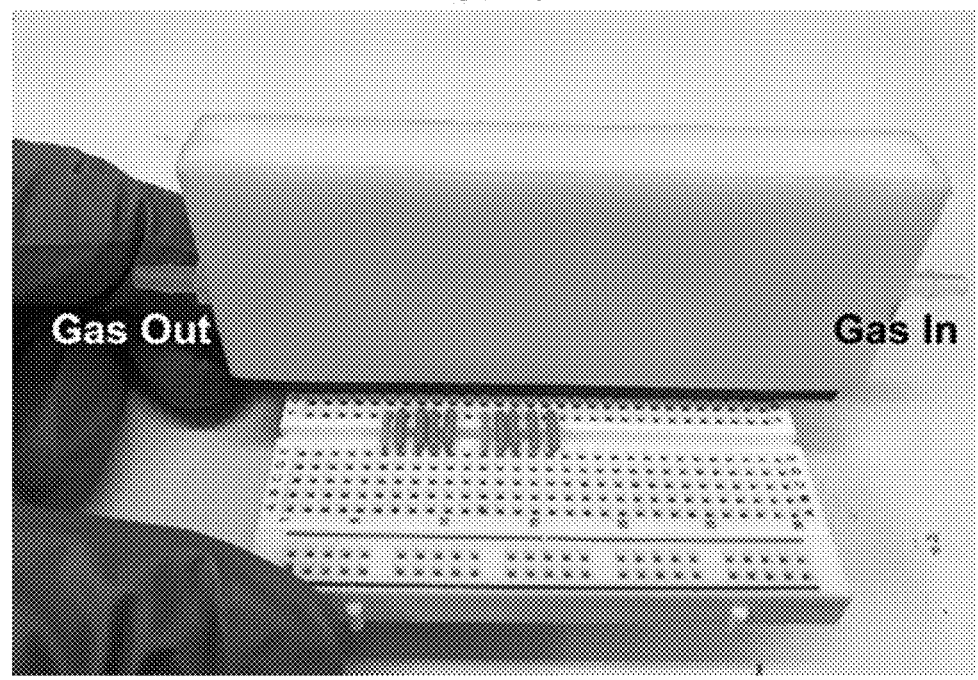
Figure 10C:
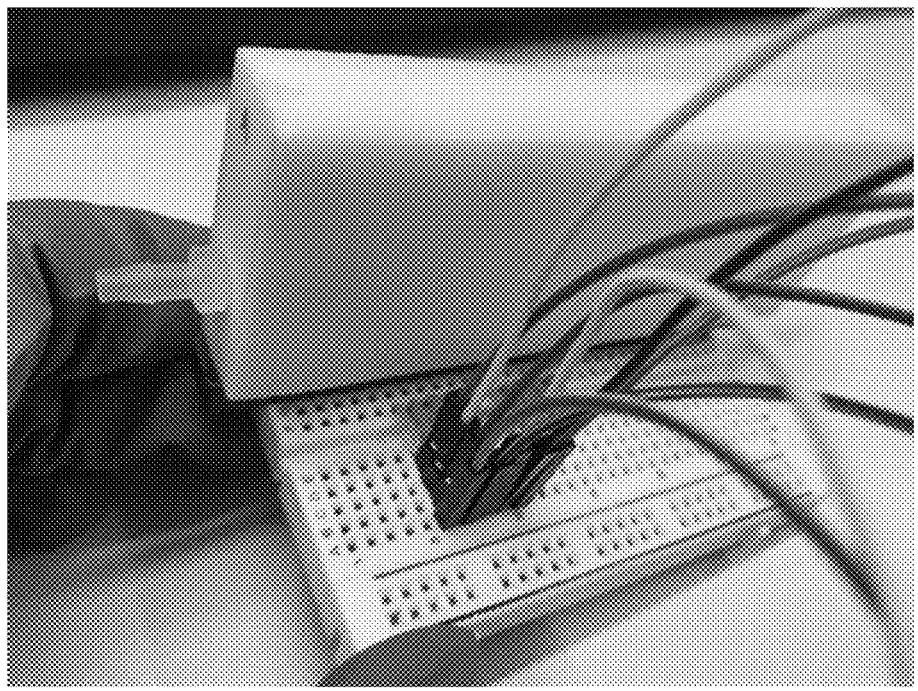
Figure 16:
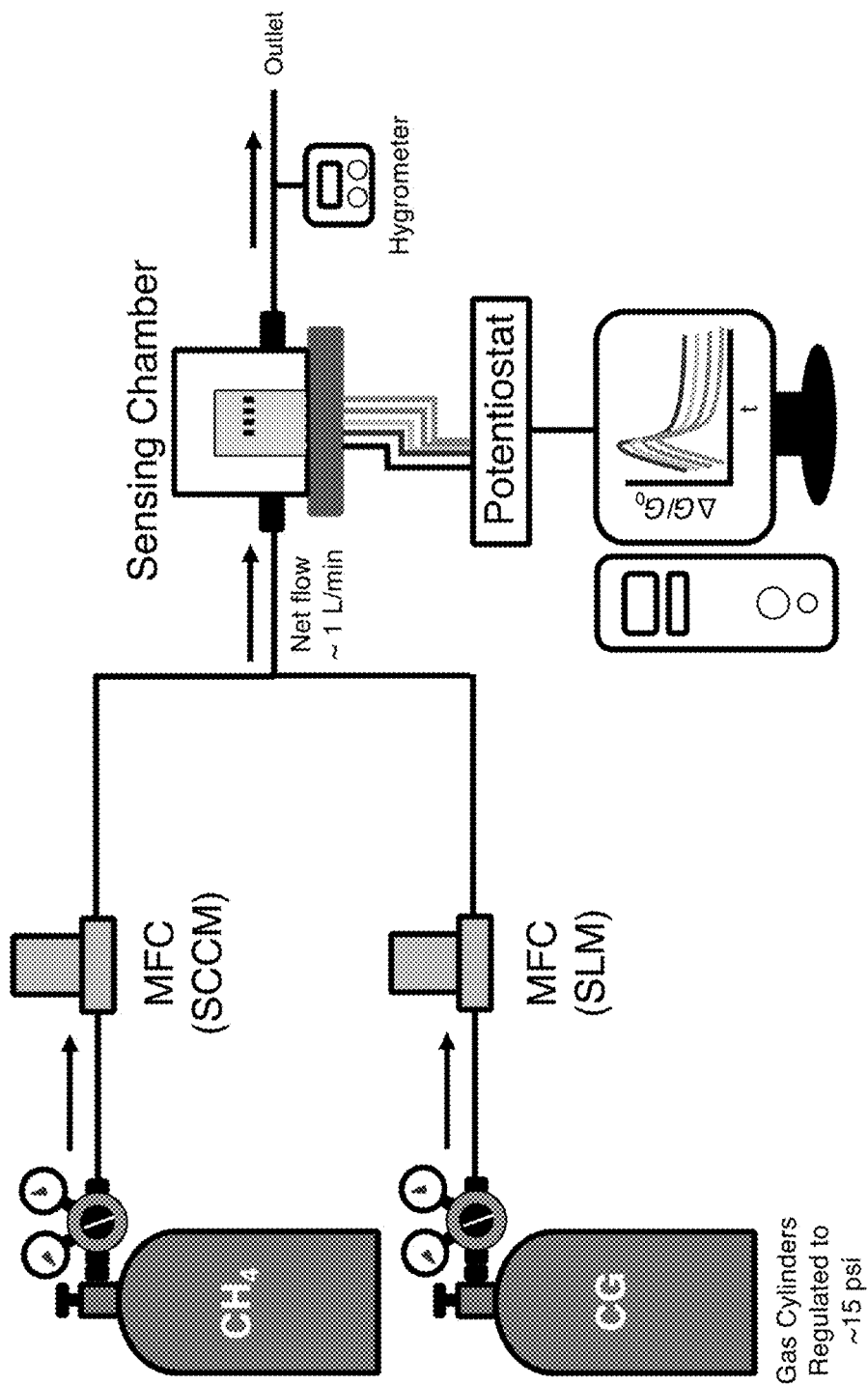
FIG. 16 depicts a schematic of a chemiresistive $CH_4$ sensing setup. CG=Carrier Gas (Compressed air, dry synthetic air or $N_2$); MFC=Mass Flow Controller; SLM=Standard Liter per Minute; SCCM=Standard Cubic Centimeter per Minute.
Figure 17A:
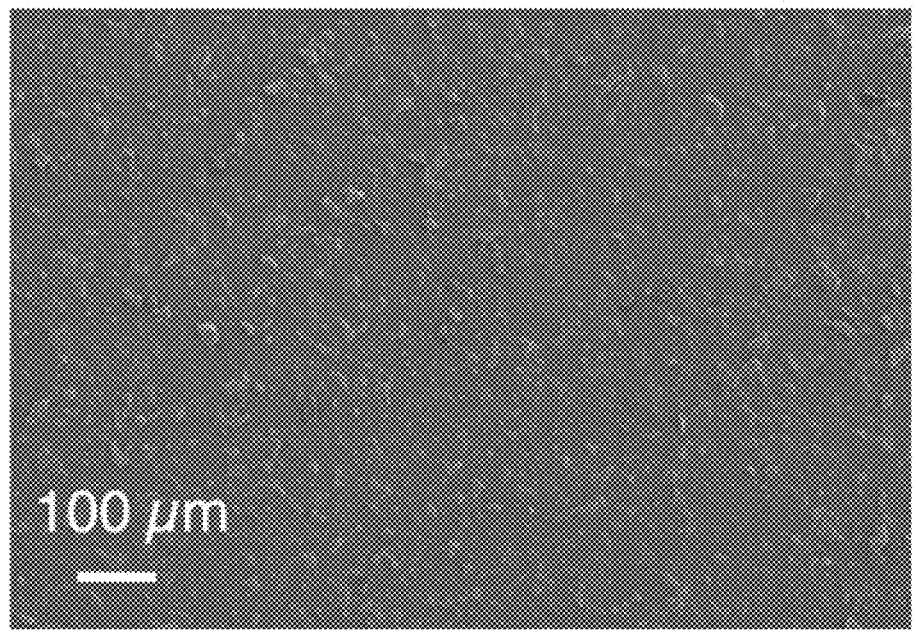
FIGS. 17A-17D depict SEM images.
Figure 17B:
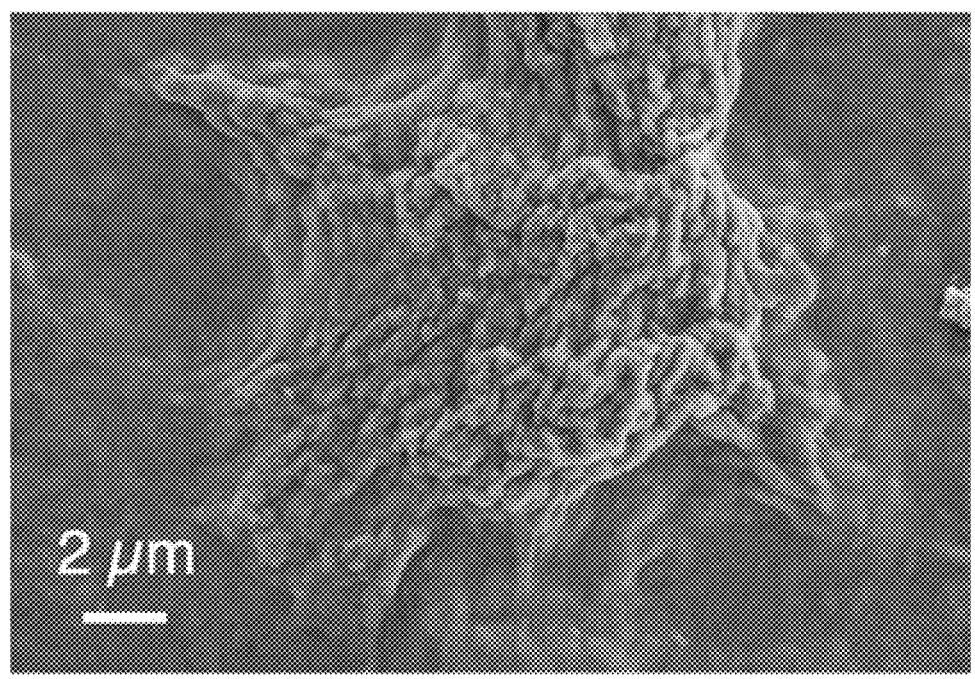
Figure 17C:
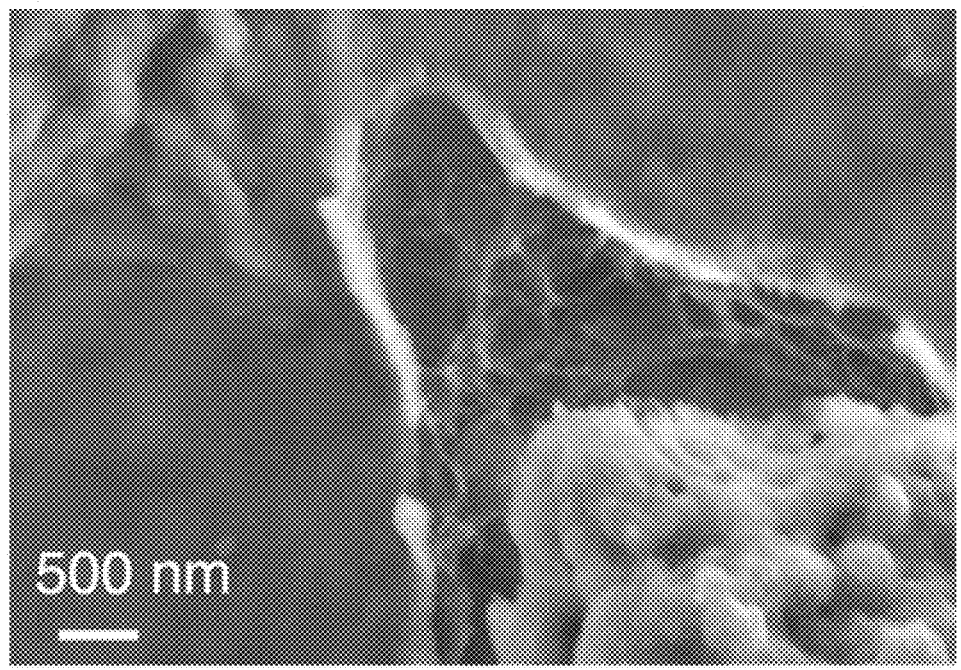
Figure 17D:
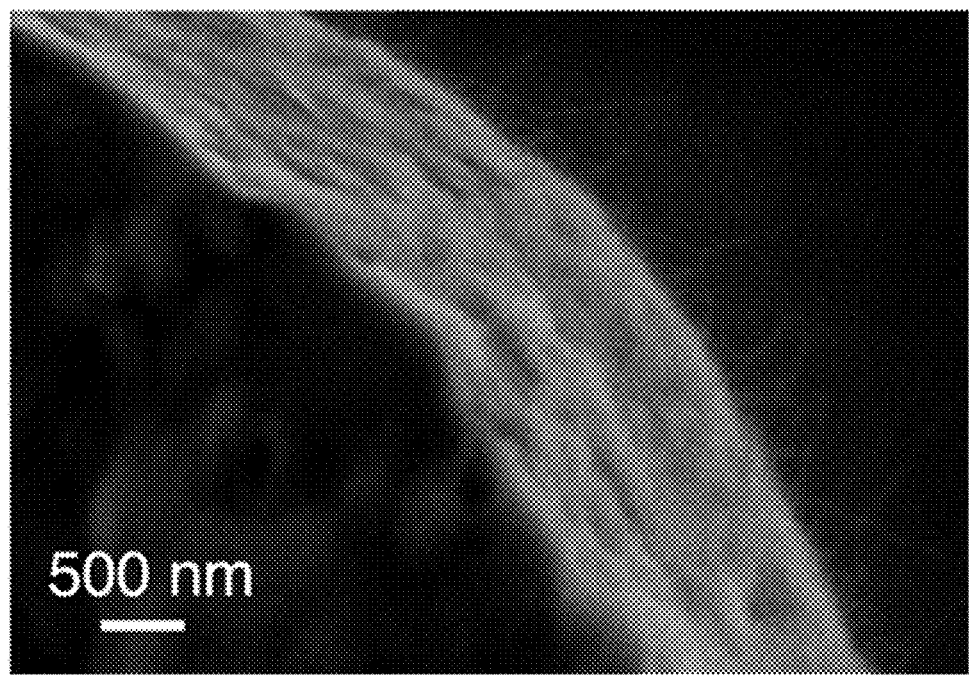
Figure 19:
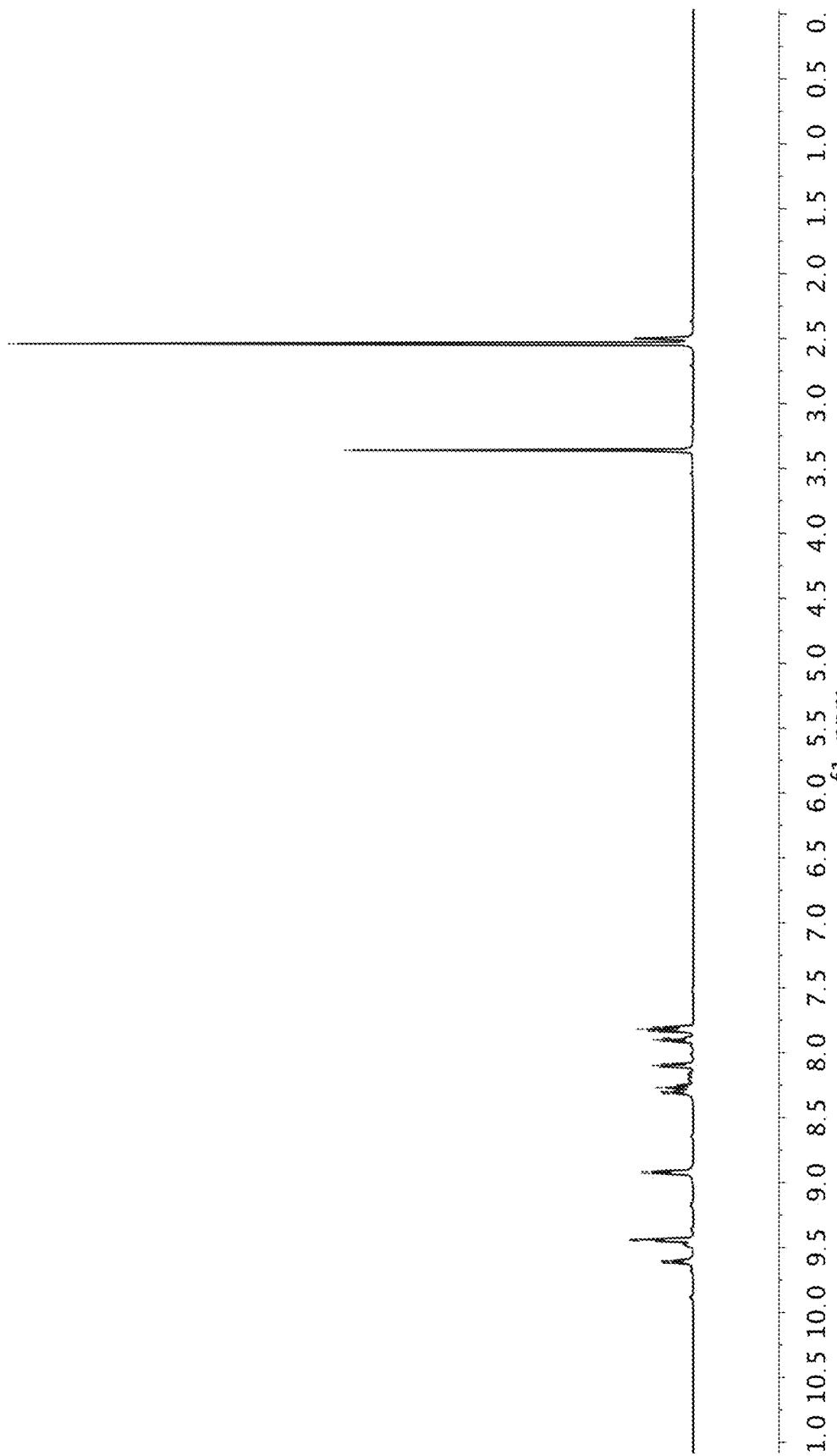
FIG. 19 depicts an $^1H$ NMR (400 MHz) spectrum of [1-Py][$SO_3OCH_3$] in DMSO-$d_6$ at 23° C.
Figure 20:
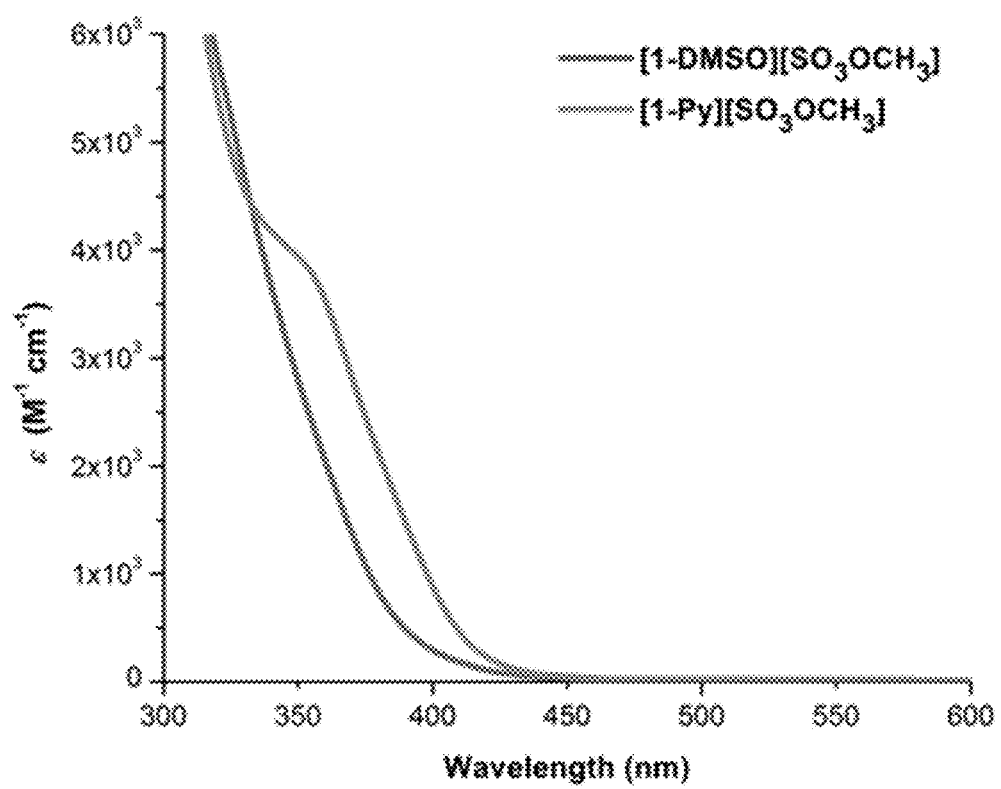
FIG. 20 depicts overlaid electronic absorption spectra of [1-DMSO][$SO_3OCH_3$] and [1-Py][$SO_3OCH_3$] in DMSO at 23° C.
Figure 21:
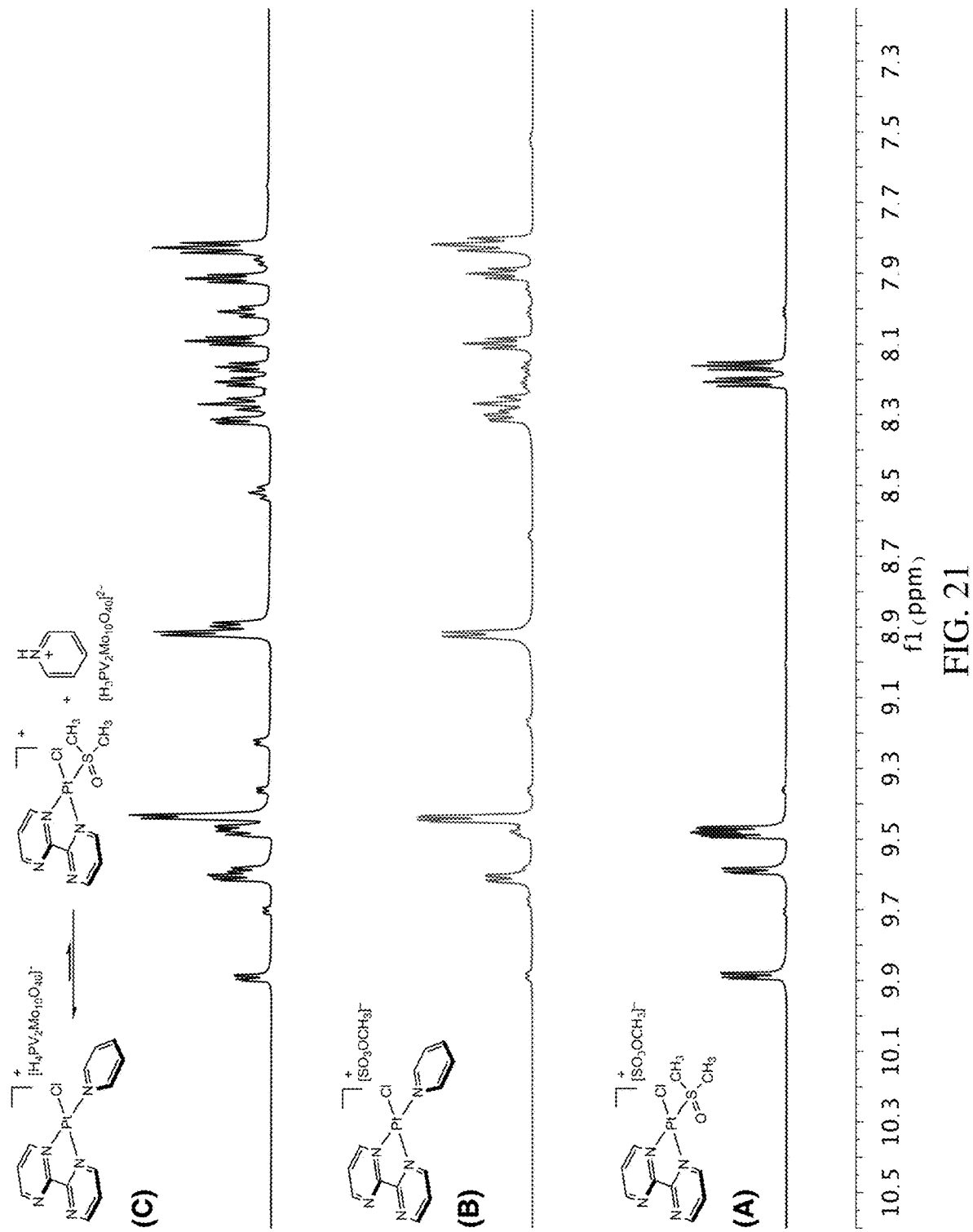
FIG. 21 depicts the aromatic region of stacked $^1H$ NMR (400 MHz) spectra corresponding to a) [1-DMSO][$SO_3OCH_3$], b) [1-Py][$SO_3OCH_3$] and c) the reaction between [1-Py][$SO_3OCH_3$] and [$H_5PV_2Mo_{10}O_{40}$]. Spectra collected in DMSO-$d_6$ at 23° C.

CH$_4$ and H$_2$S Detection Measurements. The fabricated device containing the SWCNT-P4VP-Pt-POM chemiresistor was inserted into a 2×30 pin edge connector (TE Connectivity AMP Connectors) mounted on a solderless breadboard (FIG. 10A), and then enclosed with a custom-built PTFE chamber containing a small gas inlet and outlet (FIG. 10B). The gold electrodes of the device were connected to an Agilent Keysight 34970A potentiostat equipped with a 34901A 20-channel multiplexer (2/4-wire) module (FIG. 10C). The potentiostat was connected to the sensing laptop using an Agilent 82357B GPIB-USB Interface High-Speed USB 2.0 serial cable and controlled using BenchLink Data Logger 3 (available free of charge online). The scan rate was set to 1 scan/second. Two mass flow controllers (MFCs, Alicat Scientific) were used to deliver a mixture of various concentration of $CH_4$ or $H_2S$ in a carrier gas ($N_2$ or air) to the device's enclosure with a total flow rate of 1 L/min (FIG. 16). The carrier gas flow rate was controlled using an Alicat Scientific MC-10SLPM-D/5M MFC and $CH_4/H_2S$ flow rates were controlled using an Alicat Scientific MC-10SCCM-D/5M MFC. Flow rates were remotely controlled by connecting the MFCs to the sensing laptop via a 6' USB-MD8-232 double-ended 8-pin mini-DIN to USB serial cable (Alicat Scientific) and using Flow Vision SC software (Alicat Scientific; available free of charge online) to change flow rates using a script. The potentiostat applied a constant potential across the electrodes, and the resistance for each channel of the device was recorded using PSTrace5 software during $CH_4$ and $H_2S$ exposures. The change in device resistance resulting from $CH_4$ and $H_2S$ exposure was converted to the normalized change in conductance [$\Delta G/G_0$ (%)=$(I-I_0)/I_0 \times 100\%$; $I_0$=initial current], which was taken as the device's response. The humidity of the measurement was measured using a VWR traceable hygrometer placed near the exhaust gas. For selectivity studies, an identical sensing setup was employed with the exception that a gas generator (FlexStream, Kin-Tek) was used to produce vapors from liquids. A schematic of the setup is shown in FIG. 16.

Preparation of Model Platinum Complexes and Associated Data

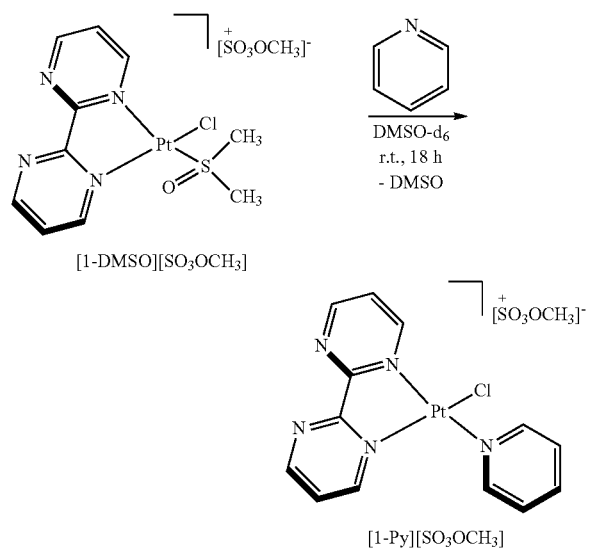

[1-DMSO][SO$_3$OCH$_3$]

[1-Py][SO$_3$OCH$_3$]

In situ generation of [1-Py][SO$_3$OCH$_3$]. A 20 mL scintillation vial was charged with a magnetic stir bar, 0.010 g (0.017 mmol) of [1-DMSO][SO$_3$OCH$_3$] and 0.6 mL of DMSO-d$_6$. To the stirring solution, 1.4 μL (0.018 mmol) of pyridine was added via microliter syringe and the reaction was stirred at room temperature for 18 hours. During this time, a color change from faint yellow to a more intense yellow was observed. The solution was then transferred to an NMR tube for analysis. Conversion to the proposed pyridine adduct was observed by $^1$H and $^{13}$C NMR spectroscopies. $^1$H NMR (DMSO-d$_6$, 296 K): δ 9.61 (dd, J=5.9, 2.0 Hz, 1H, bipyrimidine aryl C—H), 9.44 (app dd, J=4.8, 1.9 Hz, 2H, two overlapping inequivalent bipyrimidine aryl C—H), 8.92 (d, J=5.0 Hz, 2H, pyridine aryl C—H), 8.31 (dd, J=5.9, 1.9 Hz, 1H, bipyrimidine aryl C—H), 8.27 (t, J=7.7 Hz, 1H, pyridine aryl C—H), 8.10 (dd, J=5.9, 4.8 Hz, 1H, bipyrimidine aryl C—H), 7.90 (dd, J=5.9, 4.8 Hz, 1H, bipyrimidine aryl C—H), 7.82 (t, J=7.1 Hz, 2H, pyridine aryl C—H), 3.36 (s, 3H, [OSO$_3$CH$_3$]$^-$). $^{13}$C{$^1$H} NMR DMSO-d$_6$, 295 K): δ 162.06 (s, bipyrimidine aryl C), 161.28 (s, bipyrimidine aryl C), 161.18 (s, bipyrimidine aryl C), 160.33 (s, bipyrimidine aryl C), 156.53 (s, bipyrimidine aryl C), 155.65 (s, bipyrimidine aryl C), 153.15 (s, pyridine aryl C), 141.11 (s, pyridine aryl C), 127.76 (s, pyridine aryl C), 125.31 (s, bipyrimidine aryl C), 124.58 (s, bipyrimidine aryl C), 52.77 (s, [OSO$_3$CH$_3$]$^-$).

Reaction of [1-Py][SO$_3$OCH$_3$] with [H$_5$PV$_2$Mo$_{10}$O$_{40}$] (Method A). A 20 mL scintillation vial was charged with a magnetic stir bar, 0.010 g (0.017 mmol) of [1-DMSO][SO$_3$OCH$_3$] and 0.6 mL of DMSO-d$_6$. To the stirring solution, 1.4 μL (0.018 mmol) of pyridine was added via microliter syringe and the reaction was stirred at room temperature for 18 hours. After this time, 0.039 g (0.017 mmol) of [H$_5$PV$_2$Mo$_{10}$O$_{40}$]·32H$_2$O was added to the solution and the reaction was stirred at room temperature for an additional 18 hours. The solution was then transferred to an NMR tube for analysis.

Reaction of [1-Py][SO$_3$OCH$_3$] with [H$_5$PV$_2$Mo$_{10}$O$_{40}$] and Isolation of Product Mixture (Method B). A 20 mL scintillation vial was charged with a magnetic stir bar, 0.030 g (0.052 mmol) of [1-DMSO][SO$_3$OCH$_3$] and 1 mL of anhydrous DMSO. To the stirring solution, 4.4 μL (0.055 mmol) of pyridine was added via microliter syringe and the reaction was stirred at room temperature for 18 hours. After this time, 0.120 g (0.052 mmol) of [H$_5$PV$_2$Mo$_{10}$O$_{40}$]·32H$_2$O was added and the reaction stirred at room temperature for an additional 18 hours. During this time, a color change from faint yellow to a red-orange yellow was observed. The solution was then transferred to a 25 mL round-bottomed flask and attached to a receiving Schlenk flask via a 2-way male U-adaptor. The volatiles were then vacuum transferred to the cooled (−78° C.) receiving flask at 35° C. under vacuum over the course of 1 hour. To the orange oily film that remained, diethyl ether (10 mL) was added and the mixture sonicated to generate suspended solids. The ether was decanted, and the solids dried under vacuum. The solids were then transferred to a small Buchner funnel, rinsed dropwise with cold water (~0° C., 10 mL) to remove any excess H$_5$PV$_2$Mo$_{10}$O$_{40}$ and/or methyl bisulfate. The solids were then air-dried and dried under high vacuum to afford yellow-orange solids (0.085 g). $^1$H NMR analysis of the product revealed an identical ratio of platinum complexes as in the case of Method A. These results demonstrate that product isolation does not perturb the equilibrium observed in Method A.

Reaction of Isolated Pt/POM Mixture with CH$_4$. A 40 mL scintillation vial was charged with the isolated product of the reaction [1-Py][SO$_3$OCH$_3$]+[H$_5$PV$_2$Mo$_{10}$O$_{40}$] (0.015 g total; prepared by Method B above) and 1 mL of D$_2$O. The vial was sealed with a rubber septum, and CH$_4$ was bubbled through the slurry for 15 minutes and a CH$_4$-filled balloon was attached to the flask. The reaction was stirred at room temperature for 3 hours. The suspension was then filtered through a pad of Celite and the filtrate was transferred to an NMR tube for analysis. MeOH was observed, demonstrating the competence of the mixture in CH$_4$ oxidation.

Other embodiments are within the scope of the following claims.

What is claimed is:

1. A sensor for detecting an analyte comprising:
   a composition including:
   a semiconducting material;
   an oxidation catalyst proximate to the semiconducting material; and
   an oxidation enhancer associated with the oxidation catalyst,
   wherein the sensor detects a thiol or methane by a change in conductivity of electrical characteristics of a circuit containing the sensor.

2. The sensor of claim 1, further comprising a polymer associating the oxidation catalyst with the semiconducting material.

3. The sensor of claim 2, wherein the polymer includes poly(4-vinylpyridine) (P4VP).

4. The sensor of claim 2, wherein the polymer is hyperbranched.

5. The sensor of claim 2, wherein the polymer backbone is partially or fully comprised of non-carbon elements.

6. The sensor of claim 2, wherein the polymer has a porous structure.

7. The sensor of claim 2, wherein the polymer is produced from condensation of metal or main group element with other elements from groups 15, 16 of 17.

8. The sensor of claim 7, wherein the group 16 elements can contain oxygen or sulfur.

9. The sensor of claim 1, wherein a conductivity of the semiconducting material changes when the oxidation catalyst is reacting with methane.

10. The sensor of claim 1, wherein a conductivity of the semiconducting material changes when the oxidation catalyst is reacting with sulfide thiol.

11. The sensor of claim 1, wherein the semiconductor material functions as the oxidation enhancer.

12. The sensor of claim 1, wherein the semiconducting material includes a carbon nanotube.

13. The sensor of claim 12, wherein the carbon nanotube is a single-walled carbon nanotube.

14. The sensor of claim 1, wherein the semiconducting material includes a nanocarbon material.

15. The sensor of claim 14, wherein the semiconducting material contains graphene.

16. The sensor of claim 1, wherein the semiconducting material is modified to bind the oxidation catalyst.

17. The sensor of claim 1, wherein the oxidation enhancer includes a polyoxometalate.

18. The sensor of claim 17, wherein the polyoxometalate is a tungsten polyoxometalate or a molybdenum polyoxometalate.

19. The sensor of claim 18, wherein the polyoxometalate includes vanadium.

20. The sensor of claim 1, wherein the oxidation enhancer includes a polymer.

21. The sensor of claim 1, wherein the oxidation enhancer includes an inorganic oxide, inorganic salt, inorganic halide, or a high electron affinity molecule.

22. The sensor of claim 1, wherein the oxidation enhancer includes nanoparticles.

23. The sensor of claim 1, wherein the oxidation enhancer includes a porous solid.

24. The sensor of claim 1, wherein the oxidation catalyst is a methane oxidation catalyst or a thiol oxidation catalyst.

25. The sensor of claim 1, wherein the oxidation catalyst includes platinum, tungsten, molybdenum, copper, iron, osmium, cobalt, rhodium, palladium, vanadium, osmium, gold, cerium, iridium, iron, manganese, silver, or europium.

26. The sensor of claim 1, wherein the oxidation catalyst includes nanoparticles.

27. The sensor of claim 1, wherein the composition is located between two electrodes.

28. The sensor of claim 1, wherein the composition is deposited on a flexible substrate.

29. The sensor in claim 1, wherein the sensor detects methane by said change in conductivity of electrical characteristics of the circuit containing the sensor.

30. The sensor in claim 1, wherein the sensor detects a thiol by said change in conductivity of electrical characteristics of the circuit containing the sensor.

31. The sensor in claim 1, wherein the sensor detects a thiol and a methane by said change in conductivity of electrical characteristics of the circuit containing the sensor.

32. The sensor claim 1, wherein the sensor includes a second composition that differs from the composition.

33. A sensor for detecting an analyte comprising:
    a composition including:
    a semiconducting material; and
    a molecular methane oxidation catalyst that is proximate the semiconducting material,
    wherein the sensor detects a thiol or methane by a change in conductivity of electrical characteristics of a circuit containing the sensor.

34. A method of sensing an analyte comprising:
    exposing the sensor of claim 1 to a sample; and
    measuring an electrical property of the sensor.

35. The method of claim 34, further comprising detecting methane.

36. A method of preparing a sensor for detecting an analyte comprising:
    placing a substrate, a semiconducting material, an oxidation catalyst proximate to the semiconducting material, and an oxidation enhancer associated with the oxidation catalyst in electrical communication with at least two electrodes,
    wherein the sensor detects a thiol or methane by a change in conductivity of electrical characteristics of a circuit containing the sensor.

37. A sensor array comprising a first sensor and a second sensor, the first sensor responding to a first gas and the second sensor responding to a second gas, wherein the sensor array provides information about a gas mixture composition, wherein the first sensor or second sensor detects a thiol or methane by a change in conductivity of electrical characteristics of a circuit containing the sensor.

* * * * *